United States Patent [19]
Arita et al.

[11] Patent Number: 6,156,766
[45] Date of Patent: Dec. 5, 2000

[54] BENZAMIDE COMPOUNDS AND PHARMACEUTICAL USE THEREOF

[75] Inventors: Masafumi Arita, Chikujo-gun; Tadamasa Saitoh, Iruma; Masanori Minoguchi, Iruma; Keiji Yamagami, Iruma; Hiroyuki Satoh, Chikujo-gun, all of Japan

[73] Assignee: Yoshitomi Pharmaceutical Industries, Ltd., Osaka, Japan

[21] Appl. No.: 09/252,079

[22] Filed: Feb. 18, 1999

Related U.S. Application Data

[62] Division of application No. 08/727,669, filed as application No. PCT/JP95/00747, Apr. 17, 1995, Pat. No. 5,958,944.

[30] Foreign Application Priority Data

Apr. 18, 1994 [JP] Japan ........................ 6-78280

[51] Int. Cl.$^7$ .................... A61K 31/437; A61K 31/519; C07D 471/04; C07D 487/04; A61P 9/12
[52] U.S. Cl. .......... 514/300; 514/241; 514/247; 514/246; 514/249; 514/258; 514/261; 514/301; 514/303; 514/311; 514/313; 514/352; 514/384; 540/180; 540/184; 544/182; 544/194; 544/224; 544/254; 544/277; 544/280; 544/258; 544/298; 544/322; 544/336; 544/331; 544/362; 546/113; 546/117; 546/118; 546/119; 546/122; 546/164; 546/174
[58] Field of Search ................... 514/241, 243, 514/246, 247, 248, 249, 256, 258, 261, 300, 301, 302, 303, 311, 313, 352, 383, 384, 407; 544/182, 194, 224, 215, 254, 256, 280, 277, 258, 297, 298, 322, 326, 330; 546/113, 117, 118, 119, 122, 164, 174, 309; 548/255, 265.6, 371.7; 540/180, 184

[56] References Cited

U.S. PATENT DOCUMENTS

| | | | |
|---|---|---|---|
| 4,052,377 | 10/1977 | Junge | 260/154 |
| 4,093,734 | 6/1978 | Kruger | 424/274 |
| 4,305,940 | 12/1981 | Quadro | 424/248.54 |
| 4,720,500 | 1/1988 | Cotrel | 514/300 |
| 4,753,933 | 6/1988 | Cotrel | 514/228.2 |
| 4,948,891 | 8/1990 | Schnur | 544/329 |
| 4,973,594 | 11/1990 | Tyers | 514/299 |
| 4,978,531 | 12/1990 | Yamazaki et al. | 424/448 |
| 5,478,838 | 12/1995 | Arita et al. | 514/300 |

FOREIGN PATENT DOCUMENTS

| | | |
|---|---|---|
| 0 218 027 A1 | 4/1987 | European Pat. Off. |
| 0 268 267 A2 | 5/1988 | European Pat. Off. |
| 0 370 498 A2 | 5/1990 | European Pat. Off. |
| 3042687 A1 | 8/1981 | Germany |
| 3804346 A1 | 8/1989 | Germany |
| 62-090657 | 4/1987 | Japan |
| 7603234 | 3/1977 | South Africa |
| 438120 | 2/1977 | Spain |

OTHER PUBLICATIONS

R. Moffett et al. "Antiulcer Agents. p–Aminobenzamido Aromatic Compounds[1]", Journal of Medicinal Chemistry, vol. 14, No. 10, 1971, pp. 963–968.

J. Archibald et al., "Benzamidopiperidines. 3. Carbocyclic Derivatives Related to Indoramin", Journal of Medicinal Chemistry, vol. 17, No. 7, 1974, pp. 739–744.

Chemical Abstract No. 90:72068j, vol. 90, (1979) of Spanish Patent No. 456,989.

English Abstract No. 87–232810/33 of Japanese Patent Unexamined Publication No. 158252/1987.

English Abstract No. 87–232811/33 of Japanese Patent Unexamined Publication No. 158253/1987.

S. Kumar et al. J. Med., Chem. 27, pp. 1083–1089.

G. Pagani et al., Ed. Sci., vol. 26, No. 2, pp. 118–131.

FD King, Med. Chem., Principles and Practice, The Royal Society of Chemistry, Thomas Graham House, The Science Park, Cambridge, pp. 207–208.

*Primary Examiner*—Evelyn Mei Huang
*Attorney, Agent, or Firm*—Wenderoth, Lind & Ponack, L.L.P.

[57] ABSTRACT

Benzamide compounds of the formula

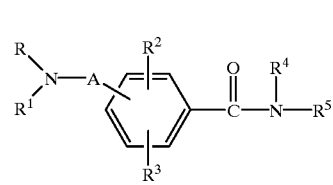

(I)

wherein each symbol is defined in the specification, isomers thereof and pharmaceutically acceptable acid addition salts thereof. Pharmaceutical compositions comprising a therapeutically effective amount of this compound and a pharmaceutically acceptable additive, and therapeutic agents for hypertension, therapeutic agents for angina pectoris, therapeutic agent for asthma, therapeutic agents for renal and peripheral circulatory disturbances and inhibitor of cerebral vasospasm, which comprise this compound. The compound of the present invention has strong smooth muscle relaxing action, and shows hypertensive action and cerebral•coronary vasodilating action like conventional calcium antagonists, as well as long-lasting renal and peripheral circulation improving action. Unlike calcium antagonists, it permits oral administration to suppress vascular contraction caused by various agonists, and is useful as a strong and long-acting agent for prophylaxis and treatment of circulatory diseases in coronary, cerebral, renal and peripheral arteries, as a therapeutic agent for hypertension, angina pectoris, and renal and peripheral circulation disorder, an inhibitor of cerebral vasospasm and the like. Moreover, the compound of the present invention is useful as a therapeutic agent for asthma.

16 Claims, No Drawings

BENZAMIDE COMPOUNDS AND PHARMACEUTICAL USE THEREOF

This application is a divisional of Ser. No. 08/727,669 filed Oct. 17, 1996, which is a 371 of PCT/JP95/00747 filed Apr. 17, 1995, U.S. Pat. No. 5,958,944.

The present invention relates to novel benzamide compounds useful as pharmaceutical agents, isomers thereof, pharmaceutically acceptable acid addition salts thereof and pharmaceutical use thereof.

BACKGROUND OF THE INVENTION

One pathogenetic cause of hypertension and coronary•cerebral circulatory disturbances (e.g., angina pectoris, cerebral infarction and the like) which pose serious social problems as adult diseases is considered to be an abnormal contraction of smooth muscle. The contraction and relaxation of smooth muscle are mainly controlled by increase and decrease of intracellular calcium. The calcium which has flowed into smooth muscle cells binds with calmodulin to activate myosin light chain phosphorylation enzyme. As a result, myosin light chain is phosphorylated to cause contraction smooth muscles (myosin phosphorylation theory). Taking note of this theory, various calcium antagonists have been developed which reduce intracellular calcium and distend blood vessels, and widely used for the therapy of hypertension, angina pectoris and the like.

Inasmuch as a sustained contraction of smooth muscle of blood vessel, trachea and the like, which is characteristic of smooth muscle, is inexplicable by myosin phosphorylation theory alone, an involvement of contraction mechanism which is independent of intracellular calcium level, and calcium sensitivity reinforcing mechanism, have been suggested in recent years. Such involvement is supported by the occurrence of contraction of smooth muscle and diseases (e.g., cerebral vasospasm, asthma and the like) on which calcium antagonists are ineffective. Therefore, a pharmaceutical agent which only reduces intracellular calcium is insufficient to treat diseases caused by contraction of smooth muscle, and the development of a new smooth muscle relaxant has been awaited.

Benzamide compounds as cardiotonics have been reported in Japanese Patent Unexamined Publication Nos. 158252/1987 and 158253/1987; as antiulcer agents in J. Med. Chem., 14, 963 (1971); and as intestinal peristaltic movement inhibitors in Spanish patent No. 456,989. Yet, no reports have documented their smooth muscle relaxing action.

On the other hand, WO 93/05021 discloses that 4-amino (alkyl)-cyclohexane-1-carboxamide compounds are useful as potent and long-acting anti-hypertensive agents, agents for prevention and treatment of circulatory diseases of coronary, cerebral, renal and peripheral arteries, and therapeutic agents for asthma.

It is therefore an object of the present invention to provide an agent which can be administered orally, which has strong smooth muscle relaxing action, hypotensive action and cerebral•coronary vasodilating action like conventional calcium antagonists, as well as sustained renal and peripheral circulation improving action, and which also suppresses, unlike calcium antagonists, vasoconstriction caused by various agonists.

DISCLOSURE OF THE INVENTION

The present inventors have conducted intensive studies and found that the benzamide compounds of the present invention, isomers thereof and pharmaceutically acceptable acid addition salts thereof can accomplish the above-mentioned objects and completed the present invention.

It has been also found that the compound of the present invention has anti-asthma action based on the inhibitory action on experimental asthma in guinea pig which was induced by histamin inhalation, and on the inhibitory action on the contraction induced by acetylcholine in tracheal specimens extracted from guinea pig.

Thus, the present invention relates to benzamide compounds of the formula

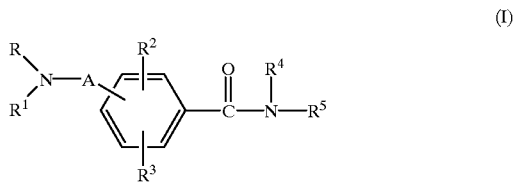

(I)

wherein
R is a hydrogen, an alkyl, or a cycloalkyl, a cycloalkylalkyl, a phenyl or an aralkyl, which optionally has a substituent on a ring, or a group of the formula

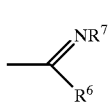

(II)

wherein $R^6$ is hydrogen, alkyl or the formula: —$NR^8R^9$
  wherein $R^8$ and $R^9$ are the same or different and
  each is hydrogen, alkyl, aralkyl or phenyl, and
  $R^7$ is hydrogen, alkyl, aralkyl, phenyl, nitro or cyano, or
    $R^6$ and $R^7$ combinedly form a heterocycle optionally
    having oxygen atom, sulfur atom or optionally substituted nitrogen atom additionally in the ring;
$R^1$ is a hydrogen, an alkyl, or a cycloalkyl, a cycloalkylalkyl, a phenyl or an aralkyl, which optionally has a substituent on a ring; or
R and $R^1$ combinedly form, together with the adjacent nitrogen atom, a heterocycle optionally having oxygen atom, sulfur atom or optionally substituted nitrogen atom additionally in the ring;
$R^2$ and $R^3$ are the same or different and each is a hydrogen, an alkyl, an aralkyl, a halogen, a nitro, an amino, analkylamino, an acylamino, a hydroxy, an alkoxy, an aralkyloxy, a cyano, an acyl, a mercapto, an alkylthio, an aralkylthio, a carboxy, an alkoxycarbonyl, a carbamoyl, an alkylcarbamoyl or an azide;
$R^4$ is a hydrogen or an alkyl;
$R^5$ is a heterocycle containing nitrogen, which is selected from the group consisting of pyridine, pyrimidine, pyridazine, triazine, pyrazole, triazole, pyrrolopyridine, pyrazolopyridine, imidazopyridine, pyrrolopyrimidine, pyrazolopyrimidine, imidazopyrimidine, pyrrolotriazine, pyrazolotriazine, triazolopyridine, triazolopyrimidine, cinnoline, quinazoline, quinoline, pyridopyridazine, pyridopyrazine, pyridopyrimidine, pyrimidopyrimidine, pyrazinopyrimidine, naphthylidine, tetrazolopyrimidine, thienopyridine, thienopyrimidine, thiazolopyridine, thiazolopyrimidine, oxazolopyridine, oxazolopyrimidine, furopyridine, furopyrimidine, 2,3-dihydropyrrolopyridine, 2,3-dihydropyrrolopyrimidine, 5,6,7,8-tetrahydropyrido-[2,3d]pyrimidine, 5,6,7,8-tetrahydro-1,8-naphthylidine and 5,6,7,8-tetrahydroquinoline, provided that when said heterocycle containing nitrogen forms a hydrogenated aromatic ring, carbon atom in the ring is optionally carbonyl, and said heterocycle containing nitrogen optionally has a substituent; and
A is the formula

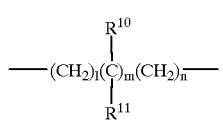

wherein $R^{10}$ and $R^{11}$ are the same or different and each is hydrogen, alkyl, haloalkyl, aralkyl, hydroxyalkyl, carboxy or alkoxycarbonyl, or $R^{10}$ and $R^{11}$ combinedly form cycloalkyl, and l, m and n are each 0 or an integer of 1–3, isomers thereof and pharmaceutically acceptable acid addition salts thereof.

The present invention further provides pharmaceutical compositions containing a therapeutically effective amount of the compound of formula (I), an isomer thereof or a pharmaceutically acceptable acid addition salt thereof, and a pharmaceutically acceptable additive; therapeutic agents for hypertension, angina pectoris, asthma, renal and peripheral circulation disorders, and cerebral vasospasm inhibitor containing a therapeutically effective amount of the compound of formula (I), an isomer thereof or a pharmaceutically acceptable acid addition salt thereof.

Each symbol in the present specification means the following.

Alkyl at R and $R^1$ is straight or branched alkyl having 1 to 6 carbon atoms, and exemplified by methyl, ethyl, propyl, isopropyl, butyl, isobutyl, sec-butyl, tert-butyl, pentyl, hexyl and the like, with preference given to alkyl having 1 to 4 carbon atoms.

Cycloalkyl at R and $R^1$ is cycloalkyl having 3 to 7 carbon atoms such as cyclopropyl, cyclobutyl, cyclopentyl, cyclohexyl and cycloheptyl.

Cycloalkylalkyl at R and $R^1$ is that having, as a cycloalkyl moiety, the aforementioned cycloalkyl having 3 to 7 carbon atoms and straight or branched alkyl having 1 to 6 carbon atoms (e.g., methyl, ethyl, propyl, isopropyl, butyl, pentyl and hexyl) as an alkyl moiety, and exemplified by cyclopropylmethyl, cyclobutylmethyl, cyclopentylmethyl, cyclohexylmethyl, cycloheptylmethyl, cyclopropylethyl, cyclopentylethyl, cyclohexylethyl, cycloheptylethyl, cyclopropylpropyl, cyclopentylpropyl, cyclohexylpropyl, cycloheptylpropyl, cyclopropylbutyl, cyclopentylbutyl, cyclohexylbutyl, cycloheptylbutyl, cyclopropylhexyl, cyclopentylhexyl, cyclohexylhexyl, cycloheptylhexyl and the like.

Aralkyl at R and $R^1$ is that having, as an alkyl moiety, alkyl having 1 to 4 carbon atoms, and is exemplified by phenylalkyl such as benzyl, 1-phenylethyl, 2-phenylethyl, 3-phenylpropyl and 4-phenylbutyl.

The substituent of cycloalkyl, cycloalkylalkyl, phenyl and aralkyl which may have substituent on the ring at R and $R^1$ is halogen (e.g., chlorine, bromine, fluorine and iodine), alkyl (same as alkyl at R and $R^1$), alkoxy (straight or branched alkoxy having 1 to 6 carbon atoms, such as methoxy, ethoxy, propoxy, isopropoxy, butoxy, isobutoxy, sec-butoxy, tert-butoxy, pentyloxy and hexyloxy), aralkyl (same as aralkyl at R and $R^1$), haloalkyl (alkyl at R and $R^1$ substituted by 1 to 5 halogen(s), such as fluoromethyl, difluoromethyl, trifluoromethyl, 2,2,2-trifluoroethyl and 2,2,3,3,3-pentafluoropropyl), nitro, amino, cyano, azide and the like.

The heterocycle formed by R and $R^1$ in combination together with the adjacent nitrogen atom, which optionally has oxygen atom, sulfur atom or optionally substituted nitrogen atom additionally in the ring is preferably 5 or 6-membered ring or a ring bonded thereto. Specific examples include 1-pyrrolidinyl, piperidino, 1-piperazinyl, morpholino, thiomorpholino, 1-imidazolyl, 2,3-dihydrothiazol-3-yl and the like. The substituent at optionally substituted nitrogen atoms is exemplified by alkyl, aralky, haloalkyl and the like, wherein alkyl, aralkyl and haloalkyl are the same as those defined for R and $R^1$.

Halogen, alkyl, alkoxy and aralkyl at $R^2$ and $R^3$ are the same as those exemplified for R and $R^1$.

Acyl at $R^2$ and $R^3$ is, for example, alkanoyl having 2 to 6 carbon atoms (e.g., acetyl, propionyl, butyryl, valeryl and pivaloyl), benzoyl, or phenylalkanoyl whose alkanoyl moiety has 2 to 4 carbon atoms (e.g., phenylacetyl, phenylpropionyl and phenylbutyryl).

Alkylamino at $R^2$ and $R^3$ is that having, at an alkyl moiety, straight or branched alkyl having 1 to 6 carbon atoms, and exemplified by methylamino, ethylamino, propylamino, isopropylamino, butylamino, isobutylamin, sec-butylamino, tert-butylamino, pentylamino, hexylamino and the like.

Acylamino at $R^2$ and $R^3$ is that having, as acyl, alkanoyl having 2 to 6 carbon atoms, benzyl, or phenylalkanoyl whose alkanoyl moiety has 2 to 4 carbon atoms, and exemplified by acetylamino, propionylamino, butyrylamino, valerylamino, pivaloylamino, benzoylamino, phenylacetylamino, phenylpropionylamino, phenylbutyrylamino and the like.

Alkylthio at $R^2$ and $R^3$ is that having, at an alkyl moiety, straight or branched alkyl having 1 to 6 carbon atoms, and exemplified by methylthio, ethylthio, propylthio, isopropylthio, butylthio, isobutylthio, sec-butylthio, tert-butylthio, pentylthio, hexylthio and the like.

Aralkyloxy at $R^2$ $R^3$ is that including aralkyl having, as an alkyl moiety, alkyl having 1 to 4 carbon atoms, and exemplified by benzyloxy, 1-phenylethyloxy, 2-phenylethyloxy, 3-phenylpropyloxy, 4-phenylbutyloxy and the like.

Aralkylthio at $R^2$ and $R^3$ is that including aralkyl having, as an alkyl moiety, alkyl having 1 to 4 carbon atoms, and exemplified by benzylthio, 1-phenylethylthio, 2-phenylethylthio, 3-phenylpropylthio, 4-phenylbutylthio and the like.

Alkoxycarbonyl at $R^2$ and $R^3$ is that having, at an alkoxy moiety, straight or branched alkoxy having 1 to 6 carbon atoms, and exemplified by methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, hexyloxycarbonyl and the like.

Alkylcarbamoyl at $R^2$ and $R^3$ is carbamoyl mono- or di-substituted by alkyl having 1 to 4 carbon atoms, and exemplified by methylcarbamoyl, dimethylcarbamoyl, ethylcarbamoyl, diethylcarbamoyl, propylcarbamoyl, dipropylcarbamoyl, butylcarbamoyl, dibutylcarbamoyl, and the like.

Alkyl at $R^4$ is the same as alkyl at R and $R^1$.

Heterocycle containing nitrogen at $R^5$ when it is a monocycle is, or example, pyridine, pyrimidine, pyridazine, triazine, pyrazole or triazole, and when it is a condensed ring, it is exemplified by pyrrolopyridine (e.g., 1H-pyrrolo[2,3-b]pyridine, 1H-pyrrolo[3,2-b]pyridine and 1H-pyrrolo[3,4-b]pyridine), pyrazolopyridine (e.g., 1H-pyrazolo[3,4-b]pyridine and 1H-pyrazolo[4,3-b]pyridine), imidazopyridine (e.g., 1H-imidazo[4,5-b]pyridine), pyrrolopyridmidine (e.g., 1H-pyrrolo[2,3d]pyrimidine), 1H-pyrrolo[3,2-d]pyrimidine and 1H-pyrrolo[3,4-d]pyrimidine), pyrazolopyrimidine (e.g., 1H-pyrazolo[3,4-d]pyrimidine, pyrazolo[1,5-a] pyrimidine and 1H-pyrazolo[4,3-d]pyrimidine), imidazopyrimidine (e.g., imidazo[1,2-a]pyrimidine and 1H-imidazo[4,5-d]pyrimidine), pyrrolotriazine (e.g., pyrrolo[1,2-a]-1,3,5-triazine and pyrrolo[2,1-f]-1,2,4-triazine), pyrazolotriazine (e.g., pyrazolo[1,5-a]-1,3,5-triazine), triazolopyridine (e.g., 1H-1,2,3-triazolo[4,5-b]pyridine), triazolopyrimidine (e.g., 1,2,4-triazolo[1,5-a]pyrimidine, 1,2,4-triazolo[4,3-a] pyrimidine and 1H-1,2,3-triazolo[4,5-d]pyrimidine), cinnoline, quinazoline, quinoline, pyridopyridazine (e.g., pyrido[2,3-c]pyridazine), pyridopyrazine (e.g., pyrido[2,3-b]pyrazine), pyridopyrimidine (e.g., pyrido[2,3-d] pyrimidine and pyrido[3,2-d]pyrimidine), pyrimidopyrimidine (e.g., pyrimido[4,5-d]pyrimidine and pyrimido[<b]old8 5,4-d]pyrimidine), pyrazinopyrimidine (e.g., pyrazino[2,3-d]pyrimidine), naphthylidine (e.g., 1,8-naphthylidine), tetrazolopyrimidine (e.g., tetrazolo[1,5a] pyrimidine), thienopyridine (e.g., thieno[2,3-b]pyridine), thienopyrimidine (e.g., thieno[2,3-d]pyrimidine), thiazolopyridine (e.g., thiazolo[4,5-b]pyridine and thiazolo[5,4-b] pyridine), thiazolopyrimidine (e.g., thiazolo[4,5-d] pyrimidine and thiazolo[5,4-d]pyrimidine), oxazolopyridine (e.g., oxazolo[4,5-b]pyridine and oxazolo[5,4-b]pyridine, oxazolopyrimidine (e.g., oxazolo[4,5-d]pyrimidine and oxazolo[5,4-d]pyrimidine), furopyridine (e.g., furo[2,3-b] pyridine and furo[3,2-b]pyridine), furopyrimidine (e.g., furo [2,3-d]pyrimidine and furo[3,2-d]pyrimidine), 2,3-dihydropyrrolopyridine (e.g., 2,3-dihydro-1H-pyrrolo[2,3-b]pyridine and 2,3-dihydro-1H-pyrrolo[3,2-b]pyridine), 2,3-dihydropyrrolopyrimidine (e.g., 2,3-dihydro-1H-pyrrolo[2,3-d]pyrimidine and 2,3-dihydro-1H-pyrrolo[3,2-d] pyrimidine), 5,6,7,8-tetrahydropyrido[2,3-d]pyrimidine, 5,6,7,8-tetrahydro-1,8-naphthylidine, 5,6,7,8-tetrahydroquinoline and the like. When these rings form hydrogenated aromatic rings, the carbon atom in the ring may be carbonyl, Examples thereof include 2,3-dihydro-1-oxopyrrolopyridine, 2,3-dihydro-2,3-dioxopyrrolopyridine, 7,8-dihydro-7-oxo-1,8-naphthylidine, 5,6,7,8-tetrahydro-7-oxo-1,8-naphthylidine and the like.

These rings may be substituted by substituent such as halogen, alkyl, alkoxy, aralkyl, haloalkyl, nitro, amino, alkylamino, cyano, formyl, acyl, aminoalkyl, mono- or dialkylaminoalkyl, azide, carboxy, alkoxycarbonyl, carbamoyl, alkylcarbamoyl, optionally substituted hydrazino and the like.

The substituent of optionally substituted hydrazino include, for example, alkyl, aralkyl, nitro and cyano, wherein alkyl and aralkyl are the same as alkyl and aralkyl at R and $R^1$, and optionally substituted hydrazino is exemplified by methylhydrazino, ethylhydrazino, benzylhydrazino, and the like.

Aklyl at $R^6$ is the same as alkyl at R and $R^1$; alkyl at $R^8$, $R^9$, $R^{8a}$, $R^{9a}$, $R^{8b}$ and $R^{9b}$ is the same as alkyl at R and $R^1$; and aralkyl at $R^8$, $R^9$, $R^{8a}$ and $R^{9a}$ is the same as aralkyl at R and $R^1$.

Alkyl at $R^7$, $R^{7a}$ and $R^{7b}$ is the same as alkyl at R and $R^1$, and aralkyl at $R^7$ and $R^{7a}$ is the same as alkyl at R and $R^1$.

The group formed combinedly by $R^6$ and $R^7$, $R^{6a}$ and $R^{7a}$, and $R^{6b}$ and $R^{7b}$, or $R^{6c}$ and $R^{7c}$, which forms a heterocycle optionally having oxygen atom, sulfur atom or optionally substituted nitrogen atom additionally in the ring may be, for example, imidazol-2-yl, thiazol-2-yl, oxazol-2-yl, imidazolin-2-yl, 3,4,5,6-tetrahydropyridin-2-yl, 3,4,5,6-tetrahydropyrimidin-2-yl, 1,3-oxazolin-2-yl, 1,3-thiazolin-2-yl, or benzimidazol-2-yl, benzothiazol-2-yl or benzoxazol-2-yl which may have substituent such as halogen, alkyl, alkoxy, haloalkyl, nitro, amino, phenyl, aralkyl and the like. By halogen, alkyl, alkoxy, haloalkyl and aralky are meant those exemplified for R and $R^1$.

The substituent of the above-mentioned optionally substituted nitrogen atom may be, for example, alkyl, aralkyl or haloalkyl, wherein alkyl, aralkyl and haloalkyl are those exemplified for R and $R^1$.

Hydroxyalkyl at $R^{10}$, $R^{11}$, $R^{10a}$, $R^{11a}$, $R^{10b}$ and $R^{11b}$ is straight or branched alkyl having 1 to 6 carbon atoms, which is substituted by 1 to 3 hydroxy, such as hydroxymethyl, 2-hydroxyethyl, 1-hydroxyethyl, 3-hydroxypropyl and 4-hydroxybutyl. Alkyl at $R^{10}$, $R^{11}$, $R^{10a}$, $R^{11a}$, $R^{10b}$ and $R^{11b}$ is the same as those at R and $R^1$; haloalkyl and alkoxycarbonyl at $R^{10}$, $R^{11}$, $R^{10a}$ and $R^{11a}$ are the same as those at R and $R^1$; and aralkyl at $R^{10}$ and $R^{11}$ is the same as those at R and $R^1$. Cycloalkyl combinedly formed by $R^{10}$ and $R^{11}$, $R^{10a}$ and $R^{11a}$ or $R^{10b}$ and $R^{11b}$ is the same as cycloalkyl at R and $R^1$.

The present invention includes pharmaceutically acceptable acid addition salts formed with compound (I) and inorganic acid or organic acid, hydrates and various solvates. When the compound has a carboxyl group, metal salts such as sodium salt, potassium salt, calcium salt, aluminun salt and the like, and salts with amino acid such as lysine, ornithine and the like are included.

When the compound of the present invention has asymmetric carbon, optical isomers and racemates thereof may be present, which are all encompassed in the present invention.

(1) In the present invention, it is preferable that, in formula (I), at least one of R, $R^1$, $R^2$, $R^3$, $R^4$, $R^5$ and A satisfy the following definition:

R is hydrogen, alkyl, or aralkyl optionally having substituent on the ring, or the formula

(II')

wherein $R^{6a}$ is hydrogen or the formula: —$NR^{8a}R^{9a}$ wherein $R^{8a}$ and $R^{9a}$ are the same or different and each is hydrogen, alkyl or aralkyl, and $R^{7a}$ is hydrogen, alkyl, aralkyl or phenyl, or $R^{6a}$ and $R^{7a}$ combinedly form a heterocycle optionally having oxygen atom, sulfur atom or optionally substituted nitrogen atom additionally in the ring. $R^1$ is hydrogen, alkyl, or cycloalkyl, cycloalkylalkyl, phenyl or aralkyl, which optionally has a substituent on the ring. Alternatively, R and $R^1$ combinedly form, together with the adjacent nitrogen atom, a heterocycle optionally having oxygen atom, sulfur atom or optionally substituted nitrogen atom additionally in the ring.

$R^2$ and $R^3$ are the same or different and each is hydrogen, alkyl, halogen, nitro, amino, hydroxy, alkoxy, aralkyloxy, cyano, acyl, carboxy, alkoxycarbonyl, carbamoyl or azide.

$R^4$ is hydrogen or alkyl.

$R^5$ is a heterocycle containing nitrogen, which is selected from the group consisting of pyridine, pyrimidine, pyridazine, triazine, pyrazole, triazole, pyrrolopyridine, pyrazolopyridine, imidazopyridine, pyrrolopyrimidine, pyrazolopyrimidine, imidazopyrimidine, pyrrolotriazine, pyrazolotriazine, triazolopyridine, triazolopyrimidine, cinnoline, quinazoline, quinoline, pyridopyridazine, pyridopyrazine, pyridopyrimidine, pyrimidopyrimidine, pyrazinopyrimidine, naphthylidine, tetrazolopyrimidine, thienopyridine, thienopyrimidine, thiazolopyridine, thiazolopyrimidine, oxazolopyridine, oxazolopyrimidine, furopyridine, furopyrimidine, 2,3-dihydro-pyrrolopyridine, 2,3-dihydropyrrolopyrimidine, 5,6,7,8-tetrahydro-pyrido[2,3-d]pyrimidine, 5,6,7,8-tetrahydro-1,8-naphthylidine and 5,6,7,8-tetrahydroquinoline, provided that when said heterocycle containing nitrogen forms a hydrogenated aromatic ring, carbon atom in the ring is optionally carbonyl, and said heterocycle containing nitrogen optionally has a substituent. A is the formula

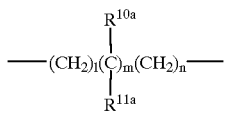

(III′)

wherein $R^{10a}$ and $R^{11a}$ are the same or different and each is hydrogen, alkyl, haloalkyl, hydroxyalkyl, carboxy or alkoxycarbonyl, or $R^{10a}$ and $R^{11a}$ combinedly form cycloalkyl, and l, m and n are each 0 or an integer of 1 to 3.
(2) In the present invention, it is particularly preferable that, in formula (I), at least one of R, $R^1$, $R^2$, $R^3$, $R^4$, $R^5$ and A satisfy the following definition:
R is hydrogen or alkyl or the formula

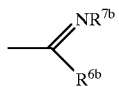

(II″)

wherein $R^{6b}$ is hydrogen or the formula: $—NR^{8b}R^{9b}$ wherein $R^{8b}$ and $R^{9b}$ are the same or different and each is hydrogen or alkyl, and $R^{7b}$ is hydrogen or alkyl, or $R^{6b}$ and $R^{7b}$ combinedly form a heterocycle optionally having optionally substituted nitrogen atom additionally in the ring.
$R^1$ is hydrogen or alkyl, or R and $R^1$ combinedly form, together with the adjacent nitrogen atom, a heterocycle optionally having optionally substituted nitrogen atom additionally in the ring.
$R^2$ $R^3$ are the same or different and each is hydrogen, halogen, nitro, hydroxy, aralkyloxy, cyano, carboxy, alkoxycarbonyl, carbamoyl or azide.
$R^4$ is hydrogen.
$R^5$ is a group derived from optionally substituted pyridine, 1H-pyrrolo[2,3-b]pyridine or 1H-pyrazolo[3,4-b]pyridine.
A is the formula

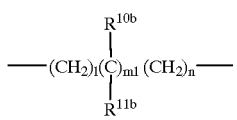

(III″)

wherein $R^{10b}$ and $R^{11b}$ are the same or different and each is hydrogen, alkyl, hydroxyalkyl or carboxy, or $R^{10b}$ $R^{11b}$ combinedly form cycloalkyl, l and n are each 0 or an integer of 1–3, and $m^1$ is 0 or 1.
(3) Preferably, in the formula (I), the group represented by $—NRR^1$ is amino, guanidino or 3-propylguanidino; $R^2$ and $R^3$ are the same or different and each is hydrogen, halogen, nitro, cyanol or azide; $R^4$ is hydrogen; $R^5$ is optionally substituted 4-pyridyl, 1H-pyrrolo[2,3-b]pyridin-4-yl or 1H-pyrazolo[3,4-b]pyridin-4-yl; and A is —$CH_2$—, —CH($CH_3$)—, —C($CH_3$)$_2$— or —CH($CH_2OH$)—.
A is preferably bonded at the 4-position of benzamide.

In the formula (I), when A has an asymmetric carbon as in the formula —CH($CH_3$)—, a compound wherein its absolute configuration is R shows preferable activity.

Of the compounds of formula (I), preferred are among the following compounds.

(R)-N-(4-pyridyl)-4-(1-aminoethyl)benzamide, (R)-N-(4-pyridyl)-4-(1-aminoethyl)-3-nitrobenzamide, (R)-N-(4-pyridyl)-4-(1-aminoehtyl)-3-chlorobenzamide, (R)-N-(4-pyridyl)-4-(1-aminoethyl)-2-nitrobenzamide, (R)-N-(4-pyridyl)-4-(1-aminoethyl)-2-chlorobenzamide, (R)-N-(1H-pyrrolo[2,3-b]pyridin-4-yl)-4-(1-aminoethyl)benzamide, (R)-N-(1H-pyrrolo[2,3-b]pyridin-4-yl)-4-(1-aminoethyl)-3-azide-benzamide, (R)-N-(1H-pyrrolo[2,3-b]-4-yl)-4-(1-aminoethyl)-3-azide-benzamide, (R)-N-(3-iodo-1H-pyrrolo[2,3-b]pyridin-4-yl)-4-(1-aminoethyl)-3-azidebenzamide, (R)-N-(1H-pyrazolo[3,4-b]pyridin-4-yl)-4-(1-aminoethyl)benzamide, (R)-N-(1H-pyrazolo[3,4-b]pyridin-4-yl)-4-(1-aminoethyl-3-nitro-benzamide, (R)-N-(1h-pyrazolo[3,4-b]pyridin-4-yl)-4-(1-aminoethyl)-2-nitro-benzamide, (R)-N-(1H-pyrazolo[3,4-b]pyridin-4-yl)-4-(1-aminoethyl)-3-azide-benzamide, (R)-N-(4-pyridyl)-4-(1-guanidinoethyl)benzamide, N-(1H-pyrazolo[3,4-b]pyridin-4-yl)-4-guanidinomethylbenzamide, (R)-N-(1H-pyrazolo[3,4-b]pyridin-4-yl)-4-(1-guanidinoethyl)-benzamide, N-(1H-pyrazolo[3,4-b]pyridin-4-yl)-4-guanidinomethyl-3-nitro-benzamide, (R)-N-(1H-pyrazolo[3,4-b]pyridin-4-yl)-4-(1-guanidinoethyl)-3-nitrobenzamide, (R)-N-(1H-pyrazolo[3,4-b]pyridin-4-yl)-4-(1-guanidinoethyl)-2-nitro benzamide, (R)-N-(1H-pyrrolo[2,3-b]pyridin-4-yl)-4-(1-guanidinoethyl)-benzamide, (R)-N-(1H-pyrrolo[2,3-b]pyridin-4-yl-4-(1-(3-propylguanidino)-ethyl)benzamide, (R)-N-(1H-pyrazolo[3,4-b]pyridin-4-yl)-4-(1-aminoethyl)-3-cyano-benzamide, N-(1H-pyrazolo[3,4-b]pyridin-4-yl)-4-(1-amino-2hydroxyethyl)-benzamide and (R)-N-(3-iodo-1H-pyrrolo[2,3-b]pyridine-4yl)-4-(1-aminoethyl)-benzamide.

The compound encompassed in the present invention are as shown in the following Tables, wherein Me is methyl, Et is ethyl, nPr is n-propyl, iosPr is isopropyl, nBu is n-butyl, isoBu is isobutyl, Pen is pentyl, Hex is hexyl, Ac is acetyl, Ph is phenyl, Bn is benzyl and Phenetyl is 2-phenylethyl.

TABLE 1

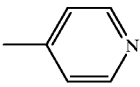

| number | RR¹N— | position of substitution | A | R² | R³ | R⁴ | R⁵ |
|---|---|---|---|---|---|---|---|
| 1 | $NH_2$ | 4 | —$CH_2$— | H | H | H |  |
| 2 | " | " | —CH(Me)— | " | " | " | " |
| 3 | " | " | —CH(Et)— | " | " | " | " |
| 4 | " | " | —CH(nPr)— | " | " | " | " |
| 5 | " | " | —CH(isoPr)— | " | " | " | " |
| 6 | " | " | —CH(nBu)— | " | " | " | " |
| 7 | " | " | —CH(isoBu)— | " | " | " | " |
| 8 | " | " | —CH($CH_2F$)— | " | " | " | " |
| 9 | " | " | —CH($CH_2CH_2F$)— | " | " | " | " |
| 10 | " | " | —CH($CHF_2$)— | " | " | " | " |
| 11 | " | " | —CH($CF_3$)— | " | " | " | " |
| 12 | " | " | —CH($CH_2CF_3$)— | " | " | " | " |
| 13 | " | " | —C(Me)$_2$— | " | " | " | " |
| 14 | " | " | —C(Et)$_2$— | " | " | " | " |
| 15 | " | " | —C(Pr)$_2$— | " | " | " | " |
| 16 | " | " |  | " | " | " | " |
| 17 | " | " | 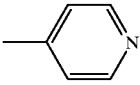 | " | " | " | " |
| 18 | " | " | —($CH_2$)$_2$— | " | " | " | " |
| 19 | " | " | —($CH_2$)$_3$— | " | " | " | " |
| 20 | " | " | —($CH_2$)$_4$— | " | " | " | " |

TABLE 2

| number | RR¹N— | position of substitution | A | R² | R³ | R⁴ | R⁵ |
|---|---|---|---|---|---|---|---|
| 21 | $NH_2$ | 3 | —$CH_2$— | H | H | H |  |
| 22 | " | " | —CH(Me)— | " | " | " | " |
| 23 | " | " | —CH(Et)— | " | " | " | " |
| 24 | " | " | —CH(nPr)— | " | " | " | " |
| 25 | " | " | —CH($CH_2F$)— | " | " | " | " |
| 26 | " | " | —CH($CF_3$)— | " | " | " | " |
| 27 | " | " | —C(Me)$_2$— | " | " | " | " |
| 28 | " | " | —C(Et)$_2$— | " | " | " | " |
| 29 | " | " |  | " | " | " | " |
| 30 | " | " |  | " | " | " | " |
| 31 | " | " | —($CH_2$)$_2$— | " | " | " | " |
| 32 | " | " | —($CH_2$)$_3$— | " | " | " | " |
| 33 | " | " | —$CH_2$— | " | " | " | " |

TABLE 2-continued

| number | RR¹N— | position of substitution | A | R² | R³ | R⁴ | R⁵ |
|---|---|---|---|---|---|---|---|
| 34 | " | " | —CH(Me)— | " | " | " | " |
| 35 | " | " | —CH(Et)— | " | " | " | " |
| 36 | " | " | —CH(nPr)— | " | " | " | " |
| 37 | " | " | —CH(CH₂F)— | " | " | " | " |
| 38 | " | " | —CH(CF₃)— | " | " | " | " |
| 39 | " | " | —C(Me)₂— | " | " | " | " |
| 40 | " | " | —C(Et)₂— | " | " | " | " |
| 41 | " | " | ▽ (cyclopropylidene) | " | " | " | " |
| 42 | " | " | ◇ (cyclobutylidene) | " | " | " | " |
| 43 | " | " | —(CH₂)₂— | " | " | " | " |
| 44 | " | " | —(CH₂)₃— | " | " | " | " |

TABLE 3

| number | RR¹N— | position of substitution | A | R² | R³ | R⁴ | R⁵ |
|---|---|---|---|---|---|---|---|
| 45 | NH₂ | 4 | —CH₂— | 3-OH | H | H | 4-pyridyl |
| 46 | " | " | " | 2-OH | " | " | " |
| 47 | " | " | " | 3-OMe | " | " | " |
| 48 | " | " | " | 2-OMe | " | " | " |
| 49 | " | " | " | 3-OEt | " | " | " |
| 50 | " | " | " | 2-OEt | " | " | " |
| 51 | " | " | " | 3-OBn | " | " | " |
| 52 | " | " | " | 2-OBn | " | " | " |
| 53 | " | " | " | 3-NO₂ | " | " | " |
| 54 | " | " | " | 2-NO₂ | " | " | " |
| 55 | " | " | " | 3-NH₂ | " | " | " |
| 56 | " | " | " | 2-NH₂ | " | " | " |
| 57 | " | " | " | 3-NHMe | " | " | " |
| 58 | " | " | " | 2-NHMe | " | " | " |
| 59 | " | " | " | 3-NHEt | " | " | " |
| 60 | " | " | " | 2-NHEt | " | " | " |
| 61 | " | " | " | 3-NHnPr | " | " | " |
| 62 | " | " | " | 2-NHnPr | " | " | " |
| 63 | " | " | " | 3-NMe₂ | " | " | " |
| 64 | " | " | " | 2-NMe₂ | " | " | " |
| 65 | " | " | " | 3-NHAc | " | " | " |
| 66 | " | " | " | 2-NHAc | " | " | " |
| 67 | " | " | " | 3-F | " | " | " |
| 68 | " | " | " | 2-F | " | " | " |

TABLE 4

| number | RR¹N— | position of substitution | A | R² | R³ | R⁴ | R⁵ |
|---|---|---|---|---|---|---|---|
| 69 | NH₂ | 4 | —CH₂— | 3-Cl | H | H | 4-pyridyl |
| 70 | " | " | " | 2-Cl | " | " | " |

TABLE 4-continued

| number | RR¹N— | position of substitution | A | R² | R³ | R⁴ | R⁵ |
|---|---|---|---|---|---|---|---|
| 71 | " | " | " | 3-Br | " | " | " |
| 72 | " | " | " | 2-Br | " | " | " |
| 73 | " | " | " | 3-CO₂H | " | " | " |
| 74 | " | " | " | 2-CO₂H | " | " | " |
| 75 | " | " | " | 3-CO₂Me | " | " | " |
| 76 | " | " | " | 2-CO₂Me | " | " | " |
| 77 | " | " | " | 3-CO₂Et | " | " | " |
| 78 | " | " | " | 2-CO₂Et | " | " | " |
| 79 | " | " | " | 3-CONH₂ | " | " | " |
| 80 | " | " | " | 2-CONH₂ | " | " | " |
| 81 | " | " | " | 3-CONHMe | " | " | " |
| 82 | " | " | " | 2-CONHMe | " | " | " |
| 83 | " | " | " | 3-CONHEt | " | " | " |
| 84 | " | " | " | 2-CONHEt | " | " | " |
| 85 | " | " | " | 3-COMe | " | " | " |
| 86 | " | " | " | 2-COMe | " | " | " |
| 87 | " | " | " | 3-COEt | " | " | " |
| 88 | " | " | " | 2-COEt | " | " | " |
| 89 | " | " | " | 3-COnPr | " | " | " |
| 90 | " | " | " | 2-COnPr | " | " | " |
| 91 | " | " | " | 3-Me | " | " | " |
| 92 | " | " | " | 2-Me | " | " | " |

TABLE 5

| number | RR¹N— | position of substitution | A | R² | R³ | R⁴ | R⁵ |
|---|---|---|---|---|---|---|---|
| 93 | NH₂ | 4 | —CH₂— | 3-Et | H | H | 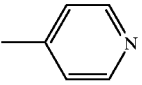 |
| 94 | " | " | " | 2-Et | " | " | " |
| 95 | " | " | " | 3-nPr | " | " | " |
| 96 | " | " | " | 2-nPr | " | " | " |
| 97 | " | " | " | 3-nBu | " | " | " |
| 98 | " | " | " | 2-nBu | " | " | " |
| 99 | " | " | " | 3-CN | " | " | " |
| 100 | " | " | " | 2-CN | " | " | " |
| 101 | " | " | " | 3-SMe | " | " | " |
| 102 | " | " | " | 2-SMe | " | " | " |
| 103 | " | " | " | 2-Me | 3-Me | " | " |
| 104 | " | " | " | 2-Me | 5-Me | " | " |
| 105 | " | " | " | 2-Me | 6-Me | " | " |
| 106 | " | " | " | 3-Me | 5-Me | " | " |
| 107 | " | " | " | 2-F | 3-F | " | " |
| 108 | " | " | " | 2-F | 5-F | " | " |
| 109 | " | " | " | 2-F | 6-F | " | " |
| 110 | " | " | " | 3-F | 5-F | " | " |
| 111 | " | " | " | 2-Cl | 3-Cl | " | " |
| 112 | " | " | " | 2-Cl | 5-Cl | " | " |
| 113 | " | " | " | 2-Cl | 6-Cl | " | " |
| 114 | " | " | " | 3-Cl | 5-Cl | " | " |
| 115 | " | " | " | 3-NH₂ | 5-NH₂ | " | " |
| 116 | " | " | " | 3-NO₂ | 5-NH₂ | " | " |

TABLE 6

| number | RR$^1$N— | position of substitution | A | R$^2$ | R$^3$ | R$^4$ | R$^5$ |
|---|---|---|---|---|---|---|---|
| 117 | NH$_2$ | 4 | —CH(Me)— | 3-OH | H | H | 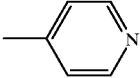 |
| 118 | " | " | " | 2-OH | " | " | " |
| 119 | " | " | " | 3-OMe | " | " | " |
| 120 | " | " | " | 2-OMe | " | " | " |
| 121 | " | " | " | 3-OEt | " | " | " |
| 122 | " | " | " | 2-OEt | " | " | " |
| 123 | " | " | " | 3-OBn | " | " | " |
| 124 | " | " | " | 2-OBn | " | " | " |
| 125 | " | " | " | 3-NO$_2$ | " | " | " |
| 126 | " | " | " | 2-NO$_2$ | " | " | " |
| 127 | " | " | " | 3-NH$_2$ | " | " | " |
| 128 | " | " | " | 2-NH$_2$ | " | " | " |
| 129 | " | " | " | 3-NHMe | " | " | " |
| 130 | " | " | " | 2-NHMe | " | " | " |
| 131 | " | " | " | 3-NHEt | " | " | " |
| 132 | " | " | " | 2-NHEt | " | " | " |
| 133 | " | " | " | 3-NHnPr | " | " | " |
| 134 | " | " | " | 2-NHnPr | " | " | " |
| 135 | " | " | " | 3-NMe$_2$ | " | " | " |
| 136 | " | " | " | 2-NMe$_2$ | " | " | " |
| 137 | " | " | " | 3-NHAc | " | " | " |
| 138 | " | " | " | 2-NHAc | " | " | " |
| 139 | " | " | " | 3-F | " | " | " |
| 140 | " | " | " | 2-F | " | " | " |

TABLE 7

| number | RR$^1$N— | position of substitution | A | R$^2$ | R$^3$ | R$^4$ | R$^5$ |
|---|---|---|---|---|---|---|---|
| 141 | NH$_2$ | 4 | —CH(Me)— | 3-Cl | H | H | 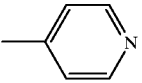 |
| 142 | " | " | " | 2-Cl | " | " | " |
| 143 | " | " | " | 3-Br | " | " | " |
| 144 | " | " | " | 2-Br | " | " | " |
| 145 | " | " | " | 3-CO$_2$H | " | " | " |
| 146 | " | " | " | 2-CO$_2$H | " | " | " |
| 147 | " | " | " | 3-CO$_2$Me | " | " | " |
| 148 | " | " | " | 2-CO$_2$Me | " | " | " |
| 149 | " | " | " | 3-CO$_2$Et | " | " | " |
| 150 | " | " | " | 2-CO$_2$Et | " | " | " |
| 151 | " | " | " | 3-CONH$_2$ | " | " | " |
| 152 | " | " | " | 2-CONH$_2$ | " | " | " |
| 153 | " | " | " | 3-CONHMe | " | " | " |
| 154 | " | " | " | 2-CONHMe | " | " | " |
| 155 | " | " | " | 3-CONHEt | " | " | " |
| 156 | " | " | " | 2-CONHEt | " | " | " |
| 157 | " | " | " | 3-COMe | " | " | " |
| 158 | " | " | " | 2-COMe | " | " | " |
| 159 | " | " | " | 3-COEt | " | " | " |
| 160 | " | " | " | 2-COEt | " | " | " |
| 161 | " | " | " | 3-COnPr | " | " | " |
| 162 | " | " | " | 2-COnPr | " | " | " |
| 163 | " | " | " | 3-Me | " | " | " |
| 164 | " | " | " | 2-Me | " | " | " |

TABLE 8

| number | RR$^1$N— | position of substitution | A | R$^2$ | R$^3$ | R$^4$ | R$^5$ |
|---|---|---|---|---|---|---|---|
| 165 | NH$_2$ | 4 | —CH(Me)— | 3-Et | H | H | 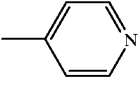 |
| 166 | " | " | " | 2-Et | " | " | " |
| 167 | " | " | " | 3-nPr | " | " | " |
| 168 | " | " | " | 2-nPr | " | " | " |
| 169 | " | " | " | 3-nBu | " | " | " |
| 170 | " | " | " | 2-nBu | " | " | " |
| 171 | " | " | " | 3-CN | " | " | " |
| 172 | " | " | " | 2-CN | " | " | " |
| 173 | " | " | " | 3-SMe | " | " | " |
| 174 | " | " | " | 2-SMe | " | " | " |
| 175 | " | " | " | 2-Me | 3-Me | " | " |
| 176 | " | " | " | 2-Me | 5-Me | " | " |
| 177 | " | " | " | 2-Me | 6-Me | " | " |
| 178 | " | " | " | 3-Me | 5-Me | " | " |
| 179 | " | " | " | 2-F | 3-F | " | " |
| 180 | " | " | " | 2-F | 5-F | " | " |
| 181 | " | " | " | 2-F | 6-F | " | " |
| 182 | " | " | " | 3-F | 5-F | " | " |
| 183 | " | " | " | 2-Cl | 3-Cl | " | " |
| 184 | " | " | " | 2-Cl | 5-Cl | " | " |
| 185 | " | " | " | 2-Cl | 6-Cl | " | " |
| 186 | " | " | " | 3-Cl | 5-Cl | " | " |
| 187 | " | " | " | 3-NH$_2$ | 5-NH$_2$ | " | " |
| 188 | " | " | " | 3-NO$_2$ | 5-NH$_2$ | " | " |

TABLE 9

| number | RR$^1$N— | position of substitution | A | R$^2$ | R$^3$ | R$^4$ | R$^5$ |
|---|---|---|---|---|---|---|---|
| 189 | NH$_2$ | 4 | —CH$_2$— | H | H | H | 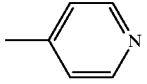 |
| 190 | " | " | " | " | " | " | 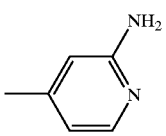 |
| 191 | " | " | " | " | " | " | 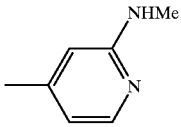 |
| 192 | " | " | " | " | " | " | 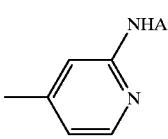 |
| 193 | " | " | " | " | " | " | 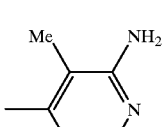 |

TABLE 9-continued
| number | RR¹N— | position of substitution | A | R² | R³ | R⁴ | R⁵ |
|---|---|---|---|---|---|---|---|
| 194 | " | " | " | " | " | " | 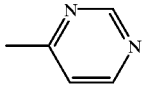 |
| 195 | " | " | " | " | " | " | 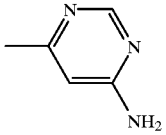 |
| 196 | " | " | " | " | " | " | 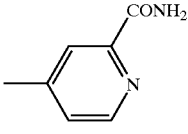 |
| 197 | " | " | " | " | " | " | 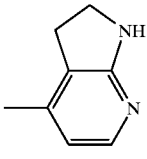 |
| 198 | " | " | " | " | " | " | 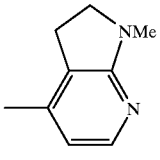 |
| 199 | " | " | " | " | " | " | 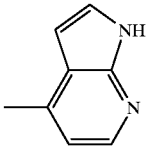 |
| 200 | " | " | " | " | " | " | 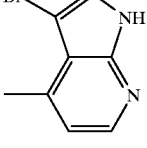 |
| 201 | " | " | " | " | " | " | 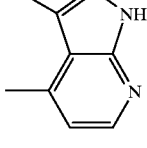 |
| 202 | " | " | " | " | " | " | 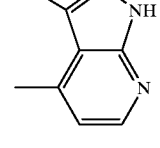 |

TABLE 9-continued

| number | RR¹N— | position of substitution | A | R² | R³ | R⁴ | R⁵ |
|---|---|---|---|---|---|---|---|
| 203 | " | " | " | " | " | " | MeO₂C-substituted pyrrolo[3,2-b]pyridine (4-Me, NH) |
| 204 | " | " | " | " | " | " | 2,3-diMe-pyrrolo[3,2-b]pyridine (4-Me, NH) |

TABLE 10

| number | RR¹N— | position of substitution | A | R² | R³ | R⁴ | R⁵ |
|---|---|---|---|---|---|---|---|
| 205 | NH₂ | 4 | —CH₂— | H | H | H | pyrazolo[3,4-d]pyrimidine (4-Me, 1H) |
| 206 | " | " | " | " | " | " | pyrazolo[3,4-b]pyridine (4-Me, 1H) |
| 207 | " | " | " | " | " | " | 1-Me-pyrazolo[3,4-b]pyridine (4-Me) |
| 208 | " | " | " | " | " | " | 3-Me-pyrazolo[3,4-b]pyridine (4-Me, 1H) |
| 209 | " | " | " | " | " | " | pyrrolo[2,3-d]pyrimidine (4-Me, 7H) |

TABLE 10-continued
| number | RR¹N— | position of substitution | A | R² | R³ | R⁴ | R⁵ |
|---|---|---|---|---|---|---|---|
| 210 | " | " | " | " | " | " | 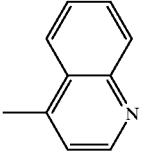 |
| 212 | " | " | " | " | " | " | 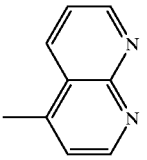 |
| 213 | " | " | " | " | " | " | 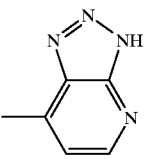 |
| 214 | " | " | " | " | " | " | 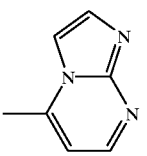 |
| 215 | " | " | " | " | " | " | 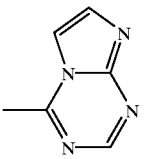 |
| 216 | " | " | " | " | " | " | 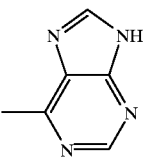 |
| 217 | " | " | " | " | " | " | 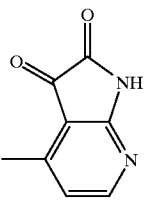 |
| 218 | " | " | " | " | " | " | 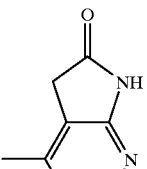 |

TABLE 10-continued

| number | RR¹N— | position of substitution | A | R² | R³ | R⁴ | R⁵ |
|---|---|---|---|---|---|---|---|
| 219 | " | " | " | " | " | " | ![pyrazolopyridinone structure] |

TABLE 11

| number | RR¹N— | position of substitution | A | R² | R³ | R⁴ | R⁵ |
|---|---|---|---|---|---|---|---|
| 220 | NH₂ | 4 | —CH(Me)— | H | H | H | 4-pyridyl |
| 221 | " | " | " | " | " | " | 2-amino-4-pyridyl |
| 222 | " | " | " | " | " | " | 2-(NHMe)-4-pyridyl |
| 223 | " | " | " | " | " | " | 2-(NHAc)-4-pyridyl |
| 224 | " | " | " | " | " | " | 2-amino-3-methyl-4-pyridyl |
| 225 | " | " | " | " | " | " | pyrimidin-4-yl |
| 226 | " | " | " | " | " | " | 6-amino-pyrimidin-4-yl |
| 227 | " | " | " | " | " | " | 2-carbamoyl-4-pyridyl |

TABLE 11-continued
| number | RR¹N— | position of substitution | A | R² | R³ | R⁴ | R⁵ |
|---|---|---|---|---|---|---|---|
| 228 | " | " | " | " | " | " | 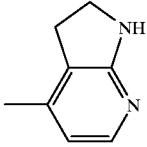 |
| 229 | " | " | " | " | " | " | 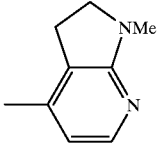 |
| 230 | " | " | " | " | " | " | 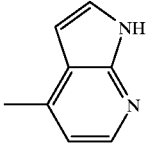 |
| 231 | " | " | " | " | " | " | 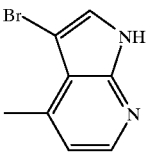 |
| 232 | " | " | " | " | " | " | 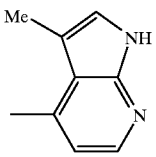 |
| 234 | " | " | " | " | " | " | 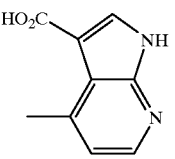 |
| 235 | " | " | " | " | " | " | 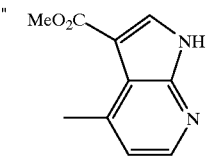 |
| 236 | " | " | " | " | " | " | 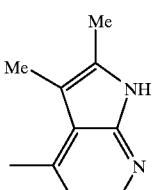 |

TABLE 12

| number | RR¹N— | position of substitution | A | R² | R³ | R⁴ | R⁵ |
|---|---|---|---|---|---|---|---|
| 237 | NH₂ | 4 | —CH(Me)— | H | H | H | pyrazolo[3,4-d]pyrimidin-4-yl (NH) |
| 238 | " | " | " | " | " | " | pyrazolo[3,4-b]pyridin-4-yl (NH) |
| 239 | " | " | " | " | " | " | 1-methylpyrazolo[3,4-b]pyridin-4-yl |
| 240 | " | " | " | " | " | " | 3-methylpyrazolo[3,4-b]pyridin-4-yl (NH) |
| 241 | " | " | " | " | " | " | pyrrolo[2,3-d]pyrimidin-4-yl (NH) |
| 242 | " | " | " | " | " | " | quinolin-4-yl |
| 243 | " | " | " | " | " | " | 1,8-naphthyridin-4-yl |
| 244 | " | " | " | " | " | " | triazolo[4,5-b]pyridin-4-yl (NH) |

TABLE 12-continued
| number | RR¹N— | position of substitution | A | R² | R³ | R⁴ | R⁵ |
|---|---|---|---|---|---|---|---|
| 245 | " | " | " | " | " | " | 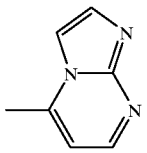 |
| 246 | " | " | " | " | " | " | 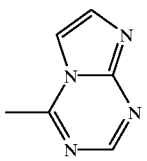 |
| 247 | " | " | " | " | " | " | 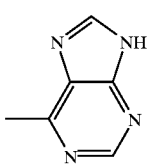 |
| 248 | " | " | " | " | " | " | 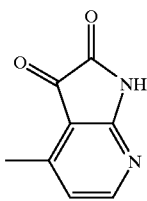 |
| 249 | " | " | " | " | " | " | 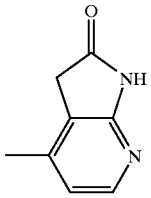 |
| 250 | " | " | " | " | " | " | 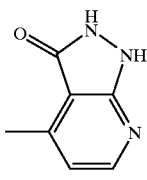 |
TABLE 13
| number | RR¹N— | position of substitution | A | R² | R³ | R⁴ | R⁵ |
|---|---|---|---|---|---|---|---|
| 251 | NH₂ | 4 | —CH₂— | 3-OH | H | H | 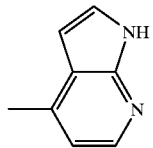 |

TABLE 13-continued

| number | RR¹N— | position of substitution | A | R² | R³ | R⁴ | R⁵ |
|---|---|---|---|---|---|---|---|
| 252 | " | " | " | 2-OH | " | " | " |
| 253 | " | " | " | 3-OMe | " | " | " |
| 254 | " | " | " | 2-OMe | " | " | " |
| 255 | " | " | " | 3-OBn | " | " | " |
| 256 | " | " | " | 2-OBn | " | " | " |
| 257 | " | " | " | 3-F | " | " | " |
| 258 | " | " | " | 2-F | " | " | " |
| 259 | " | " | " | 3-Cl | " | " | " |
| 260 | " | " | " | 2-Cl | " | " | " |
| 261 | " | " | " | 3-Br | " | " | " |
| 262 | " | " | " | 2-Br | " | " | " |
| 263 | " | " | " | 3-NO$_2$ | " | " | " |
| 264 | " | " | " | 2-NO$_2$ | " | " | " |
| 265 | " | " | " | 3-NH$_2$ | " | " | " |
| 266 | " | " | " | 2-NH$_2$ | " | " | " |
| 267 | " | " | " | 3-NHMe | " | " | " |
| 268 | " | " | " | 2-NHMe | " | " | " |
| 269 | " | " | " | 3-NMe$_2$ | " | " | " |
| 270 | " | " | " | 2-NMe$_2$ | " | " | " |
| 271 | " | " | " | 3-NHAc | " | " | " |
| 272 | " | " | " | 2-NHAc | " | " | " |
| 273 | " | " | " | 3-CO$_2$H | " | " | " |
| 274 | " | " | " | 2-CO$_2$H | " | " | " |

TABLE 14

| number | RR¹N— | position of substitution | A | R² | R³ | R⁴ | R⁵ |
|---|---|---|---|---|---|---|---|
| 275 | NH$_2$ | 4 | —CH$_2$— | 3-CO$_2$Me | H | H | 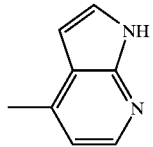 |
| 276 | " | " | " | 2-CO$_2$Me | " | " | " |
| 277 | " | " | " | 3-CO$_2$Et | " | " | " |
| 278 | " | " | " | 2-CO$_2$Et | " | " | " |
| 279 | " | " | " | 3-CONH$_2$ | " | " | " |
| 280 | " | " | " | 2-CONH$_2$ | " | " | " |
| 281 | " | " | " | 3-CONHMe | " | " | " |
| 282 | " | " | " | 2-CONHMe | " | " | " |
| 283 | " | " | " | 3-COMe | " | " | " |
| 284 | " | " | " | 2-COMe | " | " | " |
| 285 | " | " | " | 3-COEt | " | " | " |
| 286 | " | " | " | 2-COEt | " | " | " |
| 287 | " | " | " | 3-COnPr | " | " | " |
| 288 | " | " | " | 2-COnPr | " | " | " |
| 289 | " | " | " | 3-Me | " | " | " |
| 290 | " | " | " | 2-Me | " | " | " |
| 291 | " | " | " | 3-Et | " | " | " |
| 292 | " | " | " | 2-Et | " | " | " |
| 293 | " | " | " | 3-nPr | " | " | " |
| 294 | " | " | " | 2-nPr | " | " | " |
| 295 | " | " | " | 3-CN | " | " | " |
| 296 | " | " | " | 2-CN | " | " | " |
| 297 | " | " | " | 3-SMe | " | " | " |
| 298 | " | " | " | 2-SMe | " | " | " |

TABLE 15

| number | RR$^1$N— | position of substitution | A | R$^2$ | R$^3$ | R$^4$ | R$^5$ |
|---|---|---|---|---|---|---|---|
| 299 | NH$_2$ | 4 | —CH(Me)— | 3-OH | H | H | 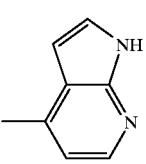 |
| 300 | " | " | " | 2-OH | " | " | " |
| 301 | " | " | " | 3-OMe | " | " | " |
| 302 | " | " | " | 2-OMe | " | " | " |
| 303 | " | " | " | 3-OBn | " | " | " |
| 304 | " | " | " | 2-OBn | " | " | " |
| 305 | " | " | " | 3-F | " | " | " |
| 306 | " | " | " | 2-F | " | " | " |
| 307 | " | " | " | 3-Cl | " | " | " |
| 308 | " | " | " | 2-Cl | " | " | " |
| 309 | " | " | " | 3-Br | " | " | " |
| 310 | " | " | " | 2-Br | " | " | " |
| 311 | " | " | " | 3-NO$_2$ | " | " | " |
| 312 | " | " | " | 2-NO$_2$ | " | " | " |
| 313 | " | " | " | 3-NH$_2$ | " | " | " |
| 314 | " | " | " | 2-NH$_2$ | " | " | " |
| 315 | " | " | " | 3-NHMe | " | " | " |
| 316 | " | " | " | 2-NHMe | " | " | " |
| 317 | " | " | " | 3-NMe$_2$ | " | " | " |
| 318 | " | " | " | 2-NMe$_2$ | " | " | " |
| 319 | " | " | " | 3-NHAc | " | " | " |
| 320 | " | " | " | 2-NHAc | " | " | " |
| 321 | " | " | " | 3-CO$_2$H | " | " | " |
| 322 | " | " | " | 2-CO$_2$H | " | " | " |

TABLE 16

| number | RR$^1$N— | position of substitution | A | R$^2$ | R$^3$ | R$^4$ | R$^5$ |
|---|---|---|---|---|---|---|---|
| 323 | NH$_2$ | 4 | —CH(Me)— | 3-CO$_2$Me | H | H | 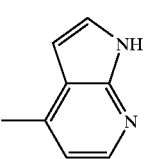 |
| 324 | " | " | " | 2-CO$_2$Me | " | " | " |
| 325 | " | " | " | 3-CO$_2$Et | " | " | " |
| 326 | " | " | " | 2-CO$_2$Et | " | " | " |
| 327 | " | " | " | 3-CONH$_2$ | " | " | " |
| 328 | " | " | " | 2-CONH$_2$ | " | " | " |
| 329 | " | " | " | 3-CONHMe | " | " | " |
| 330 | " | " | " | 2-CONHMe | " | " | " |
| 331 | " | " | " | 3-COMe | " | " | " |
| 332 | " | " | " | 2-COMe | " | " | " |
| 333 | " | " | " | 3-COEt | " | " | " |
| 334 | " | " | " | 2-COEt | " | " | " |
| 335 | " | " | " | 3-COnPr | " | " | " |
| 336 | " | " | " | 2-COnPr | " | " | " |
| 337 | " | " | " | 3-Me | " | " | " |
| 338 | " | " | " | 2-Me | " | " | " |
| 339 | " | " | " | 3-Et | " | " | " |
| 340 | " | " | " | 2-Et | " | " | " |
| 341 | " | " | " | 3-nPr | " | " | " |
| 342 | " | " | " | 2-nPr | " | " | " |
| 343 | " | " | " | 3-CN | " | " | " |
| 344 | " | " | " | 2-CN | " | " | " |
| 345 | " | " | " | 3-SMe | " | " | " |
| 346 | " | " | " | 2-SMe | " | " | " |

TABLE 17

| number | RR¹N— | position of substitution | A | R² | R³ | R⁴ | R⁵ |
|---|---|---|---|---|---|---|---|
| 347 | NH₂ | 4 | —CH(Me)— | 3-OH | H | H | 4-methyl-1H-pyrazolo[3,4-b]pyridin-yl |
| 348 | " | " | " | 2-OH | " | " | " |
| 349 | " | " | " | 3-OMe | " | " | " |
| 350 | " | " | " | 2-OMe | " | " | " |
| 351 | " | " | " | 3-OBn | " | " | " |
| 352 | " | " | " | 2-OBn | " | " | " |
| 353 | " | " | " | 3-F | " | " | " |
| 354 | " | " | " | 2-F | " | " | " |
| 355 | " | " | " | 3-Cl | " | " | " |
| 356 | " | " | " | 2-Cl | " | " | " |
| 357 | " | " | " | 3-Br | " | " | " |
| 358 | " | " | " | 2-Br | " | " | " |
| 359 | " | " | " | 3-NO₂ | " | " | " |
| 360 | " | " | " | 2-NO₂ | " | " | " |
| 361 | " | " | " | 3-NH₂ | " | " | " |
| 362 | " | " | " | 2-NH₂ | " | " | " |
| 363 | " | " | " | 3-NHMe | " | " | " |
| 364 | " | " | " | 2-NHMe | " | " | " |
| 365 | " | " | " | 3-NMe₂ | " | " | " |
| 366 | " | " | " | 2-NMe₂ | " | " | " |
| 367 | " | " | " | 3-NHAc | " | " | " |
| 368 | " | " | " | 2-NHAc | " | " | " |
| 369 | " | " | " | 3-CO₂H | " | " | " |
| 370 | " | " | " | 2-CO₂H | " | " | " |

TABLE 18

| number | RR¹N— | position of substitution | A | R² | R³ | R⁴ | R⁵ |
|---|---|---|---|---|---|---|---|
| 371 | NH₂ | 4 | —CH(Me)— | 3-CO₂Me | H | H | 4-methyl-1H-pyrazolo[3,4-b]pyridin-yl |
| 372 | " | " | " | 2-CO₂Me | " | " | " |
| 373 | " | " | " | 3-CO₂Et | " | " | " |
| 374 | " | " | " | 2-CO₂Et | " | " | " |
| 375 | " | " | " | 3-CONH₂ | " | " | " |
| 376 | " | " | " | 2-CONH₂ | " | " | " |
| 377 | " | " | " | 3-CONHMe | " | " | " |
| 378 | " | " | " | 2-CONHMe | " | " | " |
| 379 | " | " | " | 3-COMe | " | " | " |
| 380 | " | " | " | 2-COMe | " | " | " |
| 381 | " | " | " | 3-COEt | " | " | " |
| 382 | " | " | " | 2-COEt | " | " | " |
| 383 | " | " | " | 3-COnPr | " | " | " |
| 384 | " | " | " | 2-COnPr | " | " | " |
| 385 | " | " | " | 3-Me | " | " | " |
| 386 | " | " | " | 2-Me | " | " | " |
| 387 | " | " | " | 3-Et | " | " | " |
| 388 | " | " | " | 2-Et | " | " | " |
| 389 | " | " | " | 3-nPr | " | " | " |
| 390 | " | " | " | 2-nPr | " | " | " |
| 391 | " | " | " | 3-CN | " | " | " |
| 392 | " | " | " | 2-CN | " | " | " |
| 393 | " | " | " | 3-SMe | " | " | " |
| 394 | " | " | " | 2-SMe | " | " | " |

TABLE 19

| number | RR¹N— | position of substitution | A | R² | R³ | R⁴ | R⁵ |
|---|---|---|---|---|---|---|---|
| 395 | H₂N-C(=NH)-NH— | 4 | —CH₂— | H | H | H | 4-pyridyl |
| 396 | H₂N-C(=NH)-NH— | " | —CH(Me)— | " | " | " | " |
| 397 | MeNH-C(=NH)-NH— | " | " | " | " | " | " |
| 398 | EtNH-C(=NH)-NH— | " | " | " | " | " | " |
| 399 | PrNH-C(=NH)-NH— | " | " | " | " | " | " |
| 400 | BuNH-C(=NH)-NH— | " | " | " | " | " | " |
| 401 | PemNH-C(=NH)-NH— | " | " | " | " | " | " |
| 402 | PhNH-C(=NH)-NH— | " | " | " | " | " | " |
| 403 | BnNH-C(=NH)-NH— | " | " | " | " | " | " |
| 404 | PhenetylNH-C(=NH)-NH— | " | " | " | " | " | " |
| 405 | MeNH-C(=NMe)-NH— | " | " | " | " | " | " |
| 406 | EtNH-C(=NMe)-NH— | " | " | " | " | " | " |
| 407 | PrNH-C(=NMe)-NH— | " | " | " | " | " | " |
| 408 | H₂N-C(=NCN)-NH— | " | " | " | " | " | " |

TABLE 19-continued

| number | RR¹N— | position of substitution | A | R² | R³ | R⁴ | R⁵ |
|---|---|---|---|---|---|---|---|
| 409 | O₂NN=C(NH₂)—NH— | " | " | " | " | " | " |
| 410 | (4,5-dihydro-1H-imidazol-2-yl)—NH— | " | " | " | " | " | " |

TABLE 20

| number | RR¹N— | position of substitution | A | R² | R³ | R⁴ | R⁵ |
|---|---|---|---|---|---|---|---|
| 411 | (1,4,5,6-tetrahydropyrimidin-2-yl)—NH— | 4 | —CH(Me)— | H | H | H | 4-pyridyl |
| 412 | (1H-imidazol-2-yl)—NH— | " | " | " | " | " | " |
| 413 | (1H-1,2,4-triazol-3-yl)—NH— | " | " | " | " | " | " |
| 414 | (oxazol-2-yl)—NH— | " | " | " | " | " | " |
| 415 | (thiazol-2-yl)—NH— | " | " | " | " | " | " |
| 416 | (4,5-dihydrothiazol-2-yl)—NH— | " | " | " | " | " | " |
| 417 | (4,5-dihydrooxazol-2-yl)—NH— | " | " | " | " | " | " |
| 418 | (pyrimidin-2-yl)—NH— | " | " | " | " | " | " |
| 419 | (1H-benzimidazol-2-yl)—NH— | " | " | " | " | " | " |

TABLE 20-continued
| number | RR¹N— | position of substitution | A | R² | R³ | R⁴ | R⁵ |
|---|---|---|---|---|---|---|---|
| 420 | 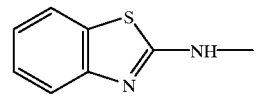 | " | " | " | " | " | " |
| 421 | 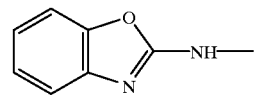 | " | " | " | " | " | " |
| 422 | HN=CH—NH— | " | " | " | " | " | " |
| 423 | 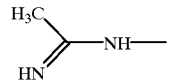 | " | " | " | " | " | " |
| 424 | 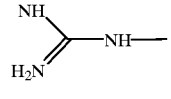 | " | —CH₂— | " | " | " | 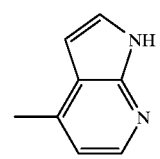 |
| 425 | 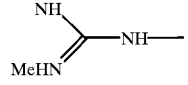 | " | " | " | " | " | " |
| 426 | 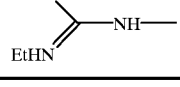 | " | " | " | " | " | " |
TABLE 21
| number | RR¹N— | position of substitution | A | R² | R³ | R⁴ | R⁵ |
|---|---|---|---|---|---|---|---|
| 427 | 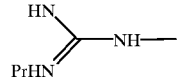 | 4 | —CH₂— | H | H | H | 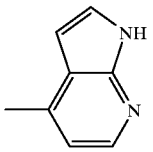 |
| 428 | 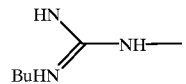 | " | " | " | " | " | " |
| 429 | 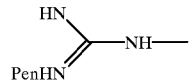 | " | " | " | " | " | " |
| 430 | 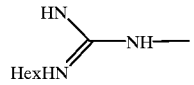 | " | " | " | " | " | " |

TABLE 21-continued

| number | RR$^1$N— | position of substitution | A | R$^2$ | R$^3$ | R$^4$ | R$^5$ |
|---|---|---|---|---|---|---|---|
| 431 | HN=C(PhNH)-NH— | " | " | " | " | " | " |
| 432 | HN=C(BnNH)-NH— | " | " | " | " | " | " |
| 433 | HN=C(PhenetyNH)-NH— | " | " | " | " | " | " |
| 434 | MeN=C(MeNH)-NH— | " | " | " | " | " | " |
| 435 | MeN=C(EtNH)-NH— | " | " | " | " | " | " |
| 436 | MeN=C(PtNH)-NH— | " | " | " | " | " | " |
| 437 | NCN=C(H$_2$N)-NH— | " | " | " | " | " | " |
| 438 | O$_2$NN=C(H$_2$N)-NH— | " | " | " | " | " | " |
| 439 | 4,5-dihydroimidazol-2-yl-NH— | " | " | " | " | " | " |
| 440 | 3,4,5,6-tetrahydropyridin-2-yl-NH— | " | " | " | " | " | " |
| 441 | 1H-imidazol-2-yl-NH— | " | " | " | " | " | " |
| 442 | 1H-1,2,4-triazol-3-yl-NH— | " | " | " | " | " | " |

TABLE 22
| number | RR¹N— | position of substitution | A | R² | R³ | R⁴ | R⁵ |
|---|---|---|---|---|---|---|---|
| 443 | 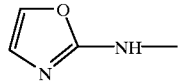 | 4 | —CJ₂— | H | H | H | 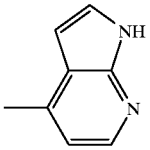 |
| 444 | 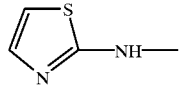 | " | " | " | " | " | " |
| 445 | 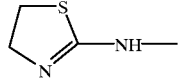 | " | " | " | " | " | " |
| 446 | 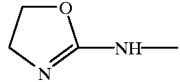 | " | " | " | " | " | " |
| 447 | 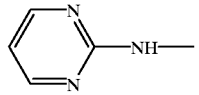 | " | " | " | " | " | " |
| 448 | 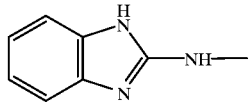 | " | " | " | " | " | " |
| 449 | 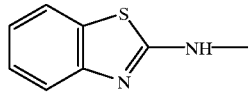 | " | " | " | " | " | " |
| 450 | 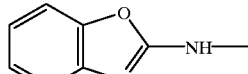 | " | " | " | " | " | " |
| 451 | H₂NCH=N— | " | " | " | " | " | " |
| 452 | 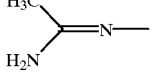 | " | " | " | " | " | " |
| 453 | 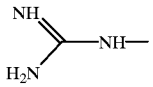 | " | —CH(Me)— | " | " | " | " |
| 454 | 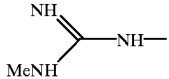 | " | " | " | " | " | " |
| 455 | 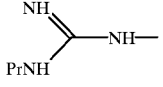 | " | " | " | " | " | " |

TABLE 22-continued
| number | RR¹N— | position of substitution | A | R² | R³ | R⁴ | R⁵ |
|---|---|---|---|---|---|---|---|
| 456 | 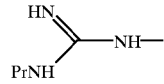 PrNH | " | " | " | " | " | " |
| 457 | 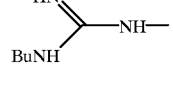 BuNH | " | " | " | " | " | " |
| 458 | 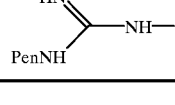 PenNH | " | " | " | " | " | " |
TABLE 23
| number | RR¹N— | position of substitution | A | R² | R³ | R⁴ | R⁵ |
|---|---|---|---|---|---|---|---|
| 459 | 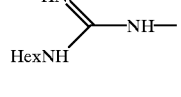 HexNH | 4 | —CH(Me)— | H | H | H | 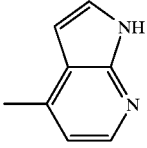 |
| 460 | 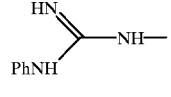 PhNH | " | " | " | " | " | " |
| 461 | 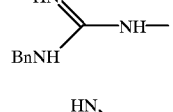 BnNH | " | " | " | " | " | " |
| 462 | 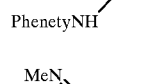 PhenetyNH | " | " | " | " | " | " |
| 463 | 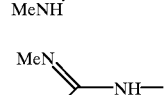 MeNH | " | " | " | " | " | " |
| 464 | 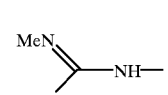 EtNH | " | " | " | " | " | " |
| 465 | 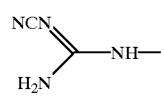 PrNH | " | " | " | " | " | " |
| 466 | 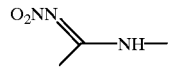 H₂N | " | " | " | " | " | " |
| 467 |  H₂N | " | " | " | " | " | " |

TABLE 23-continued

| number | RR¹N— | position of substitution | A | R² | R³ | R⁴ | R⁵ |
|---|---|---|---|---|---|---|---|
| 468 | (4,5-dihydro-1H-imidazol-2-yl)NH— | " | " | " | " | " | " |
| 469 | (1,4,5,6-tetrahydropyrimidin-2-yl)NH— | " | " | " | " | " | " |
| 470 | (1H-imidazol-2-yl)NH— | " | " | " | " | " | " |
| 471 | (1H-1,2,4-triazol-3-yl)NH— | " | " | " | " | " | " |
| 472 | (oxazol-2-yl)NH— | " | " | " | " | " | " |
| 473 | (thiazol-2-yl)NH— | " | " | " | " | " | " |
| 474 | (4,5-dihydrothiazol-2-yl)NH— | " | " | " | " | " | " |

TABLE 24

| number | RR¹N— | position of substitution | A | R² | R³ | R⁴ | R⁵ |
|---|---|---|---|---|---|---|---|
| 475 | (4,5-dihydrooxazol-2-yl)NH— | 4 | —CH(Me)— | H | H | H | 7-azaindol-4-yl |
| 476 | (pyrimidin-2-yl)NH— | " | " | " | " | " | " |
| 477 | (1H-benzimidazol-2-yl)NH— | " | " | " | " | " | " |

TABLE 24-continued
| number | RR¹N— | position of substitution | A | R² | R³ | R⁴ | R⁵ |
|---|---|---|---|---|---|---|---|
| 478 | 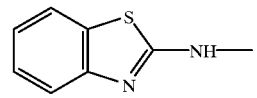 | " | " | " | " | " | " |
| 479 | 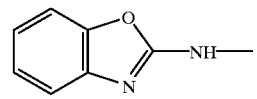 | " | " | " | " | " | " |
| 480 | H₂NCH=N— | " | " | " | " | " | " |
| 481 | 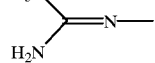 | " | " | " | " | " | " |
| 482 | 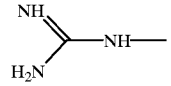 | " | —CH₂— | " | " | " | 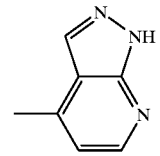 |
| 483 | 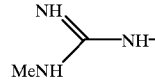 | " | " | " | " | " | " |
| 484 | 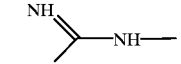 | " | " | " | " | " | " |
| 485 | 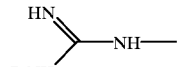 | " | " | " | " | " | " |
| 486 | 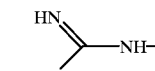 | " | " | " | " | " | " |
| 487 | 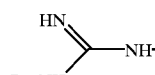 | " | " | " | " | " | " |
| 488 | 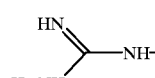 | " | " | " | " | " | " |
| 489 | 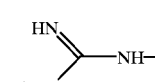 | " | " | " | " | " | " |
| 490 | 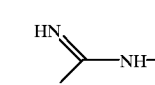 | " | " | " | " | " | " |

TABLE 25
| number | RR¹N— | position of substitution | A | R² | R³ | R⁴ | R⁵ |
|---|---|---|---|---|---|---|---|
| 491 | 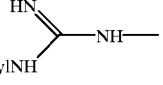 PhenetylNH | 4 | —CH₂— | H | H | H |  |
| 492 | 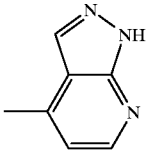 MeNH | " | " | " | " | " | " |
| 493 | 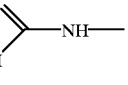 EtNH | " | " | " | " | " | " |
| 494 |  PrNH | " | " | " | " | " | " |
| 495 |  | " | " | " | " | " | " |
| 496 |  | " | " | " | " | " | " |
| 497 |  | " | " | " | " | " | " |
| 498 |  | " | " | " | " | " | " |
| 499 |  | " | " | " | " | " | " |
| 500 |  | " | " | " | " | " | " |
| 501 |  | " | " | " | " | " | " |
| 502 |  | " | " | " | " | " | " |
| 503 | 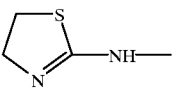 | " | " | " | " | " | " |

TABLE 25-continued

| number | RR¹N— | position of substitution | A | R² | R³ | R⁴ | R⁵ |
|---|---|---|---|---|---|---|---|
| 504 | (4,5-dihydrooxazol-2-yl)NH— | " | " | " | " | " | " |
| 505 | (pyrimidin-2-yl)NH— | " | " | " | " | " | " |
| 506 | (1H-benzimidazol-2-yl)NH— | " | " | " | " | " | " |

TABLE 26

| number | RR¹N— | position of substitution | A | R² | R³ | R⁴ | R⁵ |
|---|---|---|---|---|---|---|---|
| 507 | (benzothiazol-2-yl)NH— | 4 | —CH₂— | H | H | H | (1H-pyrazolo[3,4-b]pyridin-4-yl)— |
| 508 | (benzoxazol-2-yl)NH— | " | " | " | " | " | " |
| 509 | H₂NCH=N— | " | " | " | " | " | " |
| 510 | H₃C-C(NH₂)=N— | " | " | " | " | " | " |
| 511 | H₂N-C(=NH)-NH— | " | —CH(Me)— | " | " | " | " |
| 512 | MeNH-C(=NH)-NH— | " | " | " | " | " | " |
| 513 | EtNH-C(=NH)-NH— | " | " | " | " | " | " |
| 514 | PrNH-C(=NH)-NH— | " | " | " | " | " | " |
| 515 | BuNH-C(=NH)-NH— | " | " | " | " | " | " |

TABLE 26-continued
| number | RR¹N— | position of substitution | A | R² | R³ | R⁴ | R⁵ |
|---|---|---|---|---|---|---|---|
| 516 | 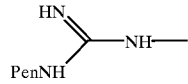 PenNH | " | " | " | " | " | " |
| 517 | 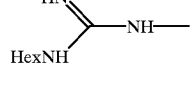 HexNH | " | " | " | " | " | " |
| 518 | 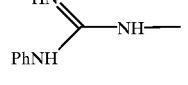 PhNH | " | " | " | " | " | " |
| 519 | 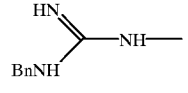 BnNH | " | " | " | " | " | " |
| 520 | 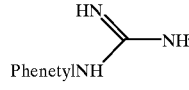 PhenetylNH | " | " | " | " | " | " |
| 521 | 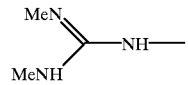 MeNH | " | " | " | " | " | " |
| 522 | 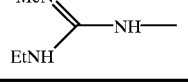 EtNH | " | " | " | " | " | " |
TABLE 27
| number | RR¹N— | position of substitution | A | R² | R³ | R⁴ | R⁵ |
|---|---|---|---|---|---|---|---|
| 523 | 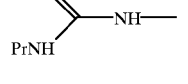 PrNH | 4 | —CH(Me)— | H | H | H | 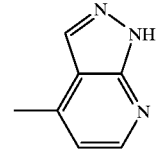 |
| 524 | 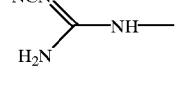 | " | " | " | " | " | " |
| 525 | 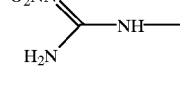 | " | " | " | " | " | " |
| 526 | 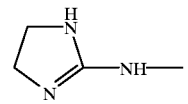 | " | " | " | " | " | " |

TABLE 27-continued
| number | RR¹N— | position of substitution | A | R² | R³ | R⁴ | R⁵ |
|---|---|---|---|---|---|---|---|
| 527 |  | " | " | " | " | " | " |
| 528 | 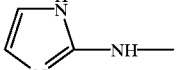 | " | " | " | " | " | " |
| 529 | 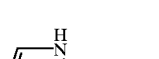 | " | " | " | " | " | " |
| 530 | 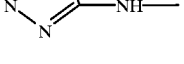 | " | " | " | " | " | " |
| 531 | 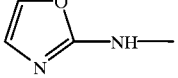 | " | " | " | " | " | " |
| 532 | 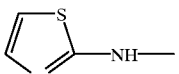 | " | " | " | " | " | " |
| 533 | 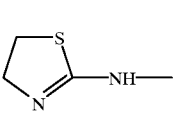 | " | " | " | " | " | " |
| 534 |  | " | " | " | " | " | " |
| 535 | 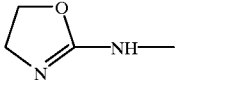 | " | " | " | " | " | " |
| 536 | 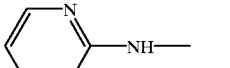 | " | " | " | " | " | " |
| 537 | 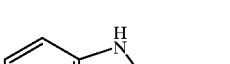 | " | " | " | " | " | " |
| 538 | HN=CH—NH— | " | " | " | " | " | " |

TABLE 28
| number | RR¹N— | position of substitution | A | R² | R³ | R⁴ | R⁵ |
|---|---|---|---|---|---|---|---|
| 539 | 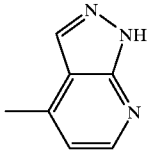 | 4 | —CH(Me)— | H | H | H | 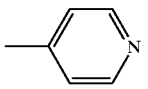 |
| 540 | H₂N | " | —CH₂— | " | " | Me | 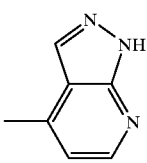 |
| 541 | " | " | " | " | " | " | 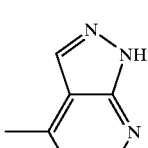 |
| 542 | " | " | " | " | " | " | 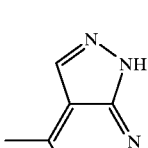 |
| 543 |  | " | " | " | " | H | 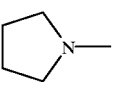 |
| 544 | 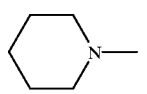 | " | " | " | " | " | " |
| 545 | 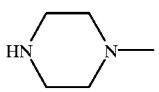 | " | " | " | " | " | " |
| 546 | 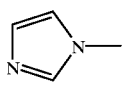 | " | " | " | " | " | " |
| 547 | 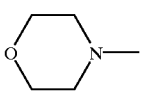 | " | " | " | " | " | " |
| 548 |  | " | " | " | " | " | " |
| 549 |  | " | " | " | " | " | " |

TABLE 28-continued

| number | RR¹N— | position of substitution | A | R² | R³ | R⁴ | R⁵ |
|---|---|---|---|---|---|---|---|
| 550 | S⌒N— (thiomorpholinyl) | " | " | " | " | " | " |
| 551 | H₂N— | " | " | 2-Bn | " | " | " |
| 552 | " | " | " | 3-Bn | " | " | " |
| 553 | " | " | " | 2-SBn | " | " | " |
| 554 | " | " | " | 3-SBn | " | " | " |
| 555 | " | " | —CH(Me)— | 3-N₃ | " | " | " |

TABLE 29

| number | RR¹N— | position of substitution | A | R² | R³ | R⁴ | R⁵ |
|---|---|---|---|---|---|---|---|
| 556 | H₂N— | 4 | —CH(Me)— | 3-N₃ | H | H | 3-iodo-4-methyl-1H-pyrazolo[3,4-b]pyridinyl |
| 557 | " | " | " | 3-N₃ | " | " | 4-methyl-1H-pyrazolo[3,4-b]pyridinyl |
| 558 | " | " | " | 2-N₃ | " | " | " |
| 559 | " | " | —CH₂— | 3-Me | 5-Me | " | " |
| 560 | H₂N–C(=NH)–NH— | " | " | 3-NO₂ | H | " | " |
| 561 | " | " | —CH(Me)— | 3-NO₂ | " | " | " |
| 562 | " | " | —CH₂— | 2-NO₂ | " | " | " |
| 563 | " | " | —CH(Me)— | 2-NO₂ | " | " | " |
| 564 | " | " | " | 3-N₃ | " | " | " |
| 565 | " | " | " | 2-N₃ | " | " | " |
| 566 | " | " | —CH₂— | 3-Me | 5-Me | " | " |
| 567 | " | " | — | H | H | " | " |
| 568 | H₂N— | " | —CH(CH₂OH)— | " | " | " | " |
| 569 | " | " | —CH(CO₂H)— | " | " | " | " |
| 570 | " | " | —CH(CO₂Me)— | " | " | " | " |
| 571 | " | " | —CH(Me)— | " | " | " | 3-iodo-4-methyl-1H-pyrazolo[3,4-b]pyridinyl |

TABLE 30

| number | RR¹N— | position of substitution | A | R² | R³ | R⁴ | R⁵ |
|---|---|---|---|---|---|---|---|
| 572 | H₂N— | 4 | —CH₂— | 3-NO₂ | H | H | 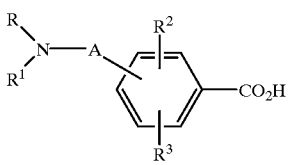 |
| 573 | " | " | " | 2-CN | " | " | " |
| 574 | MeNH— | " | —CH(Me)— | H | " | " | " |
| 575 | EtNH— | " | " | " | " | " | " |
| 576 | nPrNH— | " | " | " | " | " | " |
| 577 | nBuNH— | " | " | " | " | " | " |
| 578 | (Me)₂N— | " | " | " | " | " | " |
| 579 | (Et)₂N— | " | " | " | " | " | " |

The compound (I) of the present invention can be synthesized by the following route.

Method 1

A method comprising reacting a carboxylic acid compound of the formula

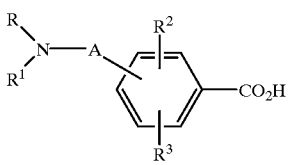

(IV)

wherein R, $R^1$, $R^2$, $R^3$ and A are as defined above, or a reaction derivative thereof, with an amino compound of the formula

(V)

wherein $R^4$ and $R^5$ are as defined above.

The reactive derivative of carboxylic acid compound includes acid halide such as acid chloride, acid anhydride, mixed acid anhydride formed from ethyl chloroformate and the like, ester such as methyl ester, ethyl ester and the like, a reactive derivative produced from carbodiimide such as dicyclohexylcarbodiimide, and the like.

The reaction is carried out in the presence of an inert solvent, which is generally an organic solvent without hydroxy such as tetrahydrofuran, ethyl acetate, benzene, toluene, carbon tetrachloride, chloroform, methylene chloride, dimethylformamide and dimethylimidazolidinone. The reaction proceeds at an optical temperature such as −10° C. to 200° C., preferably from 0° C. to 80° C. When the starting material is a reactive derivative (e.g., ester) having less greater reactivity, a high reaction temperature is used; when it is a reactive derivative having greater reactivity (e.g., mixed acid anhydride), a low reaction temperature is used. Where necessary, an organic base such as pyridine, triethylamine, diisopropylethylamine and the like may be used as a deacidifying agent. As occasion demands, the amino group of the formula (IV) can be protected with an amino-protecting group such as benzyloxycarbonyl and tert-butyloxycarbonyl before reaction. Said protecting group can be removed after reaction by conventional method.

The carboxylic acid compound of the formula (IV) which is a starting material of synthesis of the present invention can be easily synthesized from a commercially available starting material by a known method, or the method described in WO93/05021.

An amine compound of the formula (V) which is the other synthesis starting material can be synthesized by the method described in WO93/05021.

In particular, a compound of the formula (IV) wherein R is

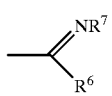

(II)

wherein $R^6$ and $R^7$ are as defined above, can be easily synthesized by the following method.

That is, a compound of the formula

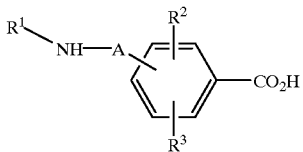

(VI)

wherein $R^1$, $R^2$, $R^3$ and A are as defined above, and a compound of the formula

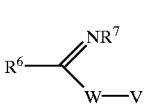

(VII)

wherein $R^6$ and $R^7$ are as defined above, when $R^6$ is amino group, it may be protected by tert-butoxycarbonyl, benzyloxycarbonyl, acetyl, benzoyl and the like, W is oxygen, sulfur or heterocycle such as pyrazole, and V is hydrogen, lower alkyl such as methyl, ethyl and propyl, benzyl, p-nitrobenzyl or the like, or an acid addition salt thereof are condensed to give the desired compound.

Examples of the compound of the formula (VII) include S-methylisothiourea, O-methylisourea, S-ethylisothiourea, O-ethylisourea, N,N'-S-trimethylisothiourea, N,N'-O-trimethylisourea, N,S-dimethylisothiourea, N,O-dimethylisoureaa, N-ethyl-S-methylisothiourea, N-ethyl-O-methylisourea, 2-methylthio-2-benzimidazole, 2-methylthio-2-benzothiazole, 2-methylthio-2-benzoaxazole, 2-methylthio-2-imidazoline, 2-methoxy-2-imidazoline, 2-methylthio-3,4,5,6-tetrahydropyrimidine, 2-methylthiothiazoline, N,N'-dibenzyloxycarbonyl-S-methylisothiourea, N,N'-diacetyl-S-methylisothiourea, ethyl formimidate, methyl formimidate, methyl acetimidate, ethyl acetimidate, ethyl (N-methyl)formimidate, methyl N-methylformimidate, pyrazole-1-carboxamidine, 3,5-dimethylpyrazole-1-carboxamidine, and the like. Examples of acid addition salts thereof include hydroiodide, hydrobromide, hydrochloride, sulfate, p-toluenesulfonate and the like.

The reaction is generally carried out in a solvent such as water, alcohols (e.g., methanol and ethanol) alone or a mixture therof with water, and polar solvents (e.g., dimethylformamide, dioxane and tetrahydrofuran), or a mixture thereof with water. The compound of the formula (VII) is preferably used in an amount of 1- to 10-fold moles, and the reaction is preferably carried out at an optional temperature, such as 0–100° C. Where necessary, a deacidifying agent such as inorganic base (e.g., potassium carbonate, sodium carbonate, potassium hydroxide and sodium hydroxide) and organic base (e.g., pyridine, 4-dimethylaminopyridine, triethylamine and diisopropylethylamine) may be preferably used.

Method 2

A compound (I) wherein one of R and R' is hydrogen and the other is hydrogen or a group other than formula (II) can be produced by reacting an amine compound, wherein R and $R^1$ are hydrogen which is obtained by Method 1, of the formula

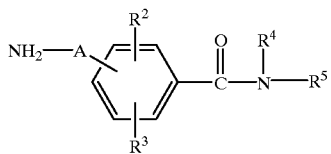
(VIII)

wherein $R^2$, $R^3$, $R^4$, $R^5$ and A are as defined above, and a halide compound, aldehyde compound or ketone compound.

The halide compound to be used in this reaction is represented by the formula $R^{12}$—Hal  (IX)

wherein $R^{12}$ is alkyl having 1 to 6 carbon atoms, cycloalkyl having 3 to 7 carbon atoms, cycloalkylalkyl, phenyl or aralkyl optionally having substituent on the ring, and Hal is halogen, preferably chlorine or bromine; aldehyde compound is represented by the formula $R^{13}$CHO  (X)

wherein $R^{13}$ is hydrogen, alkyl having 1 to 5 carbon atoms, or phenyl or aralkyl optionally having substituent on the ring; and ketone compound is represented by the formula

(XI)

wherein $R^{14}$ and $R^{15}$ are the same or different and each is alkyl having 1 to 5 carbon atoms, or phenyl or aralkyl optionally having substituent on the ring, or $R^{14}$ and $R^{15}$ combinedly form together with carbonyl cycloalkyl having 3 to 7 carbon atoms.

Compound (VIII) and halide compound may be reacted under the same conditions as in Method 1. It is preferable that deacidifying condensation be carried out in the presence of a base such as sodium carbonate, sodium hydrogencarbonate, sodium hydroxide, potassium hydroxide, triethylamine and pyridine.

Compound (VIII) and aldehyde or ketone are subjected to dehydrative condensation in a solvent hardly miscible with water, such as benzene, toluene, xylene, carbon tetrachloride, chloroform, dichloro-methane and the like with reflux under heating. It is also beneficial to add a small amount of an acid such as p-toluenesulfonic acid.

The compound obtained by the above condensation, such as alkylidene compound and phenylalkylidene compound, may be subjected to reduction to derive a compound such as alkyl compound and aralkyl compound.

The reduction can be generally carried out in an alcohol such as methanol, ethanol, isopropyl alcohol and the like at −10 to 100° C. preferably 0 to 40° C. The reaction proceeds in the presence of a reducing agent such as sodium borohydride, or in the presence of a small amount of an acid such as hydrochloric acid, hydrobromic acid and acetic acid using a reducing agent such as sodium cyanoborohydride. When other groups of the objective compound are not affected, catalytic reduction using Raney nickel, palladium carbon, platinum oxide and the like may be employed. Alternatively, reductive amination can also produce the objective compound.

Method 3

A compound (I) wherein R and R' combinedly form together with the binding nitrogen atom a heterocycle optionally containing, in the ring, oxygen atom, sulfur atom or optionally substituted nitrogen atom additionally in the ring, such as pyrrolidinyl, pipderidyl, piperazinyl, morpholino and thiomorpholino, can be produced by reacting compound of the formula

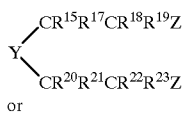
(XII)

or

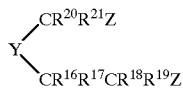
(XIII)

wherein, in (XII) and (XIII), $R^{16-23}$ are the same or different and each is hydrogen, halogen, alkyl having 1 to 6 carbon atoms, alkoxy having 1 to 6 carbon atoms, aralkyl, haloalkyl, nitro, amino, cyano, optionally substituted hydrazino, Y is carbon atom, oxygen atom, sulfur atom or optionally substituted nitrogen atom, Z is halogen (e.g., chlorine and bromine), alcohol reactive derivative such as sulfonyloxy (e.g., methanesulfonyloxy, p-toluenesulfonyloxy and trifluoromethanesulfonyloxy) and the like, provided the number of the substituent of heterocycle thus formed is 1 to 3 and compound (VIII).

The reaction proceeds under the same conditions as in Method 2.

Method 4

A compound of the formula (I) wherein R is

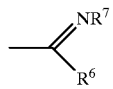  (II)

wherein $R^6$ and $R^7$ are as defined above, can be synthesized by subjecting an amine compound, which can be synthesized by the method described in WO93/05021, of the formula

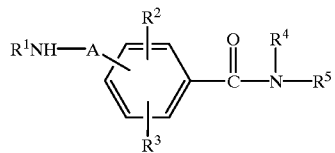  (XIV)

wherein $R^1$, $R^2$, $R^3$, $R^4$, $R^5$ and A are as defined above, and compound of the formula (VII) to condensation. The reaction proceeds under the same conditions as in the reaction of compounds (IV) and (VII) in Method 1.

A compound of the formula (I) wherein R is

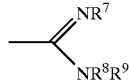

wherein $R^7$, $R^8$ and $R^9$ are as defined above, can be synthesized by the following Method 5 or Method 6.

Method 5

A compound of the formula (XIV) and an iso(thio)cyanate compound of the formula

 $R^7NC=X$  (XV)

wherein $R^7$ is as defined above, and X is S or O, are reacted to give a compound of the formula

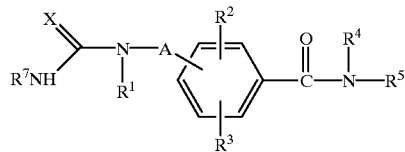  (XVI)

wherein $R^1$, $R^2$, $R^3$, $R^4$, $R^5$, $R^7$, A and X are as defined above.

Examples of the isocyanate or isothiocyanate compound of the formula (XV) shown here include methyl isocyanate, methyl isothiocyanate, ethyl isocyanate, ethyl isothiocyanate, phenyl isocyanage, phenyl isothiocyanate and the like. When $R^1$ is hydrogen, sodium isocyanate, sodium isothiocyanate, ammonium thiocyanate and the like are particularly used.

The reaction of compound (XIV) and (XV) is carried out in an alcohol solvent such as methanol and ethanol, or a solvent such as tetrahydrofuran, acetonitrile, dimethylformamide, chloroform, methylene chloride and the like. The reaction temperature is 0 to 200° C., particularly from room temperature to 100° C. The reaction of some compounds can be accelerated by the addition of an organic base such as pyridine and triethylamine. When $R^1$ is hydrogen, the reaction is carried out in an aqueous acid solution such as hydrochloric acid and sulfuric acid.

Then, (thio)ureido compound of the formula (XVI) is reacted with a suitable alkylating agent of the formula

 $R^{24}$—$X^1$  (XVII)

wherein $R^{24}$ is alkyl or aralkyl, and $X^1$ is halogen (e.g., chlorine, bromine and iodine) or sulfonyloxy (e.g., methanesulfonyloxy, p-toluenesulfonyloxy and trifluoromethanesulfonyloxy), to derive an alkylthiol compound of the formula

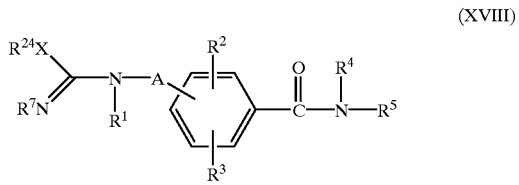  (XVIII)

wherein $R^1$, $R^2$, $R^3$, $R^4$, $R^5$, $R^7$, $R^{24}$, A and X are as defined above.

Examples of the suitable alkylating agent of the formula (XVII) include methyl iodide, ethyl iodide, benzyl bromide, p-nitrobenzyl bromide, dimethyl sulfate, diethyl sulfate and the like.

The reaction of the compound of the formula (XVI) and the compound of the formula (XVII) is carried out in a solvent such as acetone, tetrahydrofuran, acetonitrile, chloroform, dimethylformamide, dimethylimidazolidinone and the like. The reaction temperature is 0 to 150° C., particularly preferably from room temperature to 100° C. Where necessary, a base such as sodium hydride, potassium carbonate, sodium methoxide and the like may be used.

Then, the compound of the formula (XVIII) is reacted with an amine derivative of the formula $HNR^8R^9$ wherein $R^8$ and $R^9$ are as defined above to synthesize a compound of the formula (I) wherein R is

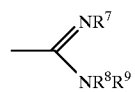

wherein $R^7$, $R^8$ and $R^9$ are as defined above.

Examples of the amine derivative of the formula $HNR^8R^9$ include ammonia, methylamine, ethylamine, propylamine, aniline, benzylamine, phenethylamine, N-methyl-N-benzylamine and the like.

The reaction of compound (XVIII) and $HNR^8R^9$ is carried out without solvent or in an alcohol solvent such as methanol and ethanol or a polar solvent such as tetrahydrofuran, acetonitrile, dimethylformamide and the like. While the amine derivative of the formula $HNR^8R^9$ is preferably used in an amount of 0.5–1.5 equivalents relative to compound (XVIII), 1.5–10 equivalents thereof may be used when the reaction is not affected. The reaction temperature is −20 to 150° C., preferably 0 to 100° C. This reaction can be accelerated by the addition of a base or a metal salt in an amount of 0.01–10 equivalents, preferably 0.1–3 equivalents. Examples of the base include inorganic base such as potassium carbonate, sodium carbonate and sodium hydrogencarbonate, and an organic base such as pyridine, triethylamine and 4-dimethylamino-pyridine, wherein the organic base may be used as a solvent. Examples of the metal salt include copper chloride, copper bromide, copper acetate, copper sulfate, mercury acetate and the like.

Alternatively, compound (XVI) and compound (XIX) are directly reacted according to the reaction of the above-mentioned compound (XV) and compound (XVI) to give the compound of the formula (I) wherein R is

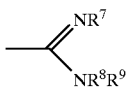

wherein $R^7$, $R^8$ and $R^9$ are as defined above.

Method 6

The compound of the formula (XVI) is reacted with a cyanide of the formula $$X^2\text{---CN} \tag{XIX}$$

wherein $X^2$ is halogen such as chlorine and bromine, to give a cyanamide compound of the formula

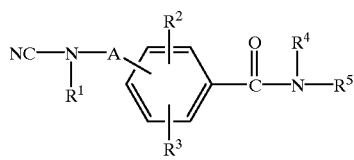 (XX)

wherein $R^1$, $R^2$, $R^3$, $R^4$, $R^5$ and A are as defined above, which is then reacted with an amine derivative of the formula $HNR^8R^9$ to synthesize a compound of the formula (I) wherein R is

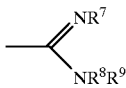

wherein $R^7$, $R^8$ and $R^9$ are as defined above.

The reaction of compound (XIV) and compound (XIX) is carried out in a solvent such as tetrahydrofuran, ether, acetone, methanol, ethanol, acetonitrile, dimethylformamide, dimethylimidazolidinone, chloroform, dichloromethane and the like. The reaction temperature is preferably −20 to 150° C., particularly preferably 0 to 80° C. For this reaction, an inorganic base such as potassium acetate, sodium acetate, potassium carbonate and sodium carbonate, or an organic base such as pyridine, triethylamine and 4-dimethylaminopyridine may be used.

The reaction of compound (XX) and $HNR^8R^9$ is carried out without solvent or in an alcohol solvent such as methanol, ethanol and the like or a polar solvent such as acetone, tetrahydrofuran, dioxane, dimethylformamide and the like. While the amine derivative of the formula $HNR^8R^9$ is preferably used in an amount of 0.8–1.5 equivalents relative to cyanamide compound (XX), 1.5–10 equivalents thereof may be used when the reaction is not affected. This reaction can be accelerated by the addition of a base in an amount of 0.01–10 equivalents, preferably 0.1–3 equivalents. Examples of preferable base advantageously include organic base such as pyridine, triethylamine and 4-dimethylaminopyridine, and inorganic base such as sodium carbonate, potassium carbonate, sodium hydroxide, potassium hydroxide and sodium hydrogencarbonate.

Method 7

A compound (I) wherein R and $R^1$ are the same or different and each is alkyl, phenyl, aralkyl or

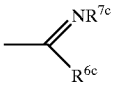 (II''')

wherein $R^{6c}$ and $R^{7c}$ combined form a heterocycle optionally containing oxygen atom, sulfur atom or optionally substituted nitrogen atom additionally in the ring, or a compound (I) wherein R and $R^1$ form, together with the bonding nitrogen atom, a heterocycle optionally containing, in the ring, oxygen atom, sulfur atom or optionally substituted nitrogen atom is obtained by reacting a compound (VIII) wherein the substituent of heterocycle at $R^5$ is not amino or hydrazino with sodium nitrite or potassium nitrite in the presence of hydrochloric acid, sulfuric acid, formic acid or acetic acid to give a hydroxy compound of the formula

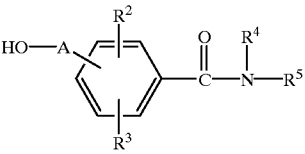 (XXI)

wherein $R^2$, $R^3$, $R^4$, $R^5$ and A are as defined above, which is reacted with a halogenating agent such as thionyl chloride, phosphorus oxychloride, phosphorus trichloride, phosphorus pentachloride, phosphorus tribromide and the like, or with methanesulfonyl chloride, p-toluenesulfonyl chloride and the like in the presence of an deacidifying agent to give a corresponding alcohol reactive derivative, and reacting this compound with an amine compound of the formula $$HNR^{25}R^{26} \tag{XXII}$$

wherein $R^{25}$ and $R^{26}$ are the same or different and each is alkyl, phenyl, aralkyl or heterocycle containing nitrogen atom, sulfur atom or oxygen atom, such as imidazole, triazole, thiazole, benzimidazole, oxazole, benzoxazole and the like, or $R^{25}$ and $R^{26}$ combinedly form, together with nitrogen atom, heterocycle optionally containing, in the ring, oxygen atom, sulfur atom and nitrogen atom, such as pyrrolidine, piperidine, morpholine, thiomorpholine, piperazine, imidazole, benzimidazole, thiazole, oxazole, benzoxazole and the like.

The reaction proceeds in the presence of a suitable base such as inorganic base which is exemplified by hydroxide, carbonate and hydrogencarbonate of alkali metal or alkaline earth metal (e.g., sodium hydroxide, potassium carbonate and sodium hydrogencarboante) and organic base such as pyridine and triethylamine.

In particular, the compound (I) of the present invention, having substituent on the benzene ring is converted to nitro by reacting the corresponding carboxylic acid or a derivative thereof with nitric acid/sulfuric acid, and converted to amine by various reductions with, for example, H$_2$/Raney Ni, Zn/AcOH and the like. Then, the compound is treated with sodium nitrate in the presence of an acid such as hydrochloric acid and sulfuric acid to give a diazonium salt, which is subjected to Sandmeyer reaction with, for example, copper chloride, copper bromide and copper cyanide, to convert respective functional groups. An iodine compound can be obtained by treating with potassium iodide. A fluorine compound can be synthesized by converting the diazonium salt to a borate with HBF$_4$ and heating the borate, or by treating with pyridine hydrofluoride. A carboxyl compound can be also obtained by hydrolysis of the nitrile compound obtained by Sandmeyer reaction, or directly by converting the benzene ring to lithium compound and treating the compound with carbon dioxide. An ester or amide compound can be easily obtained by conversion from the carboxylic acid by a conventional method. A hydroxy compound can be synthesized by heating the diazonium salt in an aqueous acid solution. An alkyloxy compound and aralkyloxy compound can be easily synthesized by treating the hydroxyl group with the corresponding alkyl halide or aralkyl halide in the presence of a base. An alkyl compound and aralkyl compound can be synthesized by Friedel-Crafts reaction using the corresponding alkyl, or aralkyl halide and AlCl$_3$, or by a reaction using a Grignard reagent prepared from aromatic halide and magnesium, or by coupling reaction of aromatic halide and the corresponding alkyl or aralkyl boron compound using a palladium catalyst.

The isomers encompassed in the compound (I) of the present invention can be prepared by isolation from mixtures of isomers by a conventional method, or by using various starting materials for isomers.

The compound (I) of the present invention thus obtained may have an amino group in or on the benzene ring or heterocycle containing nitrogen (heterocycle optionally containing, together with nitrogen atom, oxygen atom and sulfur atom, and optionally having substituent) wherein the amino group may be protected by a conventional amino-protecting group. The amino-protecting group is exemplified by alkanoyl having 1 to 5 carbon atoms such as formyl, acetyl, propionyl, butyryl, isobutyryl, pivaloyl and valeryl; alkoxycarbonyl having 2 to 5 carbon atoms such as methoxycarbonyl, ethoxycarbonyl, propoxycarbonyl, isopropoxycarbonyl, butoxycarbonyl, isobutoxycarbonyl and tert-butoxycarbonyl; cycloalkylcarbonyl having 4 to 8 carbon atoms such as cyclopropylcarbonyl, cyclobutylcarbonyl, cyclopentylcarbonyl, cyclohexylcarbonyl and cycloheptylcarbonyl; aroyl such as benzoyl and naphthoyl, wherein aroyl may have substituent such as halogen, alkyl having 1 to 6 carbon atoms, alkoxy having 1 to 6 carbon atoms, aralkyl, trifluoromethyl, nitro, amino and the like; phenyl-alkoxycarbonyl such as benzyloxycarbonyl, phenylethoxycarbonyl, phenylpropoxycarbonyl and phenylbutoxycarbonyl, wherein phenylethoxycarbonyl may have, on the phenyl ring, substituent such as halogen, alkyl having 1 to 6 carbon atoms, alkoxy having 1 to 6 carbon atoms, aralkyl, trifluoromethyl, nitro, amino and the like; phenylalkenyl such as styryl, cinnamyl, phenylbutenyl, phenylpentenyl, phenylhexenyl and the like; phenylalkylidene such as benzylidene, phenylethylidene and the like; a group forming pyrrolidylidene, piperidylidene and phthalimide; alkylcarbamoyl such as methylcarbamoyl, ethylcarbamoyl, dimethylcarbamoyl, diethylcarbamoyl, dipropylcarbamoyl and the like; alkylcarbamoylalkyl such as methylcarbamoylmethyl, ethylcarbamoylmethyl, dimethylcarbamoylmethyl, diethylcarbamoylmethyl, dimethylcarbamoylethyl and the like; alkoxymethyl such as methoxymethyl, ethoxymethyl, propoxymethyl, butoxymethyl, tert-butoxymethyl and the like; aralkyloxyalkyl such as benzyloxymethyl, p-methoxybenzyloxymethyl, o-nitrobenzyloxymethyl and the like; allyl; and cyclic ether such as tetrahydrofuran, tetrahydropyrane and the like.

The above-mentioned amino-protecting group can be removed by treating with conventional acid (e.g., hydrochloric acid, sulfuric acid, formic acid, acetic acid, trifluoroacetic acid, hydrobromic acid/acetic acid, hydrochloric acid/dioxane, hydrogen fluoride, methanesulfonic acid and trifluoromethanesulfonic acid), Lewis acid (e.g., boron trifluoride etherate, titanium tetrachloride, tin tetrachloride, aluminum chloride, boron tribromide and iodotrimethylsilane) or alkali (e.g., ammonia, sodium methoxide, sodium ethoxide, sodium carbonate, potassium carbonate, sodium hydrogencarbonate, potassium hydrogencarbonate, sodium hydroxide, potassium hydroxide and hydrazine).

The deprotection can be carried out by catalytic reduction using 5% palladium carbon, 10% palladium carbon, 10% palladium hydroxide carbon, Raney nickel and the like as a catalyst, reduction using, in liquid ammonia, metallic sodium or metallic lithium, or reduction using sodium borohydride, lithium aluminum hydride, diborane, zinc, sodium amalgam and the like as a reducing agent. Further, a method using an oxidizing agent such as hydrogen peroxide, potassium permanganate, 2,3-dichloro-5,6-dicyano-1,4-benzoquinone (DDQ), N-bromosuccinimide and the like may be used.

The compound (I) thus obtained can be separated and purified from reaction mixtures by a method known per se such as recrystallization and chromatography.

The compound (I) can be further converted to pharmaceutically acceptable acid addition salts by a conventional method. The acid to be used for forming acid addition salts may be appropriately selected from an inorganic acid (e.g., hydrochloric acid, hydrobromic acid, sulfuric acid and phosphoric acid) and an organic acid (e.g., acetic acid, methanesulfonic acid, maleic acid and fumaric acid). These salts can be converted to the corresponding free base by a conventional method, such as reaction with alkali such as sodium hydroxide and potassium hydroxide. Further, a quaternary ammonium salt can be prepared. A compound (I) having a carboxyl group can be converted to a metal salt (e.g., sodium, potassium, calcium and aluminum) or salt with amino acid (e.g., lysine and ornithine).

The effects afforded by the compound of the present invention are explained in detail by way of pharmacological experiments.

Pharmacological Experiment 1: hypotensive effects

To spontaneously hypertensive rates (SHR) weighting 350–450 g (3–5 per group) was orally administered a test compound (30 mg/kg) dissolved in 0.5% hydroxypropylmethylcellulose, and systolic blood pressure at one hour after administration was determined by tail cuff method to examine hypotensive effects. The results are shown in Table 31.

TABLE 31

| Compound | Dose (mg/kg) | hypotensive effect (mmHg) (SHR P.O.) |
|---|---|---|
| Example 1 | 30 | −116 |
| Example 9 | 30 | −131 |

Pharmacological Experiment 2: vasodilating effects

Male rabbits (body weight 1.9–3.0 kg) were anesthetized with sodium pentobarbital and killed by exsanguinity. The thoracic aorta was removed and about 2 mm wide ring specimens were prepared. The specimens were hung in a 40 ml Magnus bath filled with Krebs-Henseleit solution (NaCl 117 mM; KCl 4.7 mM; CaCl$_2$ 2.5 mM; MgSO$_4$ 1.2 mM; NaHCO$_3$ 24.8 mM; KH$_2$PO$_4$ 1.2 mM; glucose 11.0 mM) at 37° C. at a load of 2 g. The Magnus bath was constantly aerated with a mixed gas (95% oxygen+5% carbon dioxide). The tension of the specimens was measured by isometric transducer (TB-611T, Nihon Koden). The specimens were contracted with phenylephrine ($10^{-6}$M) and when the contraction became constant, the compound was cumultatively added to observe relaxing response. The relaxing response by the compound was calculated relative to contraction by phenylephrine as 100% as the concentration necessary for 50% relaxation (IC$_{50}$, μM). The results are shown in Table 32.

TABLE 32

| Compound | vasodilating action (μM) |
|---|---|
| Example 9 | 0.05 |
| Example 150 | 0.03 |

Pharmacological Experiment 3: Effect on contraction caused by acetylcholine in tracheal specimen extracted from guinea pig Male Hartley guinea pigs (body weight 260–390 g) were anesthetized by intraperitoneal administration of pentobarbital sodium (100 mg/kg) and killed by exsanguinity. The trachea was removed and ventral cartilage was cut open and ligament was cut in 3 mm width to prepare specimens. The specimens were hung in a 40 ml Magnus bath filled with Krebs-Henseleit solution (NaCl 117 mM; KCl 4.7 mM; CaCl$_2$ 2.5 mM; MgSO$_4$ 1.2 mM; NaHCO$_3$ 24.8 mM; KH$_2$PO$_4$ 1.2 mM; glucose 11.0 mM) at 37° C. at a load of 1 g. The Magnus bath was constantly aerated with a mixed gas (95% oxygen+5% carbon dioxide). The tension of the specimens was measured by isometric transducer (TB-611T, Nihon Koden) and recorded on a recorder (Ti-102, Tokai Irika). The specimens were contracted with acetylcholine ($10^{-6}$M) and when the contraction became constant, the compound was cumulatively added to observe relaxing response. The relaxing response by the compound was calculated relative to maximum response by papaverine ($10^{-4}$M) as 100% as the concentration necessary for 50% relaxation (IC$_{50}$, μM). The results are shown in Table 33.

TABLE 33

| Compound | bronchodilative action (IC$_{50}$, μM) |
|---|---|
| Example 9 | 0.05 |

Pharmacological Experiment 4: Action on coronary blood flow

Adult mongrel dogs (2–3 per group) are anesthetized by intravenous administration (30 mg/kg) of pentobarbital sodium, and left coronary artery is perfused according to the method of Yago et al. [Folia Pharmacologica Japonica, vol. 57, p. 380 (1961)], and the blood flow is measured. The test compound (10–300 μg) is administered into coronary artery. The effect on coronary blood flow of the test compound is expressed as ED$_{50}$ (μg) which is the dose necessary for increasing coronary blood flow to the level corresponding to the half of the effect achieved by administration of nifedipine [dimethyl 2,6-dimethyl-4-(2-nitrophenyl)-1,4-dihydropyridine- 3,5-dicarboxylate] (3 μg) into coronary artery. As the duration of the effect, half-life (T ½, min) is also determined.

Pharmacological Experiment 5: Cerebral, coronary or renal artery blood flow increasing action Adult mongrel dogs are anesthetized with 30 mg/kg, i.v. of pentobarbital sodium, and artificially respirated (20 ml/kg, 18 times/min) using an artificial respiratory apparatus (manufactured by Harvard). Left vertebral, left coronary circumflex brand and right renal artery are exposed, equipped with a blood flow probe, and blood flow is measured by electromagnetic flowmeter (Nihon Koden). The test compound is administered into vein from a cannula dwelled in femoral vein. The action of the test compound is expressed as a ratio of increase from the blood flow before administration of the test compound.

Pharmacological Experiment 6: Peripheral artery blood flow increasing action

Male rats are anesthetized with pentobarbital sodium (50 mg/kg, i.p.) and fixed at a dorsal position. A probe is equipped at right planta, and blood flow is measured by a laser flowmeter (manufactured by Advance). The test compound is administered into vein from a cannula dwelled in femoral vein. The action of the test compound is expressed as a ratio of increase from the blood flow before administration of the test compound.

The compound (I) of the present invention, isomers thereof and pharmaceutically acceptable acid addition salts thereof have strong smooth muscle relaxing action, and can increase coronary and cerebral blood flow like calcium antagonists. In addition, they have renal and peripheral circulation improving action which cannot be seen in conventional calcium antagonists, and the blood flow increasing action lasts for an extended period. They suppress not only smooth muscle contracting action associated with increase in intracellular calcium, but also contraction of smooth muscle caused by promotion of sensitivity to calcium.

Accordingly, the compound of the present invention is useful as a strong and long-acting agent for prophylaxis and treatment of circulatory diseases in coronary, cerebral, renal and peripheral arteries, as a therapeutic agent for hypertenison, angina pectoris, and renal and peripheral circulation disorder, an inhibitor of cerebral vasospasm and the like.

Moreover, the compound of the present invention shows the inhibitory action on experimental asthma in guinea pig which was induced by histamin inhalation and on the inhibitory action on the contraction induced by acetylcholine in tracheal specimens extracted from guinea pig, and is useful as a therapeutic agent for asthma.

The compound (I) of the present invention, isomers therof and pharmaceutically acceptable acid addition salts thereof are highly safe, and permit superior oral absorption, as is evident from the results of Pharmacological Experiment 1.

When the compound (I) of the present invention is used as a pharmaceutical, an effective amount thereof is admixed with suitable, pharmacologically acceptable additives for pharmaceutical preparations, such as excipients, carriers, diluents and the like, and prepared into tablets, granules, powders, capsules, injections, inhalants, ointments, suppositories and the like which can be administered orally or parenterally.

While the clinical dose varies depending on age, body weight, symptom and the like of patients, it is generally 1–500 mg daily for an adult by oral administration, which can be administered in a single dose or several doses.

BEST MODE FOR EMBODYING THE INVENTION

The present invention is specially described by way of Examples, to which the invention is not limited.

EXAMPLE 1

(R)-N-(4-pyridyl)-4-(1-aminoethyl)benzamide dihydrochloride monohydrate (Compound 2, R-configuration)

(a) Thionyl chloride (1.43 ml) and dimethylformamide (2 drops) were added to a solution of (R)-(+)-4-(1-benzyloxycarbonylaminoethyl)-benzoic acid (2 g) in dichloromethane (20 ml), and the mixture was refluxed under heating for 1 hour. Afterthe reaction, the solvent was evaporated under reduced pressure to give (R)-4-(1-benzyloxycarbonylaminoethyl)benzoyl chloride as crystals. Then, the crystals were dissolved in acetonitrile (10 ml) and the solution was dropwise added to a solution of 4-aminopyridine (525 mg) and diisopropylethylamine (1.17 ml) in acetonitrile (20 ml) under ice-cooling, which was followed by stirring at room temperature for 5 hours. After the reaction, water was added, and the mixture was extracted with ethyl acetate. The extract was washed with water and dried. The solvent was evaporated under reduced pressure. The obtained crystals were recrystallized from methanol-ethyl acetate-hexane to give 1.87 g of (R)-N-(4-pyridyl)-4-(1-benzyloxycarbonylaminoethyl)benzamide.

PMR (CDCl$_3$/TMS) δ: 1.45(3H,d,J=6.8 Hz), 4.84(1H,m), 5.03(1H,d,J=12 Hz), 5.09(1H,d,J=12 Hz), 5.18(1H,brs), 7.33(7H,m), 7.60(2H,d,J=5.9 Hz), 7.77(2H,d,J=7.8 Hz), 8.50(2H,d,J=5.9 Hz)

(b) (R)-N-(4-Pyridyl)-4-(1-benzyloxycarbonylaminoethyl)benzamide (1.87 g) and 10% palladium hydroxide carbon (300 mg) were added to methanol (20 ml), and the mixture was subjected to catalytic reduction in a stream of hydrogen. After the reaction, the catalyst was removed by filtration. The mixture was concentrated under reduced pressure, and a hydrochloric acid-methanol solution was added to the obtained crystals. The solvent was evaporated under reduced pressure. The obtained crystals were recrystallized from methanol-ethyl acetate to give 1.0 g of (R)-N-(4-pyridyl)-4-(1-aminoethyl)benzamide dihydrochloride monohydrate having a melting point of 287–288° C. [α]$_D$=+3.2° (methanol, c=1)

PMR (DMSO-d$_6$/TMS)δ: 1.53(3H,d,J=6.8 Hz), 4.5(1H, brs), 7.70(2H,d,J=8.3 Hz), 8.07(4H,m), 8.59(2H,d,J=5.8 Hz), 8.69(2H,brs), 11.18(1H,brs)

EXAMPLE 2

N-(4-pyridyl)-4-(1-amino-1-methylethyl)benzamide dihydrochloride (Compound 13)

(a) Thionyl chloride (0.21 ml) and dimethylformamide (2 drops) were added to a solution of 4-(1-benzyloxycarbonylamino-1-methylethyl)-benzoic acid (780 mg) in dichloromethane (10 ml), and the mixture was refluxed under heating for 1 hour. After the reaction, the solvent was evaporated under reduced pressure to give 4-(1-benzyloxycarbonylamino-1-methylethyl)benzoyl chloride as crystals. Then, the crystals were dissolved in acetonitrile (10 ml), and the solution was dropwise added to a solution of 4-aminopyridine (195 mg) and diisopropylethylamine (0.5 ml) in acetonitrile (10 ml) under ice-cooling. The mixture was stirred at room temperature for 5 hours. After the reaction, water was added, and the mixture was extracted with ethyl acetate. The extract was washed with water and dried. The solvent was evaporated under reduced pressure, and the obtained crystals were recrystallized from ethyl acetate-hexane to give 750 mg of N-(4-pyridyl)-4-(1-benzyloxycarbonylamino-1-methylethyl)benzamide.

PMR (CDCl$_3$/TMS)δ:1.64(6H,s), 5.00(2H,s), 5.28(1H,s), 7.32(5H,s), 7.47(2H,d,J=8.3 Hz), 7.58(2H,d,J=6.4 Hz), 7.76 (2H,d,J=8.3 Hz), 8.51(2H,d,J=6.3 Hz)

(b) N-(4-Pyridyl)-4-(1-benzyloxycarbonylamino-1-methylethyl)benzamide (620 mg) and 10% palladium hydroxide carbon (300 mg) were added to methanol (20 ml), and the mixture was subjected catalytic reduction in a stream of hydrogen. After the reaction, the catalyst was removed by filtration, and the mixture was concentrated under reduced pressure. A hydrochloric acid-methanol solution was added to the obtained crystals. The solvent was evaporated under reduced pressure, and the obtained crystals were recrystallized from methanolethyl acetate to give 390 mg of N-(4-pyridyl)-4-(1-amino-1-methylethyl)benzamide dihydrochloride having a melting point of 299–300° C.

PMR (DMSO-d$_6$/TMS)δ: 1.67(6H,s), 7.77(2H,d,J=8.3 Hz), 8.15(2H,d,J=8.3 Hz), 8.40(2H,d,J=6.4 Hz), 8.75(2H,d, J=6.4 Hz), 8.87(2H,s), 11.80(1H,s)

EXAMPLE 3

N-(4-pyridyl)-4-aminomethyl-2-benzyloxybenzamide monohydrochloride monohydrate (Compound 52)

(a) Thionyl chloride (1.55 ml) and dimethylformamide (2 drops) were added to a solution of 2-benzyloxy-4-benzyloxycarbonylaminomethylbenzoic acid (7.1 mg) in dichloromethane (50 ml), and the mixture was refluxed under heating for 1.5 hours. After the reaction, the solvent was evaporated under reduced pressure to give 2-benzyloxy-4-benzyloxycarbonylaminomethylbenzoyl chloride as crystals. Then, the crystals were dissolved in acetonitrile (50 ml), and the solution was dropwise added to a solution of 4-aminopyridine (1.42 g) and diisopropylethylamine (5.27 ml) in acetonitrile (50 ml) under ice-cooling. The mixture was stirred at room temperature for 4 hours. After the reaction, water was added, and the mixture was extracted with chloroform. The extract was washed with water and dried. The solvent was evaporated under reduced pressure, and the obtained crystals were recrystallized from ethyl acetate-hexane to give N-(4-pyridyl)-2-benzyloxy-4-benzyloxycarbonylaminomethylbenzamide as crystals.

PMR (CDCl$_3$/TMS)δ:4.45(2H,d,J=5.8 Hz), 5.14(2H,s), 5.15(2H,s), 7.04(4H,s), 7.42(5H,m), 7.50(5H,s), 8.24(1H,d, J=7.8 Hz), 8.33(1H,d,J=6.4 Hz), 10.06(1H,s)

(b) a 25% hydrogen bromide-acetic acid solution (1.5 ml) and acetic acid (3 ml) were added to N-(4-pyridyl)-2-benzyloxy-4-benzyloxycarbonylaminomethylbenzamide (500 mg), and the mixture was stirred at room temperature for 3 hours. After the reaction, ethyl acetate was added, and the precipitated crystals were collected by filtration under reduced pressure. A 2N aqueous sodium hydroxide solution (10 ml) was added to the crystals, and the mixture was extracted with chloroform. The extract was washed, dried, and the solvent was evaporated under reduced pressure. A hydrochloric acid-methanol solution was added to the obtained residue, and the mixture was concentrated. The obtained crystals were recrystallized from methanol-ethyl acetate to give 160 mg of N-(4-pyridyl)-4-aminomethyl-2-benzyloxybenzamide monohydrochloride monohydrate having a melting point of 203–205° C.

PMR (DMSO-$d_6$/TMS)δ: 4.11(2H,s), 5.23(2H,s), 7.19 (1H,d,J=7.8 Hz), 7.37(3H,m), 7.55(5H,m), 7.71(1H,d,J=7.8 Hz), 8.31(2H,brs), 8.43(2H,d,J=6.4 Hz), 10.52(1H,s)

EXAMPLE 4

N-(4-pyridyl)-4-aminomethyl-2-ethoxybenzamide dihydrochloride ½ hydrate (Compound 50)

(a) $Boc_2O$ (2.5 g) was added to a mixture of N-(4-pyridyl)-4-aminomethyl-2-benzyloxybenzamide monohydrochloride monohydrate (4.8 g) obtained in Example 3, diisopropylethylamine (5.9 ml), chloroform (100 ml) and dimethylimidazolidinone (50 ml), and the mixture was stirred at room temperature for 5 hours. After the reaction, chloroform was evaporated under reduced pressure. The residue was extracted with ethyl acetate, washed with water and dried. The solvent was evaporated under reduced pressure. The obtained crystals were recrystallized from methanol-ethyl acetate-hexane to give 3.38 g of N-(4-pyridyl)-2-benzyloxy-4-tert-butoxycarbonylaminomethylbenzamide.

PMR (DMSO-$d_6$/TMS)δ:1.40(9H,s), 4.18(2H,m), 5.19 (2H,s), 6.97(1H,d,J=7.8 Hz), 7.18(1H,s), 7.35(3H,m), 7.50 (5H,m), 7.62(2H,m), 8.41(2H,d,J=6.4 Hz), 10.43(1H,s)

(b) N-(4-Pyridyl)-2benzyloxy-4-tert-butoxycarbonylaminomethylbenzamide (3.38 g) was subjected to catalytic reduction using 10% palladium hydroxide carbon (1 g) in a solution of ethanol (10 ml) and dimethylimidazolidinone (70 ml) in a stream of hydrogen. After the reaction, the catalyst was removed by filtration, and the mixture was concentrated under reduced pressure to give 1.85 g of N-(4-pyridyl)-4-tert-butoxycarbonylaminomethyl-2-hydroxybenzamide.

PMR (CDCl$_3$/TMS)δ: 1.46(9H,s), 4.26(2H,m), 5.62(1H, brs), 6.87(2H,m) 7.70(2H,d,J=7.8 Hz), 7.93(2H,d,J=8.3 Hz), 8.45(2H,d,J=7.8 Hz)

(c) Potassium carbonate (40 mg) and ethyl bromide (56 mg) were added to a solution of N-(4- pyridyl)-4-tert-butoxycarbonylaminomethyl-2-hydroxybenzamide (100 mg) in dimethylformamide (10 ml), and the mixture was stirred at room temperature for 4 hours. After the reaction, water was added, and the mixture was extracted with ethyl acetate. The extract was washed with water, dried, and concentrated under reduced pressure. The obtained crystals were recrystallized form ethyl acetate-hexane to give 60 mg of N-(4- pyridyl)-4-tert-butoxycarbonylaminomethyl-2-ethoxybenzamide.

PMR (CDCl$_3$TMS)δ: 1.45(9H,s), 1.64(3H,t,J=6.8 Hz), 4.28(2H,q,J=6.8 Hz), 4.33(2H,m), 4.96(1H,brs), 6.94(1H,s), 7.01(1H,d,J=7.8 Hz), 7.56(2H,m), 8.21(1H,d,J=8.3 Hz), 8.51(2H,m), 10.24(1H,s)

(d) 4N Hydrochloric acid-dioxane (1 ml) was added to N-(4- pyridyl)-4-tert-butoxycarbonylaminomethyl-2-ethoxybenzamide (60 mg), and the mixture was stirred at room temperature for 1 hour. After the reaction, the solvent was evaporated under reduced pressure. The obtained crystals were recrystallized from methanol-ethyl acetate to give 40 mg of N-(4- pyridyl)-4-aminomethyl-2-ethoxybenzamide dihydrochloride ½ hydrate having a melting point of 251° C. (dec.).

PRM (DMSO-$d_6$/TMS)δ: 1.36(3H,t,J=6.8 Hz), 4.07(2H, m), 4.19(2H,q,J=6.8 Hz), 7.17(1H,d,J=8.3 Hz), 7.49(1H,s), 7.64(2H,d,J=8.3 Hz), 8.21(2H,d,J=7.8 Hz), 8.70(2H,s), 8.74 (2H,d,J=7.8 Hz), 11.49(1H,s)

EXAMPLE 5

(R)-(–)-N-(4- pyridyl)-4-(1-aminomethyl)-3-nitrobenzamide dihydrobromide ½ hydrate (Compound 125)

(a) Methyl (R)-4-(1-aminomethyl)benzoate (2 g) was added portionwise to a mixed solution of conc. nitric acid (1.2 ml) and conc. sulfuric acid (1.2 ml) under ice-cooling, and the mixture was stirred at room temperatue for 5 hours. The reaction mixture was poured into ice-water, and extracted with chloroform. The extract was washed with water, dried, and concentrated under reduced pressure. The obtained crystals were recrystallized from ethyl acetate-hexane to give 1.4 g of methyl (R)-4-(1-acetamidoethyl)-3-nitrobenzoate.

PMR (CDCl$_3$/TMS)δ: 1.55(3H,d,J=6.8 Hz), 1.95(3H,s), 3.93(3H,s), 5.42–5.49(1H,m), 6.00–6.04(1H,br), 7.57(1H,d, J=8.3 Hz), 8.18(1H,dd,J=1.4,8.3 Hz), 8.48(1H,d,J=1.4 Hz)

(b) Methyl (R)-4-(1-acetamidoethyl)-3-nitrobenzoate (650 mg) was dissolved in 2N hydrochloric acid, and the mixture was refluxed for 2 hours. After the reaction, the reaction mixture was evaporated under reduced pressure, and further boiled with toluene, which was followed by drying to give 620 mg of (R)-4-(1-aminoethyl)-3-nitrobenzoic acid hydrochloride.

PMR (DMSO-$d_6$/TMS)δ: 1.60(3H,d,J=6.4 Hz), 4.85–4.88(1H,br), 8.12(1H,d,J=8.3 Hz), 8.32(1H,dd,J=1.5, 8.3 Hz), 8.43(1H,d,J=1.5 Hz), 8.66–8.72(3H,br)

(c) Benzyloxycarbonyl chloride (0.9 g) was dropwise added to an aqueous solution (10 ml) of (R)-4-(1-aminoethyl)-3-nitrobenzoic acid hydrochloride (1 g) and sodium hydroxide (535 mg) at room temperature, and the mixture was stirred at the same temperature for 3 hours. Conc. hydrochloric acid was added to the reaction mixture to make the same acidic. The mixture was extracted with chloroform. The extract was washed with water, dried, and concentrated. The obtained residue was purified by silica gel column chromatography (chloroform:methanol=10:1) to give 1.05 g of (R)-4-(1-benzyloxycarbonylaminoethyl)-3-nitrobenzoic acid.

PMR (CDCl$_3$/TMS)δ: 1.31(3H,d,J=6.8 Hz), 4.93–5.09 (3H,m), 7.28–7.37(5H,m), 7.84(1H,d,J=8.3 Hz), 8.25–8.29 (2H,m), 8.44(1H,d,J=1.5 Hz)

(d) Thionyl chloride (5 ml) and dimethylformamide (1 drop) were added to a solution of (R)-4-(1-benzyloxycarbonylaminoethyl)-3-nitrobenzoic acid (1 g) in dichloromethane (5 ml), and the mixture was refluxed for 3 hours. After the reaction, the solvent was evaporated under reduced pressure to give (R)-4-(1-benzyloxycarbonylaminoethyl)-3-nitrobenzoyl chloride as crystals. Then, the crystals were dissolved in dichloromethane (14 ml). The solution was dropwise added to a solution of 4-aminopyridine (250 mg) and diisopropylethylamine (375 mg) in dichloromethane (6 ml) under ice-cooling, and the mixture was stirred at room temperatue for 4 hours. After the reaction, water was added to the reaction mixture, and the mixture was extracted with chloroform. The extract was dried and the solvent was evaporated under reduced pressure. The obtained residue was purified by silica gel column chromatography (chloroform:methanol=15:1) to give 940 mg of (R)-N-(4-pyridyl)-4-(1-benzyloxycarbonylaminoethyl)-3-nitrobenzamide.

PMR (DMSO-d$_6$/TMS) δ: 1.45(3H,d,J=6.8 Hz), 4.90(1H, d,J=12.2 Hz), 4.97(1H,d,J=12.2 Hz), 5.03–5.09(1H,m), 7.28–7.36(5H,m), 7.75(2H,d,J=6.4 Hz), 7.84(1H,d,J=8.3 Hz), 8.25–8.29(2H,m), 8.44(1H,d,J=1.5 Hz), 8.50(2H,d,J= 6.4 Hz), 10.78(1H,s)

(e) A 25% hydrogen bromide-acetic acid solution (4 ml) was added to (R)-N-(4-pyridyl)-4-(1-benzyloxycarbonylaminoethyl)-3-nitrobenzamide (400 mg), and the mixture was stirred at room temperature for 1 hour. After the reaction, the reaction mixture was evaporated under reduced pressure. The obtained crystals were washed with ethyl acetate, and recrystallized from methanol to give 153 mg of (R)-(−)-N-(4-pyridyl)-4-(1-aminoethyl)-3-nitrobenzamide dihydrobromide ½ hydrate having a melting point of 275° C. (dec.).

[α]$_D$=−7.9° (methanol, c=1)

PMR (DMSO-d$_6$/TMS) δ: 1.62(3H,d,J=6.8 Hz), 4.91–4.95(1H,br), 8.15(1H,d,J=8.3 Hz), 8.34(2H,d,J=6.8 Hz), 8.52(4H,m), 8.66(1H,d,J=2.0 Hz), 8.82(2H,d,J=6.8 Hz), 11.78(1H,s)

EXAMPLE 6

(R)-(−)-N-(4-pyridyl)-3-amino-4-(1-aminoethyl) benzamide trihydrochloride 3/2 hydrate (Compound 127)

(R)-N-(4-Pyridyl)-4-(1-benzyloxycarbonylaminoethyl)-3-nitrobenzamide (540 mg) was stirred in a stream of hydrogen at 40° C. for 4 hours using 10% palladium hydroxide carbon (250 mg) in methanol (20 ml) solution. After the reaction, the catalyst was removed by filtration, and the mixture was concentrated under reduced pressure. The obtained residue was converted to hydrochloride thereof using 15% hydrochloric acid-methanol, and recrystallized from methanol to give 130 mg of (R)-(−)-N-(4-pyridyl)-3-amino-4-(1-aminoethyl)benzamide trihydrochloride 3/2 hydrate having a melting point of 210° C. (dec.).

[α]$_D$=−6.1° (methanol, c=1)

PMR (DMSO-d$_6$/TMS)δ: 1.46(3H,d,J=6.3Hz), 4.60–4.64 (1H,br), 7.41(1H,s), 7.48–7.51(1H,m), 7.56(1H,d,J=7.8Hz), 8.37(2H,d,J=6.9Hz), 8.40–8.70(2H,br), 8.75(2H,d,J= 6.9Hz), 11.66(1H,s)

EXAMPLE 7

(R)-(+)-N-(4-pyridyl)-4-(1-aminoethyl)-3-chlorobenzamide dihydrobromide (Compound 141)

(a) Methyl (R)-4-(1-acetamidoethyl)-3-nitrobenzoate (1 g) was stirred in a stream of hydrogen at room temperature for 3 hours using 10% palladium hydroxide carbon (0.3 g) in a methanol (20 ml) solution. After the reaction, the catalyst was removed by filtration, and the solvent was evaporated under reduced pressure to give 0.89 g of methyl (R)-3-amino-4-(1-acetamidoethyl)benzoate.

PMR DMSO-d$_6$/TMS)δ: 1.30(3H,d,J=6.79Hz), 1.82(3H, s), 3.78(3H,s), 4.93–5.01(1H,m), 5.31–5.33(2H,br), 7.11 (1H,dd,J=4,8.3Hz), 7.17(1H,d,J=8.3Hz), 7.27(1H,d,J= 1.4Hz), 8.26(1H,d,J=8.3Hz)

(b) A solution of methyl (R)-3-amino-4-(1-acetamidoethyl)benzoate (600 mg) in acetic acid (6 ml) was dropwise added to a solution of sodium nitrite (193mg) in conc. sulfuric acid (2 ml) at room temperature, and the mixture was stirred at room temperature for 30 minutes. The reaction mixture was dropwise added to a solution of copper(I) chloride (550 mg) in conc. hydrochloric acid (6 ml) under ice-cooling, and the mixture was stirred at room temperature for 5 hours. After the reaction, the reaction mixture was poured into ice water, dried, and concentrated. The obtained residue was purified by silica gel column chromatography (chloroform:methanol=30:1) to give 460 mg of methyl (R)-4-(1-acetamidoethyl)-3-chlorobenzoate.

PMR (CDCl$_3$/TMS)δ: 1.46(3H,d,J=6.8Hz), 1.99(3H,s), 3.89(3H,s), 5.33–5.40(1H,m), 5.92–5.98(1H,br), 7.36(1H,d, J=8.3Hz), 7.87(1H,dd,J=1.5,8.3Hz), 8.00(1H,d,J=1.5Hz)

(c) Methyl (R)-4-(1-acetamidoethyl)-3-chlorobenzoate (630 mg) was added to 2N hydrochloric acid (15 ml), and the mixture was refluxed for 3 hours. After the reaction, the solvent was evaporated under reduced pressure. The residue was further boiled with toluene, and dried to give 700 mg of (R)-4-(1-aminoethyl)-3-chlorobenzoic acid hydrochloride.

PMR (DMSO-d$_6$/TMS)δ: 1.51(3H,d,J=6.8Hz), 4.67–4.74 (1H,m), 7.89(1H,d,J=8.3Hz), 7.95–7.99(2H,m), 7.80–7.86 (3H,br)

(d) Benzyloxycarbonyl chloride (750 mg) was dropwise added to an aqueous solution (10 ml) of (R)-4-(1-aminoethyl)-3-chlorobenzoic acid hydrochloride (690 mg) and sodium hydroxide (410 mg) at room temperature, and the mixture was stirred for 3 hours. After the reaction, conc. hydrochloric acid was added to the reaction mixture to make the same acidic, and the mixture was extracted with chloroform. The extract was dried, and the solvent was evaporated under reduced pressure. The obtained residue was purified by silica gel column chromatography (chloroform:methanol=30:1) to give 680 mg of (R)-4-(1-benzyloxycarbonylaminoethyl)-3-chlorobenzoic acid.

PMR (DMSO-d$_6$/TMS)δ: 1.31(3H,d,J=6.8Hz), 4.93–5.06 (3H,m), 7.28–7.37(5H,m), 7.56(1H,d,J=8.3Hz), 7.85–7.90 (2H,m), 8.12(1H,d,J=7.92Hz).

(e) Thionyl chloride (5 ml) and dimethylformamide (1 drop) were added to a solution of (R)-4-(1-benzyloxycarbonylaminoethyl)-3-chlorobenzoic acid (680 mg) in dichloromethane (7 ml), and the mixture was stirred at room temperature for 4 hours. After the reaction, the solvent was evaporated under reduced pressure to give (R)-4-(1-benzyloxycarbonylaminoethyl)-3-chlorobenzoyl chloride as crystals. Then, the crystals were dissolved in dichloromethane (12 ml). The solution was dropwise added to a solution of 4-aminopyridine (187 mg) and diisopropylethylamine (267 mg) in dichloromethane (5 ml) at room temperature, and the mixture was stirred for 1 hour. After the reaction, water was added to the reaction mixture. The mixture was extracted with chloroform, washed with water and dried. The solvent was evaporated under reduced pressure, and the obtained residue was purified by silica gel column chromatography (chloroform:methanol=20:1) to give 650 mg of (R)-4-(4-pyridyl)-4-(1-benzyloxycarbonylaminoethyl)-3-chlorobenzamide.

PMR (CDCl$_3$/TMS)δ: 1.43(3H,d,J=6.8Hz), 5.03–5.17 (3H,m), 5.27–5.31(1H,br), 7.24–7.42(5H,m), 7.59(2H,d,J= 6.4Hz), 7.73(1H,m), 7.78(1H,s), 8.27–8.31(1H,br), 8.52 (2H,d,J=6.4)

(f) A 25% hydrogen bromide-acetic acid solution (7 ml) was added to (R)-N-(4-pyridyl)-4-(1benzyloxycarbonylaminoethyl)-3-chlorobenzamide (630 mg), and the mixture was stirred at room temperature for 6 hours. After the reaction, the solvent was evaporated under reduced pressure. The obtained crystals were washed with ether, and recrystallized from methanol to give 243 mg of (R)-(+)-N-(4-pyridyl)-4-(1aminoethyl)-3-chlorobenzamide dihydrobromide having a melting point of more than 300° C.

[α]$_D$=+4.0° (methanol,c=1)

PMR (DMSO-d$_6$/TMS)δ: 1.52(3H,d,J=6.8Hz), 4.76–4.84 (1H,m), 7.88(1H,d,J=8.3Hz), 8.12(1H,d,J=8.3Hz), 8.19(1H, d,J=2.0Hz), 8.30(2H,d,J=6.9Hz), 8.53–8.57(3H,br), 8.79 (2H,d,J=6.9Hz), 11.58(1H,s)

EXAMPLE 8

N-(4-pyridyl)-3-aminomethylbenzamide dihydrochloride monohydrate (Compound 21)

(a) Thionyl chloride (10 ml) and dimethylformamide (1 drop) were added to a solution of 3-cyanobenzoic acid (10 ml) in dichloromethane (100 ml), and the mixture was refluxed for 3 hours. After the reaction, the solvent was evaporated under reduced pressure to give 3-cyanobenzoyl chloride. Then, the oil was dissolved in dichloromethane (25 ml), and the solution was dropwise added to a solution of 4-aminopyridine (5 g) and diisopropylethylamine (8.9 g) in dichloromethane (50 ml), which was followed by stirring at room temperature for 1 hour. The precipitated crystals were collected by filtration, and recrystallized from chloroform-methanol,ether to give 5.3 g of N-(4-pyridyl)-3-cyanobenzamide.

PMR (DMSO-d$_6$/TMS)δ: 7.81(1H,t,J=7.8Hz), 8.16(1H,d, J=7.8Hz), 8.34–8.37(3H,m), 8.55(1H,s), 8.77(2H,d,J= 7.32Hz), 11.90(1H,s)

(b) A solution of N-(4-pyridyl)-3-cyanobenzamide (2 g), Raney nickel (0.5 g) and 2 moles of a sodium hydroxide solution (8 ml) in ethanol (20 ml) were stirred in an autoclave at 10 atm hydrogen initial pressure at room temperature for 5 hours. After the reaction, the catalyst was removed by filtration, and the filtrate was concentrated to ⅓ under reduced pressure. The obtained solution was diluted with water, and extracted with chloroform:methanol (10:1). The extract was dried, and the solvent was evaporated under reduced pressure. The obtained residue was purified by silica gel column chromatography (chloroform:methanol=10:1). The obtained oil was converted to hydrochloride thereof with 15% hydrochloric acid-methanol, and the hydrochloride was recrystallized from methanol-ether to give 620 mg of N-(4-pyridyl)-3-aminomethylbenzamide dihydrochloride monohydrate having a melting point of 273–276° C.

PMR (DMSO-d$_6$/TMS_δ: 4.13–4.16(2H,m), 7.64(1H,t,J= 7.8Hz), 7.79(1H,d,J=7.8Hz), 8.10(1H,d,J=7.8Hz), 8.30(1H, s), 8.42(2H,d,J=6.8Hz), 8.43–8.55(3H,br), 8.76(2H,d,J= 6.8Hz), 11.83(1H,s)

EXAMPLE 9

(R)-(+)-N-(1-pyrrolo[2,3-b]pyridin-4-yl)-4-(1-aminoethyl)-benzamide dihydrochloride 3/2 hydrate (Compound 230)

(a) Thionyl chloride (0.9 ml) and dimethylformamide (1 drop) were added to a solution of (R)-4-(1-benzyloxycarbonylaminoethyl)bonzoic acid (1.2 g) in dichloromethane (15 ml), and the mixture was stirred at room temperature for 2 hours. After the reaction, the solvent was evaporated under reduced pressure to give (R)-4-(1-benzyloxycarbonylaminoethyl)benzoyl chloride as crystals. Then, the crystals were dissolved in acetonitrile (10 ml), and the solution was dropwise added to a solution of 4-amino-1H-pyrrolo[2,3-b]pyridine (240 mg) and diisopropylethylamine (520 mg) in acetronitrile (10 ml). The mixture was stirred at room temperature for 8 hours. The precipitated crystals were collected by filtration, dried, and dissolved in methanol (7 ml). Sodium methoxide (60 mg) was added, and the mixture was stirred at room temperature for 30 minutes. After the reaction, the mixture was concentrated under reduced pressure, and water was added to the obtained residue. The mixture was extracted with ethyl acetate and dried. The solvent was evaporated under reduced pressure, and the obtained crystals were washed with ethyl acetate to give 330 mg of (R)-N-(1H-pyrrolo[2,3-b]pyridin-4-yl)-4-(1-benzyloxycarbonylaminoethyl)benzamide.

PMR (DMSO-d$_6$/TMS)δ: 1.33–1.40(3H,m), 4.72–4.78 (1H,m), 4.98–5.04(2H,m), 6.78–6.82(1H,m), 7.32–8.16 (13H,m)

(b) 10% Palladium hydroxide carbon (80 mg) was added to a mixture of (R)-N-(1H-pyrrolo[2,3-b]pyridin-4-yl)-4-(1-benzyloxycarbonylaminoethyl)benzamide (200 mg), 15% hydrochloric acid-methanol (1 ml) and methanol (6 ml), and the mixture was stirred in a stream of hydrogen at 40° C. for 1 hour. After the reaction, the catalyst was removed by filtration, and the mixture was concentrated under reduced pressure. The obtained crystals were recrystallized from methanol-ether to give 120 mg of (R)-(+)-N-(1H-pyrrolo[2, 3-b]pyridin-4-yl)-4-(1-aminoethyl)benzamide dihydrochloride 3/2 hydrate having a melting point of 286° C. (dec.).

[α]$_D$=+6.1° (methanol,c=1)

PMR (DMSO-d$_6$/TMS)δ: 1.54(3H,d,J=6.8Hz), 4.50–4.54 (1H,m), 7.11(1H,br), 7.55(1H,br), 7.70(2H,d,J=8.3Hz), 8.02–8.06(3H,m) 8.33(1H,br), 8.62(3H,br), 10.99(1H,br)

EXAMPLE 10

(R)-(+)-N-(1pyrazolo[3,4-b]pyridin-4-yl)-4-(1-aminoethyl)benzamide dihydrochloride monohydrate (Compound 238)

(a) Thionyl chloride (2 ml) and dimethylformamide (1 drop) were added to a solution of (R)-4-(1-benzyloxycarbonylaminoethyl)benzoic acid (1.11 g) in dichloromethane (10 ml), and the mixture was stirred at room temperature for 2 hours. After the reaction, the solvent was evaporated under reduced pressure to give (R)-4-(1benzyloxycarbonylaminoethyl)benzoyl chloride as crystals. Then, the crystals were dissolved in acetonitrile (10 ml), and the solution was dropwise added to a mixed solution of 4-amino-1h-pyrazolo[3,4-b]pyridine hydrochloride (320 mg) and diisopropylethylamine (880 mg) in acetonitrile (10 ml)-dimethylimidazolidinone (3 ml). The mixture was stirred at room temperature for 5 hours. The precipitated crystals were collected by filtration and dried. The residue was dissolved in methanol (7 ml). Sodium methoxide (80 mg) was added, and the mixture was stirred at room temperature for 30 minutes. After the reaction, the mixture was concentrated under reduced pressure, and water was added to obtained residue. The mixture was extracted with ethyl acetate and dried. The solvent was evaporated under reduced pressure, and the obtained crystals were washed with ethyl acetate to give 310 mg of (R)-N-(1Hpyrazolo[3,4-b]pyridin-4-yl)-4-(1-benzyloxycarbonylaminoethyl)benzamide.

PMR (DMSO-d$_6$/TMS)δ: 1.37(3H,d,J=6.8Hz), 4.73–4.79 (1H,m), 4.97(1H,d,J=12.2Hz), 5.03(1H,d,J=12.2Hz), 7.33–7.37(5H,m), 7.49(2H,d,J=8.3Hz), 7.71(1H,d,J= 5.4Hz), 7.90–7.95(3H,m), 8.39–8.42(2H,m), 10.76(1H,s), 13.53(1H,s)

(b) 10% Palladium hydroxide carbon (100 mg) was added to a mixture of (R)-N-(1H-pyrazolo[3,4-b]pyridin-4-yl)-4-(1benzyloxycarbonylaminoethylbenzamide (300 mg), 15% hydrochloric acid-methanol (3 ml) and methanol (14 ml), and the mixture was stirred in a stream of hydrogen at 40° C. for 1 hour. After the reaction, the catalyst was removed by filtration, and the mixture was concentrated under reduced pressure. The obtained crystals were recrystallized from methanol-ether to give 120 mg of (R)-(+)-N-(1H-pyrazolo[3,4-b]pyridin-4-yl)-4-(1aminoethyl)benzamide dihydrochloride monohydrate having a melting point of 259° C. (dec.).

$[\alpha]_D$=+4.4° (methanol, c=1)

PMR (DMSO-$d_6$/TMS)δ: 1.54(3H,d,J=6.9Hz), 4.49–4.55 (1H,m), 7.72(2H,d,J=8.3Hz), 7.85(1H,br), 8.07(2H,d,J=8.3Hz), 8.55(1H,br), 8.71(3H,br), 11.27(1H,br)

EXAMPLE 11

N-(1H-pyrazolo[3,4-b]pyridin-4-yl)-4-guanidinomethylbenzamide dihydrochloride monohydrate (Compound 482)

(a) Thionyl chloride (12 ml) and dimethylformamide (1 drop) were added to a solution of 4-benzyloxycarbonylaminomethylbenzoic acid (2.85 g) in dichloromethane (12 ml), and the mixture was stirred at room temperature for 2 hours. After the reaction, the solvent was evaporated under reduced pressure to give 4-benzyloxycarbonylaminomethylbenzoyl chloride as crystals. Then, the crystals were dissolved in acetonitrile (5 ml), and the solution was dropwise added to a mixed solution of 4-amino-1H-pyrazolo[3,4-b]pyridine 2 trifluoroacetate (1.09 g) and diisopropylethylamine (1.7 g) in acetonitrile (10 ml-dimethylformamide (5 ml). The mixture was stirred at room temperature for 3 hours. Water was added to the reaction mixture and acetonitrile was evaporated under reduced pressure. The residue was extracted with ethyl acetate, dried and the solvent was evaporated under reduced pressure. The obtained residue was dissolved in methanol (10 ml) and sodium methoxide (80 mg) was added, which was followed by stirring at room temperature for 4 hours. After the completion of the reaction, insoluble matter was filtered off and the filtrate was concentrated under reduced pressure. Water was added to the obtained residue and the mixture was extracted with chloroform:methanol=10:1. The extract was dried and the solvent was evaporated under reduced pressure. The obtained crystals were washed with ethyl acetate to give 540 mg of N-(1H-pyrazolo[3,4-b]pyridin-4-yl)-4-benzyloxycarbonylaminomethylbenzamide.

PMR (DMSO-$d_6$/TMS)δ: 4.29(2H,br), 5.06(2H,s), 7.30–7.40(5H,m), 7.44(2H,d,H=7.8Hz), 7.69(1H,d,J=4.9Hz), 7.91–7.97(3H,m), 8.39–8.44(2H,m), 10.77(1H,br), 13.53(1H,br)

(b) 10% Palladium hydroxide carbon (250 mg) was added to a mixture of N-(1H-pyrazolo[3,4-b]pyridin-4-yl)-4-benzyloxycarbonylaminomethylbenzamide (540 mg), 15% hydrochloric acid-methanol (3 ml) and methanol (10 ml), and the mixture was stirred in a stream of hydrogen at 40° C. for 2 hours. After the reaction, the catalyst was removed by filtration, and the mixture was concentrated under reduced pressure. The obtained crystals were recrystallized from ethanol-ethyl acetate to give 330 mg of N-(1H-pyrazolo[3,4-b]pyridin-4-yl)-4-aminomethylbenzamide dihydrochloride.

PMR (DMSO-$d_6$/TMS)δ: 4.11–4.16(2H,m), 7.70(2H,d,J=8.3Hz), 7.89(1H,br), 8.08(2H,d,J=8.3Hz), 8.55–8.80(5H,m), 11.37(1H,m)

(c) Pyrazole-1-carboxyamidine hydrochloride (284 mg) was added to a mixed solution of N-(1H-pyrazolo[3,4-b]pyridin-4-yl)-4-aminoethylbanzamide dihydrochloride (330 mg) and diisopropylethylamine (500 mg) in methanol (5 ml)-dimethylformamide (5 ml), and the mixture was stirred in a stream of nitrogen at room temperature for 8 hours. After the reaction, the reaction mixture was concentrated under reduced pressure. The obtained residue was purified by silica gel column chromatography (chloroform:methanol=3:1) to give white crystals. The crystals were converted to hydrochloride thereof with 15% hydrochloric acid-methanol, and the hydrochloride was recrystallized from methanol-ether to give 205 mg of N-(1H-pyrazolo[3,4-b]pyridin-4-yl)-4-guanidinomethylbenzamide dihydrochloride monohydrate having a melting point of 250–254° C. (dec.)

PMR (DMSO-$d_6$/TMS)δ: 4.52(2H,br), 7.40(2H,br), 7.50 (2H,d,J=8.3Hz), 7.85(1H,br), 8.03(2H,d,J=8.3Hz), 8.34(1H, br), 8.55(2H,br)

EXAMPLE 12

N-(4-pyridyl)-4-guanidinomethylbenzamide monohydrochloride monohydrate (Compound 395)

Pyrazole-1-carboxyamidine hydrochloride (540 mg) was added to a solution of N-(4-pyridyl)-4-aminomethylbenzamide dihydrochloride (550 mg) and diisopropylethylamine (950 mg) in methanol (7 ml), and the mixture was stirred in a stream of nitrogen at room temperature for 6 hours. After the reaction, the reaction mixture was concentrated to half under reduced pressure, and ethyl acetate was added to precipitate crystals. The crystals were collected by filtration, and recrystallized from methanol-ethyl acetate to give 333 mg of N-(4-pyridyl)-4-guanidinomethylbenzamide monohydrochloride monohydrate having a melting point of 244–248° C.

PMR (DMSO-$d_6$/TMS)δ: 4.49(2H,d,J=6.3Hz), 7.43(2H, br), 7.47(2H,d,J=8.3 Hz), 7.96(2H,d,J=6.4 Hz), 8.02(2H,d, J=8.3 Hz), 8.21(1H,br), 8.55(2H,d,J=6.4 Hz), 10.95(1H,br)

EXAMPLE 13

(R)-(+)-N-(4-pyridyl)-4-(1-aminoethyl)-3-fluorobenzamide dihydrobromide (Compound 139)

(a) Sodium nitrate (640 mg) was added to a solution of methyl (R)-3-amino-4-(1-acetamidoethyl)benzoate (2 g) in hydrogen fluoride-pyridine (20 ml) under ice-cooling, and the mixture was stirred at room temperature for 1 hour. After the reaction, the reaction mixture was poured into ice water and extracted with chloroform. The extract was washed with water, dried and concentrated. The obtained residue was purified by silica gel column chromatography (chloroform:methanol=50:1) to give 690 mg of methyl (R)-4-(1-acetamidoethyl)-3-fluorobenzoate.

PMR (CDCl$_3$/TMS) δ: 1.46(3H,d,J=6.8 Hz), 1.97(3H,s), 3.88(3H,s), 5.22–5.29(1H,m), 6.05(1H,br), 7.32(1H,t,J=7.8 Hz), 7.66(1H,dd,J=1.5,11.2 Hz), 7.75(1H,dd,J=1.5,8.3 Hz)

(b) Methyl (R)-4-(1-acetamidoethyl)-3-fluorobenzoate (690 mg) was added to 2N hydrochloric acid (15 ml), and the mixture was refluxed for 3 hours. After the reaction, the reaction mixture was evaporated under reduced pressure, further boiled with toluene, and dried to give (R)-4-(1-aminoethyl)-3-fluorobenzoic acid hydrochloride (620 mg).

PMR (DMSO-$d_6$/TMS) δ: 1.53(3H,d,J=6.8 Hz), 4.63(1H, br), 7.70(1H,d,J=10.7 Hz), 7.84(2H,m), 8.79(3H,br), 13.38 (1H,br)

(c) Benzyloxycarbonyl chloride (710 mg) was dropwise added to an aqueous solution (10 ml) of (R)-4-(1- aminoethyl)-3-fluorobenzoic acid hydrochloride (610 mg) and sodium hydroxide (390 mg), and the mixture was stirred at room temperature for 4 hours. After the reaction, conc. hydrochloric acid was added to the reaction mixture to make the same acidic, and the mixture was extracted with chloroform. The mixture was dried and the solvent was evaporated under reduced pressure. The obtained residue was purified by silica gel column chromatography (chloroform:methanol=40:1) to give 520 mg of (R)-4-(1-benzyloxycarbonylaminoethyl)-3-fluorobenzoic acid.

PMR (DMSO-$D_6$/TMS) δ: 1.33(3H,d,J=7.3 Hz), 4.93–5.03(3H,m), 7.30–7.35(5H,m), 7.47(1H,t,J=7.8 Hz), 7.58(1H,d,J=10.8 Hz), 7.74(1H,d,J=8.3 Hz), 8.02(1H,d,J=7.8 Hz)

(d) Thionyl chloride (7 ml) and dimethylformamide (1 drop) were added to a solution of (R)-4-(1-benzyloxycarbonylaminoethyl)-3-fluorobenzoic acid (520 mg) in dichloromethane (7 ml), and the mixture was stirred at room temperature for 4 hours. After the reaction, the solvent was evaporated under reduced pressure to give (R)-4-(1-benzyloxycarbonylaminoethyl)-3-fluorobenzoyl chloride as crystals. Then, the crystals were dissolved in dichloromethane (12 ml), and the solution was dropwise added to a solution of 4-aminopyridine (140 mg) and diisopropylethylamine (210 mg) in dichloromethane (5 ml) at room temperature, and the mixture was stirred for 1 hour. After the reaction, water was added to the reaction mixture, and the mixture was extracted with chloroform. The mixture was washed with water and dried. The solvent was evaporated under reduced pressure, and the obtained residue was purified by silica gel column chromatography (chloroform:methanol=20:1) to give 560 mg of (R)-N-(4-pyridyl)-4-(1-benzyloxycarbonylaminoethyl)-3-fluorobenzamide.

PMR (DMSO-$d_6$/TMS) δ: 1.36(3H,d,J=7.3 Hz), 4.99(3H, m), 7.34(5H,m). 7.55(1H,t,J=7.8 Hz), 7.75(4H,m), 8.04(1H, d,J=7.8 Hz, 8.47(2H,d,J=5.4 Hz), 10.57(1H,s)

(e) A 25% hydrogen bromide-acetic acid solution (8 ml) was added to (R)-N-(4-pyridyl)-4-(1-benzyloxycarbonylaminoethyl)-3-fluorobenzamide (550 mg), and the mixture was stirred at room temperature for 3 hours. After the reaction, the solvent was evaporated under reduced pressure. The obtained crystals were washed with ether, and recrystallized from methanol to give 350 mg of (R)-(+)-N-(4-pyridyl)-4-(1-aminoethyl)-3-fluorobenzamide dihydrobromide having a melting point of 294° C. (dec.).

$[α]_D$=+4.2° (methanol, c=1)

PMR (DMSO-$d_6$/TMS) δ: 1.54(3H,d,J=6.9 Hz), 4.74(1H, m), 7.83(1H,t,J=7.8 Hz), 7.98(2H,m), 8.33(2H,d,J=6.8 Hz), 8.51(3H,br), 8.80(2H,d,J=6.8 Hz), 11.57(1H,s)

EXAMPLE 14
N-(4-pyridyl)-4-aminomethylbenzamide dihydrochloride, m.p. 300–301° C. (Compound 1)

EXAMPLE 15
N-(4-pyridyl)-4-aminomethyl-2-hydroxybenzamide dihydrochloride 1/2 hydrate, m.p. 279° C. (dec.) (Compound 46)

EXAMPLE 16
N-(4-pyridyl)-4-(2-aminoethyl)benzamide dihydrochloride 1/2 hydrate, m.p. 286° C. (dec.) (Compound 18)

EXAMPLE 17
N-(4-pyridyl)-4-aminomethyl-3-nitrobenzamide dihydrobromide 1/2 hydrate, m.p. 284° C. (dec.) (Compound 53)

EXAMPLE 18
N-(4-pyridyl)-3-amino-4-aminomethylbenzamide trihydrochloride, m.p. 270° C. (dec.) (Compound 55)

EXAMPLE 19
(S)-(−)-N-(4-pyridyl)-4-(1-aminoethyl)benzamide dihydrochloride, m.p. 278–279° C. $[α]_D$=−5.6° (methanol, c=1) (Compound 2, S-configuration)

EXAMPLE 20
(S)-(−)-N-(4-pyridyl)-2-(1-aminoethyl)benzamide dihydrochloride, m.p. 193–195° C., $[α]_D$=−3.2° (methanol, c=1) (Compound 34, S-configuration)

EXAMPLE 21
N-(1H-pyrazolo[3,4-b]pyridin-4-yl)-3-amino-4-(1-aminoethyl)benzamide

EXAMPLE 22
N-(1H-pyrrolo[2,3-b]pyridin-4-yl)-3-amino-4-(1-aminoethyl)benzamide

EXAMPLE 23
N-(4-pyridyl)-4-(1-aminoethyl)-3-fluorobenzamide

EXAMPLE 24
N-(4-pyridyl)-4-(1-amino-1-methylethyl)-3-fluorobenzamide

EXAMPLE 25
N-(4-pyridyl)-4-(1-aminoethyl)-3-chlorobenzamide

EXAMPLE 26
N-(4-pyridyl)-4-(1-amino-1-methylethyl)-3-chlorobenzamide

EXAMPLE 27
N-(1H-pyrazolo[3,4-b]pyridin-4-yl)-4-(1-aminoethyl)-3-chlorobenzamide EXAMPLE 28
N-(1H-pyrazolo[3,4-b]pyridin-4-yl)-4-(1-amino-1-methylethyl)-3-chlorobenzamide EXAMPLE 29
N-(1H-pyrrolo[2,3b]pyridin-4-yl)-4-(1-aminoethyl)-3-chlorobenzamide EXAMPLE 30
N-(1H-pyrrolo[2,3-b]pyridin-4-yl)-4-(1-amino-1-methylethyl)-3-chlorobenzamide EXAMPLE 31
N-(1H-pyrazolo[3,4-b]pyridin-4-yl)-4-(1-aminoethyl)-3-fluorobenzamide EXAMPLE 32
N-(1H-pyrazolo[3,4-b]pyridin-4-yl)-4-(1-amino-1-methylethyl)-3-fluorobenzamide EXAMPLE 33
N-(1H-pyrrolo[2,3-b]pyridin-4-yl)-4-(1-aminoethyl)-3-fluorobenzamide

EXAMPLE 34
N-(1H-pyrrolo[2,3-b]pyridin-4-yl)-4-(1-amino-1-methylethyl)-3-fluorobenzamide

EXAMPLE 35
N-(4-pyridyl)-4-(1-aminoethyl)-3-bromobenzamide

EXAMPLE 36
N-(4-pyridyl)-4-(1-amino-1-methylethyl)-3-bromobenzamide

EXAMPLE 37
N-(1H-pyrazolo[3,4-b]pyridin-4-yl)-4-(1-aminoethyl)-3-bromobenzamide

EXAMPLE 38
N-(1H-pyrazolo[3,4-b]pyridin-4-yl)-4-(1-amino-1-methylethyl)-3-bromobenzamide

EXAMPLE 39
N-(1H-pyrrolo[2,3-b]pyridin-4-yl)-4-(1-aminoethyl)-3-bromobenzamide

EXAMPLE 40
N-(1H-pyrrolo[2,3-b]pyridin-4-yl)-4-(1-amino-1-methylethyl)-3-bromobenzamide

EXAMPLE 41
N-(4-pyridyl)-4-(1-aminoethyl)-3-methylbenzamide

EXAMPLE 42
N-(4-pyridyl)-4-(1-amino-1-methylethyl)-3-methylbenzamide

EXAMPLE 43
N-(1H-pyrazolo[3,4-b]pyridin-4-yl)-4-(1-aminoethyl)-3-methylbenzamide

EXAMPLE 44
N-(1H-pyrazolo[3,4-b]pyridin-4-yl)-4-(1-amino-1-methylethyl)-3-methylbenzamide

EXAMPLE 45
N-(1H-pyrrolo[2,3-b]pyridin-4-yl)-4-(1-aminoethyl)-3-methylbenzamide

EXAMPLE 46
N-(1H-pyrrolo[2,3-b]pyridin-4-yl)-4-(1-amino-1-methylethyl)-3-methylbenzamide

EXAMPLE 47
N-(4-pyridyl)-4-(1-aminoethyl)-3-ethylbenzamide

EXAMPLE 48
N-(4-pyridyl)-4-(1-amino-1-methylethyl)-3-ethylbenzamide

EXAMPLE 49
N-(1H-pyrazolo[3,4-b]pyridin-4-yl)-4-(1-aminoethyl)-3-ethylbenzamide

EXAMPLE 50
N-(1H-pyrazolo[3,4-b]pyridin-4-yl)-4-(1-amino-1-methylethyl)-3-ethylbenzamide

EXAMPLE 51
N-(1H-pyrrolo[2,3-b]pyridin-4-yl)-4-(1-aminoethyl)-3-ethylbenzamide

EXAMPLE 52
N-(1H-pyrrolo[2,3-b]pyridin-4-yl)-4-(1-amino-1-methylethyl)-3-ethylbenzamide

EXAMPLE 53
N-(4-pyridyl)-4-(1-aminoethyl)-3-propylbenzamide

EXAMPLE 54
N-(4-pyridyl)-4-(1-aminoethyl)-3-cyanobenzamide

EXAMPLE 55
N-(4-pyridyl)-4-(1-amino-1-methylethyl)-3-cyanobenzamide

EXAMPLE 56
(R)-N-(1H-pyrazolo[3,4-b]pyridin-4-yl)-4-(1-aminoethyl)-3-cyanobenzamide

EXAMPLE 57
N-(1H-pyrazolo[3,4-b]pyridin-4-yl)-4-(1-amino-1-methylethyl)-3-cyanobenzamide

EXAMPLE 58
N-(1H-pyrrolo[2,3-b]pyridin-4-yl)-4-aminomethyl-3-cyanobenzamide

EXAMPLE 59
N-(1H-pyrrolo[2,3-b]pyridin-4-yl)-4-(1-aminoethyl)-3-cyanobenzamide

EXAMPLE 60
N-(1H-pyrrolo[2,3-b]pyridin-4-yl)-4-(1-amino-1-methy6lethyl)-3-cyanobenzamide

EXAMPLE 61
N-(4-pyridyl)-4-(1-aminoethyl)-3-aminomethylbenzamide

EXAMPLE 62
N-(4-pyridyl)-4-(1-aminoethyl)-3-methoxybenzamide

EXAMPLE 63
N-(1H-pyrazolo[3,4-b]pyridin-4-yl)-4-(1-aminoethyl)-3-methoxybenzamide

EXAMPLE 64
N-(1H-pyrrolo[2,3-b]pyridin-4-yl)-4-(1-aminoethyl)-3-methoxybenzamide

EXAMPLE 65
N-(4-pyridyl)-4-(1-aminoethyl)-2-methylbenzamide

EXAMPLE 66
N-(1H-pyrazolo[3,4-b]pyridin-4-yl)-4-(1-aminoethyl)-2-methylbenzamide

EXAMPLE 67
N-(1H-pyrrolo[2,3-b]pyridin-4-yl)-4-(1-aminoethyl)-2-methylbenzamide

EXAMPLE 68
N-(4-pyridyl)-4-(1-aminoethyl)-2-fluorobenzamide

EXAMPLE 69
N-(1H-pyrazolo[3,4-b]pyridin-4-yl)-4-(1-aminoethyl)-2-fluorobenzamide

EXAMPLE 70
N-(1H-pyrrolo[2,3-b]pyridin-4-yl)-4-(1-aminoethyl)-2-fluorobenzamide

EXAMPLE 7 1
(R)-(+)-N-(4-pyridyl-4-(1-aminoethyl)-2-chlorobenzamide dihydrobromide monohydrate, m.p. 248° C. (dec.), $[\alpha]_D$=+4.7° (methanol, c=0.5) (Compound 142)

EXAMPLE 72
N-(1H-pyrazolo[3,4-b]pyridin-4-yl)-4-(1-aminoethyl)-2-chlorobenzamide

EXAMPLE 73
N-(1H-pyrrolo[2,3-b]pyridin-4-yl)-4-(1-aminoethyl)-2-chlorobenzamide

EXAMPLE 74
N-(4-pyridyl)-4-(1-aminoethyl)-2-bromobenzamide

EXAMPLE 75
N-(1H-pyrazolo[3,4-b]pyridin-4-yl)-4-(1-aminoethyl)-2-bromobenzamide

EXAMPLE 76
N-(1H-pyrrolo[2,3-b]pyridin-4-yl)-4-(1-aminoethyl)-2-bromobenzamide EXAMPLE 77
N-(4-pyridyl)-2-amino-4-(1-aminoethyl)benzamide
EXAMPLE 78
N-(1H-pyrazolo[3,4-b]pyridin-4-yl)-2-amino-4-(1-aminoethyl)benzamide
EXAMPLE 79
N-(1H-pyrrolo[2,3-b]pyridin-4-yl)-2-amino-4-(1-aminoethyl)benzamide
EXAMPLE 80
N-(4-pyridyl)-4-(1-amino-2-fluoroethyl)benzamide
EXAMPLE 81
N-(4-pyridyl)-4-(1-amino-2,2,2-trifloroethyl)benzamide
EXAMPLE 82
N-(4-pyridyl)-4-(1-amino-1-cyclopropyl)benzamide
EXAMPLE 83
N-(1H-pyrazolo[3,4-b]pyridin-4-yl)-4-(1-amino-1-cylclopropyl)benzamide
EXAMPLE 84
N-(1H-pyrrolo[2,3-b]pyridin-4-yl)-4-(1-amino-1-cyclopropyl)benzamide
EXAMPLE 85
N-(4-pyridyl)-4-(1-amino-1-propyl)benzamide
EXAMPLE 86
N-(4-pyridyl)-4-aminomethyl-3,5-difluorobenzamide
EXAMPLE 87
N-(1H-pyrazolo[3,4-b]pyridin-4-yl)-4-aminomethyl-3,5-difluorobenzamide
EXAMPLE 88
N-(1H-pyrrolo[2,3-b]pyridin-4-yl)-4-aminomethyl-3,5-difluorobenzamide
EXAMPLE 89
N-(4-pyridyl)-4-aminomethyl-3,5-dimethylbenzamide
EXAMPLE 90
N-(1H-pyrazolo[3,4-b]pyridin-4-yl)-4-aminomethyl-3,5-dimethylbenzamide
EXAMPLE 91
N-(1H-pyrrolo[2,3-b]pyridin-4-yl)-4-aminomethyl-3,5-dimethylbenzamide
EXAMPLE 92
N-(4-pyridyl)-4-(1-aminoethyl)-3-carbamoylbenzamide
EXAMPLE 93
N-(1H-pyrazolo[3,4-b]pyridin-4-yl)-4-(1-aminoethyl)-3-carbamoylbenzamide
EXAMPLE 94
N-(1H-pyrrolo[2,3-b]pyridin-4-yl)-4-(1-aminoethyl)-3-carbamoylbenzamide
EXAMPLE 95
N-(4-pyridyl)-4-(1-aminoethyl)-3-methylcarbamoylbenzamide
EXAMPLE 96
N-(1H-pyrazolo[3,4-b]pyridin-4-yl)-4-(1-aminoethyl)-3-methylcarbamoylbenzamide
EXAMPLE 97
N-(1H-pyrrolo[2,3-b]pyridin-4-yl)-4-(1-aminoethyl)-3-methylcarbamoylbenzamide
EXAMPLE 98
N-(4-pyridyl)-4-(1-aminoethyl)-3-methylthiobenzamide
EXAMPLE 99
N-(4-pyridyl)-4-(1-aminoethyl)-3-methylsulfonylbenzamide
EXAMPLE 100
N-(1H-2,3-dihydropyrrolo[2,3-b]pyridin-4-yl)-4-(1-aminoethyl)benzamide
EXAMPLE 101
N-(1H-2,3-dihydro-2-oxopyrrolo[2,3-b]pyridin-4-yl)-4-(1-aminoethyl)benzamide
EXAMPLE 102
N-(1H-3-methylpyrrolo[2,3-b]pyridin-4-yl)-4-(1-aminoethyl)benzamide
EXAMPLE 103
N-(1H-2,3-dimethylpyrrolo[2,3-b]pyridin-4-yl)-4-(1-aminoethyl)benzamide
EXAMPLE 104
N-(1H-3-methylpyrrolo[3,4-b]pyridin-4-yl)-4-(1-aminoethyl)benzamide
EXAMPLE 105-a
N-(2-amino-4-pyridyl)-4-(1-aminoethyl)benzamide
EXAMPLE 105-b
N-(2-acetylamino-4-pyridyl)-4-(1-aminoethyl)benzamide
EXAMPLE 106
N-(4-pyridyl)-4-(1-aminomethyl-1-methylethyl)benzamide
EXAMPLE 107
N-(4-pyridyl)-4-(2-amino-2-methylpropyl)benzamide
EXAMPLE 108
2-(1-aminoethyl)-5-(4-pyridylcarbamoyl)benzoic acid
EXAMPLE 109
2-(1-aminoethyl)-5-((1H-pyrrolo[2,3-b]pyridin-4-yl)carbamoyl)benzoic acid
EXAMPLE 110
N-(1H-pyrrolo[2,3-b]pyridin-4-yl)-4-guanidinomethylbenzamide
EXAMPLE 111
N-(1H-2,3-dihydropyrrolo[2,3-b]pyridin-4-yl)-4-guanidinomethylbenzamide
EXAMPLE 112
N-(1H-2,3-dimethylpyrrolo[2,3-b]pyridin-4-yl)-4-guanidinomethylbenzamide
EXAMPLE 113
N-(1H-2,3-dihydro-2-oxopyrrolo[2,3-b]pyridin-4-yl)-4-guanidinomethylbenzamide
EXAMPLE 114
N-(1H-3-methylpyrrolo[2,3-b]pyridin-4-yl)-4-guanidinomethylbenzamide
EXAMPLE 115
N-(1H-3-methylpyrazolo[3,4-b]pyridin-4-yl)-4-guanidinomethylbenzamide
EXAMPLE 116
N-(4-pyridyl)-4-(1-guanidinoethyl)benzamide
EXAMPLE 117
N-(1H-pyrazolo[3,4-b]pyridin-4-yl)-4-(1-guanidinoethyl)benzamide
EXAMPLE 118
N-(1H-pyrrolo[2,3-b]pyridin-4-yl)-4-(1-guanidinoethyl)benzamide

EXAMPLE 119
N-(4-pyridyl)-4-(1-guanidino-1-methylethyl) benzamide

EXAMPLE 120
N-(1H-pyrazolo[3,4-b]pyridin-4-yl)-4-(1-guanidino-1-methylethyl)benzamide

EXAMPLE 121
N-(1H-pyrrolo[2,3-b]pyridin-4-yl)-4-(3-methylguanidino)methylbenzamide

EXAMPLE 122
N-(4-pyridyl)-4-(3-ethylguanidino)methylbenzamide

EXAMPLE 123
N-(1H-pyrazolo[3,4-b]pyridin-4-yl)-4-(3-ethylguanidino)methylbenzamide

EXAMPLE 124
N-(1H-pyrrolo[2,3-b]pyridin-4-yl)-4-(3-ethylguanidino)methylbenzamide

EXAMPLE 125
N-(1H-pyrazolo[3,4-b]pyridin-4-yl)-4-(3-propylguanidino)methylbenzamide

EXAMPLE 126
N-(1H-pyrrolo[2,3-b]pyridin-4-yl)-4-(3-propylguanidino)methylbenzamide

EXAMPLE 127
R-(+)-N-(1H-pyrrolo[2,3-b]pyridin-4-yl)-4-(1-(3-propylguanidino)ethyl)benzamide dihydrochloride dihydrate, m.p. 205–210° C. (dec.), $[\alpha]_D=+9.3°$ (methanol, c=0.5) (Compound 456)

EXAMPLE 128
N-(1H-pyrazolo[3,4-b]pyridin-4-yl)-4-(3-butylguanidino)methylbenzamide

EXAMPLE 129
N-(1H-pyrrolo[2,3-b]pyridin-4-yl)-4-(3-butylguanidino)methylbenzamide

EXAMPLE 130
N-(1H-pyrazolo[3,4-b]pyridin-4-yl)-4-(3-phenylguanidino)methylbenzamide

EXAMPLE 131
N-(1H-pyrrolo[2,3-b]pyridin-4-yl)-4-(3-phenylguanidino)methylbenzamide

EXAMPLE 132
N-(1H-pyrazolo[3,4-b]pyridin-4-yl)-4-(3-benzylguanidino)methylbenzamide

EXAMPLE 133
N-(1H-pyrrolo[2,3-b]pyridin-4-yl)-4-(3-benzylguanidino)methylbenzamide

EXAMPLE 134
N-(1H-pyrazolo[3,4-b]pyridin-4-yl)-4-(3-(2-phenylethyl)guanidino)methylbenzamide

EXAMPLE 135
N-(1H-pyrrolo[2,3-b]pyridin-4-yl)-4-(3-(2-phenylethyl)guanidino)methylbenzamide

EXAMPLE 136
N-(1H-pyrazolo[3,4-b]pyridin-4-yl)-4-(3,3-dimethylguanidino)methylbenzamide

EXAMPLE 137
N-(1H-pyrrolo[2,3-b]pyridin-4-yl)-4-(3,3-dimethylguanidino)methylbenzamide

EXAMPLE 138
N-(1H-pyrazolo[3,4-b]pyridin-4-yl)-4-(2,3-dimethylguanidino)methylbenzamide

EXAMPLE 139
N-(1H-pyrrolo[2,3-b]pyridin-4-yl)-4-(2,3-dimethylguanidino)methylbenzamide

EXAMPLE 140
N-(1H-pyrazolo[3,4-b]pyridin-4-yl)-4-(2,3-diethylguanidino)methylbenzamide

EXAMPLE 141
N-(1H-pyrrolo[2,3-b]pyridin-4-yl)-4-(2,3-diethylguanidino)methylbenzamide

EXAMPLE 142
N-(1H-pyrazolo[3,4-b]pyridin-4-yl)-4-(imidazolin-2-yl)-aminomethylbenzamide

EXAMPLE 143
N-(1H-pyrrolo[2,3-b]pyridin-4-yl)-4-(imidazolin-2-yl)-aminomethylbenzamide

EXAMPLE 144
N-(1H-pyrazolo[3,4-b]pyridin-4-yl)-4-(imidazol-2-yl)-aminomethylbenzamide

EXAMPLE 145
N-(1H-pyrrolo[2,3-b]pyridin-4-yl)-4-(imidazol-2-yl)-aminomethylbenzamide

EXAMPLE 146
N-(1H-pyrazolo[3,4-b]pyridin-4-yl)-4-(pyrimidin-2-yl)-aminomethylbenzamide

EXAMPLE 147
N-(1H-pyrrolo[2,3-b]pyridin-4-yl)-4-(pyrimidin-2-yl)-aminomethylbenzamide

EXAMPLE 148
N-(1H-pyrazolo[3,4-b]pyridin-4-yl)-4-(thiazol-2-yl)-aminomethylbenzamide

EXAMPLE 149
N-(1H-pyrrolo[2,3-b]pyridin-4-yl)-4-(thiazol-2-yl)-aminomethylbenzamide

EXAMPLE 150
R-(−)-N-(1H-pyrrolo[2,3-b]pyridin-4-yl)-4-(1-aminoethyl)-3-azidobenzamide dihydrobromide ½ hydrate (Compound 555)

(a) Sodium nitrite (440 mg) was added to a mixture of methyl (R)-3-amino-4-(1-acetylaminoethyl)benzoate (1.38 g), conc. hydrochloric acid (3 ml) and water (9 ml) under ice-cooling, and the mixture was stirred at the same temperature for 30 minutes. A solution of sodium azide (420 mg) in water (5 ml) was added, and the mixture was stirred for 30 minutes. After the reaction, the mixture was extracted with ethyl acetate, and washed with water. The mixture was dried, and the solvent was evaporated to give methyl (R)-4-(1-acetylaminoethyl)-3-azidobenzoate as white crystals.

(b) A solution of methyl (R)-4-(1-acetylaminoethyl)-3-azidobenzoate (1.6 g) in 2N hydrochloric acid (25 ml) was refluxed under heating for 8 hours. After the reaction, the mixture was concentrated under reduced pressure, and boiled with toluene to give crude (R)-3-azido-4-(1-aminoethyl)benzoic acid (1.7 g). Then, the mixture was added to a solution of sodium hydroxide (0.85 g) in water (25 ml). Benzyloxycarbonyl chloride (1.56 g) was dropwise added, and the mixture was stirred at room temperature for 5 hours. After the reaction, the solution was adjusted to have pH 4 with conc. hydrochloric acid. The mixture was extracted with chloroform, washed with water, and dried. The solvent was concentrated under reduced pressure. The obtained residue was purified by silica gel column chromatography (chloroform:methanol=30:1) to give 1.6 g of pale-yellow (R)-3-azido-4-(1-benzyloxycarbonylaminoethyl) benzoic acid.

(c) Thionyl chloride (4 ml) and dimethylformamide (1 drop) were added to a solution of (R)-3-azido-4-(1-benzyloxycarbonylaminoethyl)benzoic acid in dichloromethane (20 ml), and the mixture was refluxed under heating for 2 hours. After the reaction, the solvent was evaporated under reduced pressure. The obtained residue was boiled with benzene to give 1.65 g of (R)-3-azido-4-(1-benzyloxycarbonylaminoethyl)benzoyl chloride as yellow crystals.

Then, diisopropylethylamine (730 mg) was added to a solution of 4-amino-1-tert-butoxycarbonyl-1H-pyrrolo[2,3-b]pyridine in dichloromethane (5 ml) and acetonitrile (25 ml), and a solution of (R)-3-azido-4-(1-benzyloxycarbonylaminoethyl)benzoyl chloride in dichloromethane (10 ml) was dropwise added, which was followed by stirring at room temperature for 4 hours. After the reaction, water was added to the reaction mixture. The mixture was extracted with chloroform, washed with water, and dried. The solvent was evaporated under reduced pressure. The obtained residue was purified by silica gel column chromatography (chloroform:methanol=50:1) to give 2.0 g of (R)-N-(1-tert-butoxycarbonyl-1H-pyrrolo[2,3-b]pyridin-4-yl)-3-azido-4-(2-benzloxycarbonylaminoethyl)benzamide as a yellow amorphous.

(d) (R)-N-1-tert-Butoxycarbonyl-1H-pyrrolo[2,3-b]pyridin-4-yl)-3-azido-4-(2-benzyloxycarbonylaminoethyl)benzamide (2.0 g) was dissolved in 98% formic acid (25 ml), and the mixture was stirred for 1 hour. After the reaction, the solvent was evaporated under reduced pressure. Chloroform (120 ml) was added to the obtained residue. The mixture was washed with 1N sodium hydroxide (10 ml×2) and water, and dried. The solvent was evaporated under reduced pressure. To the obtained residue was added ethanol-ethyl acetate for crystallization. The mixture was recrystallized from chloroform-ethanol to give 600 mg of (R)-N-(1H-pyrrolo[2,3-b]pyridin-4-yl)-3-azido-4-(1-benzyloxycarbonylaminoethyl)benzamide as white crystals.

(e) A 25% hydrogen bromide-acetic acid solution (4 ml) was added to (R)-N-(1H-pyrrolo[2,3-b]pyridin-4-yl)-3-azido-4-(1-benzyloxycarbonylaminoethyl)benzamide (400 mg), and the mixture was stirred at room temperature for 1.5 hours. After the reaction, the solvent was evaporated under reduced pressure. The obtained crystals were recrystallized from ethanol-ethyl acetate to give 285 mg of (R)-(−)-N-(1H-pyrrolo[2,3-b]pyridin-4-yl)-4-(1-aminoethyl)-3-azidobenzamide dihydrobromide ½ hydrate having a melting point of 216–219° C. (dec.) as white crystals.

$[\alpha]_D$=−14.4° (methanol, c=0.5)

EXAMPLE 151

(R)-(+)-N-(4-pyridyl)-4-(1-aminoethyl)-2-nitrobenzamide dihydrobromide ½ hydrate, m.p. 240–244° C. (dec.), $[\alpha]_D$=+3.7° (methanol, c=0.5) (Compound 126)

EXAMPLE 152

(R)-(−)-N-(4-pyridyl)-4-(1-aminoethyl)-3-ethoxybenzamide dihydrochloride ½ hydrate, m.p. 288° C. (dec.), $[\alpha]_D$=−7.7° (methanol, c=0.5) (Compound 121)

EXAMPLE 153

(R)-(+)-N-(3-iodo-1H-pyrrolo[2,3-b]pyridin-4-yl)-4-(1-aminoethyl)benzamide dihydrochloride ½ hydrate (Compound 571)

Chloramine-T (18 mg) was added to a mixture of (R)-N-(1H-pyrrolo-[2,3-b]pyridin-4-yl)-4-(1-aminoethyl)benzamide (20 mg) and an aqueous solution (2 ml) of methyl iodide (10 mg) under ice-cooling, and the mixture was stirred at the same temperature for 1 hour. After the reaction, 5% sodium thiosulfate (0.17 ml) and 1N sodium hydroxide (2 ml) were added. The mixture was extracted with chloroform-methanol (10:1), washed with water and dried. The solvent was evaporated under reduced pressure. A hydrochloric acid-methanol solution (1 ml) was added to the obtained crystals to give hydrochloride thereof. The hydrochloride was recrystallized from methanol-ether to give 15 mg of (R)-(+)-N-(3-iodo-1H-pyrrolo[2,3-b]pyridin-4-yl)-4-(1-aminoethyl)benzamide dihydrochloride ½ hydrate having a melting point of 244–248° C. (dec.) as pale-yellow crystals.

$[\alpha]_D$=+8.5° (methanol, c=0.1)

EXAMPLE 154

(R)-(+)-N-(3-iodo-1H-pyrrolo[2,3-b]pyridin-4-yl)-4-(1-aminoethyl)- 3-azidobenzamide, m.p. 185–198° C. (dec.), $[\alpha]_D$=+13.5° (methanol, c=0.05) (Compound 556)

EXAMPLE 155

(R)-(−)-N-(4-pyridyl)-4-(1-aminoethyl)-3-hydroxybenzamide dihydrochloride, m.p. 262–266° C. (dec.), $[\alpha]_D$=−7.9° (methanol, c=0.5) (Compound 117)

EXAMPLE 156

N-(1H-pyrazolo[3,4-b]pyridin-4-yl)-4-guanidinomethyl-3-nitrobenzamide dihydrobromide monohydrate, m.p. 185–189° C. (dec.) (Compound 560)

EXAMPLE 157

(R)-N-(1H-pyrazolo[3,4-b]pyridin-4-yl)-4-(1-guanidinoethyl)-3-nitrobenzamide dihydrobromide monohydrate (Compound 561)

m.p. 265–275° C. (dec.)

PMR (DMSO-$d_6$/TMS) δ: 1.60 (3H,d,J=6.8 Hz), 4.00–5.00 (4H, brs), 5.27(1H,qd,J=6.8,1.9 Hz), 7.00–7.50 (3H,m), 7.75(1H,m), 7.83(1H,m), 8.30–8.60(4H,m), 8.65 (1H,d,J=1.9 Hz), 11.19(1H,brs), 13.00(1H,m)

EXAMPLE 158

N-(1H-pyrazolo[3,4-b]pyridin-4-yl)-4-guanidinomethyl-2-nitrobenzamide (Compound 562)

EXAMPLE 159

(R)-N-(1H-pyrazolo[3,4-b]pyridin-4-yl)-4-(1-aminoethyl)-2-nitrobenzamide dihydrobromide monohydrate (Compound 360)

(a) (R)-(1-(N-Benzyloxycarbonyl)aminoethyl)-2-nitrobenzoic acid (0.9 g) was dissolved in thionyl chloride (5 ml), and the solution was stirred at room temperature for 1 hour. After the reaction, the reaction mixture was concentrated under reduced pressure, and further boiled three times with toluene to give (R)-(1-(N-benzyloxycarbonyl)aminoethyl)-2-nitrobenzoyl chloride as a yellow oil. Then, a solution of (R)-(1-(N-benzyloxycarbonyl)aminoethyl)-2-nitrobenzoyl chloride in dichloromethane (5 ml) was dropwise added to a mixture of 4-amino-1-trityl-1H-pyrazolo[3,4-b]pyridine (1 g), triethylamine (0.74 ml) and dichloromethane (7 ml), and the mixture was stirred at room temperature for 2.5 hours. After the reaction, the reaction mixture was washed with water (50 ml) and dried. The solvent was evaporated under reduced pressure to give 1.5 g of (R)-N-(1-trityl-1H-pyrazolo[3,4-b]pyridin-4-yl)-4-(1-(N-benzyloxycarbonyl)aminoethyl)-2-nitrobenzamide as a yellow solid.

m.p. 159–161° C.

PMR (CDCl$_3$/TMS) δ: 1.40(3H,d,J=6.2 Hz), 4.75(1H,m), 4.92(1H,d,J=2.2 Hz), 5.00(1H,d,J=2.2 Hz), 5.23(1H,m), 7.00–7.40(17H,m), 7.56(1H,s),7.90(1H,s), 8.15(1H,s), 8.35(1H,m), 9.08(1H,brs)

(b) (R)-N-(1-Trityl-1H-pyrazolo[3,4-b]pyridin-4-yl)-4-(1-(N-benzyloxycarbonyl)aminoethyl)-2-nitrobenzamide (0.5 g) was dissolved in a 25% hydrobromic acid-acetic acid solution, and the solution was stirred at room temperature for 1.5 hours. After the reaction, the reaction mixture was concentrated under reduced pressure. The obtained residue was washed with a mixed solvent of hexane-ethyl acetate, and crystallized from a mixed solvent of methanol-ethyl acetate to give 0.31 g of (R)-N-(1H-pyrazolo[3,4-b]pyridin-4-yl)-4-(1-aminoethyl)-2-nitrobenzamide dihydrobromide monohydrate as pale-yellow crystals.

m.p. 220–225° C. (dec.)

PMR (DMSO-d$_6$/TMS) δ: 1.56(3H,d,J=6.9 Hz), 4.00–5.00(4H,brs), 4.72(1H,m), 7.90(1H,m), 7.98(1H,d,J=7.8 Hz), 8.05(1H,d,J=7.8 Hz), 8.44–8.56(6H,m), 11.61(1H,brs)

EXAMPLE 160

(R)-N-(1H-pyrazolo[3,4-b]pyridin-4-yl)-4-(1-guanidinoethyl)-2-nitrobenzamide (Compound 563)

y (a) N,N'-dibenzyloxycarbonyl-S-methylisothiourea (215 mg) was added to a mixture of (R)-N-(1H-pyrazolo[3,4-b]pyridin-4-yl)-4-(1-aminoethyl)-2-nitrobenzamide dihydrobromide monohydrate (224 mg), triethylamine (0.25 ml) and methanol (5 ml) at room temperature, and the mixture was stirred at room temperature for 14 hours and at 40° C. for 7.5 hours. After the reaction, the reaction mixture was concentrated under reduced pressure. The obtained residue was purified by silica gel column chromatography to give 166 mg of (R)-N-(1H-pyrazolo[3,4-b]pyridin-4-yl)-4-(1-(2',3'-dibenzyloxycarbonyl)guanidinoethyl))-2-nitrobenzamide as a pale-yellow oil.

(b) (R)-N-(1H-Pyrazolo[3,4-b]pyridin-4-yl)-4-(1-(2',3'-dibenzyloxycarbonyl)guanidinoethyl))-2-nitrobenzamide (165 mg) was dissolved in a 25% hydrobromic acid-acetic acid solution (3 ml), and the mixture was stirred at 40° C. for 5 hours. After the reaction, the reaction mixture was concentrated under reduced pressure. The obtained residue was crystallized from a mixed solvent of methanol-ethyl acetate, and recrystallized from the same solvent to give 140 mg of (R)-N-(1H-pyrazolo[3,4-b]pyridin-4-yl)-4-(1-guanidinoethyl))-2-nitrobenzamide as white crystals.

PMR (DMSO-d$_6$/TMS) δ: 1.57(3H,d,J=6.8 Hz), 4.00–4.50(4H, brs), 5.20(1H,m), 7.00–7.40(3H,m), 7.80–9.00(7H,m), 11.47(1H,m), 13.00(1H,m)

EXAMPLE 161

(R)-N-(1H-pyrazolo[3,4-b]pyridin-4-yl)-4-(1-aminoethyl)-2-azidobenzamide (Compound 558)

EXAMPLE 162

(R)-N-(1H-pyrazolo[3,4-b]pyridin-4-yl)-2-azido-4-(1-guanidinoethyl)benzamide (Compound 565)

EXAMPLE 163

(R)-5-((1H-pyrazolo[3,4-b]pyridin-4-yl)carbamoyl)-2-(1-aminoethyl)benzoic acid (Compound 369)

EXAMPLE 164 methyl (R)-5-((1H-pyrazolo[3,4-b]pyridin-4-yl)carbamoyl)-2-(1-aminoethyl)benzoate (Compound 371)

EXAMPLE 165

N-(1H-pyrazolo[3,4-b]pyridin-4-yl)-3,5-dimethyl-4-guanidinomethylbenzamide (Compound 566)

EXAMPLE 166

N-(1H-pyrazolo[3,4-b]pyridin-4-yl)-4-guanidinobenzamide dihydrobromide monohydrate (Compound 567)

m.p. 286–290° C. (dec.)

PMR (DMSO-d$_6$/TMS) δ: 3.80–4.30(4H,brs), 7.42(2H,d, J=8.7 Hz), 7.60–7.80(4H,m), 8.10(2H,d,J=8.7 Hz), 8.51(1H, m), 9.96(1H,s), 10.98(1H,brs)

EXAMPLE 167

(R)-N-(1H-pyrazolo[3,4-b]pyridin-4-yl)-4-(1-aminoethyl)-3-nitrobenzamide dihydrobromide monohydrate (Compound 359)

m.p. 198–210° C. (dec.)

PMR (DMSO-d$_6$/TMS) δ: 1.61(3H,d,J=6.9 Hz), 3.60–4.00(4H,brs), 5.90(1H,m), 7.75(1H,m), 8.05(1H,m), 8.31–8.48(6H,m), 8.64(1H,s), 11.14(1H,brs)

EXAMPLE 168

(R)-N-(1H-pyrazolo[3,4-b]pyridin-4-yl)-4-(1-(imidazol-2-yl)ethyl)benzamide (Compound 526)

EXAMPLE 169

(R)-N-(1H-pyrrolo[2,3-b]pyridin-4-yl)-4-(1-aminoethyl)-3-nitrobenzamide (Compound 311)

EXAMPLE 170

(R)-N-(1H-pyrazolo[3,4-b]pyridin-4-yl)-4-(1-aminoethyl)-3-azidobenzamide (Compound 557)

EXAMPLE 171

(R)-N-(4-pyridyl)-4-(1-guanidinoethyl)benzamide (Compound 396)

EXAMPLE 172

(R)-N-(1H-pyrazolo[3,4-b]pyridin-4-yl)-4-(1-guanidinoethyl)benzamide dihydrochloride monohydrate (Compound 511)

m.p. 210–216° C. (dec.)

PMR (CMSO-$d_6$/TMS) δ: 1.46(3H,d,J=6.8 Hz), 4.01(4H, m), 4.91(1H,m), 7.24(3H,m), 7.54(2H,d,J=8.3 Hz), 7.80(1H, m), 8.00(2H,d,J=8.3 Hz), 8.48(3H,m), 11.00(1H,m), 13.75 (1H,m)

EXAMPLE 173

(R)-N-(1H-pyrrolo[2,3-b]pyridin-4-yl)-4-(1-guanidinoethyl)benzamide (Compound 118)

EXAMPLE 174

N-(1H-pyrazolo[3,4-b]pyridin-4-yl)-4-(1-amino-2-hydroxyethyl)benzamide dihydrobromide monohydrate (Compound 568)

(a) Sodium borohydride (296 mg) was gradually added to a solution of N-benzyloxycarbonyl-4-methoxycarbonylphenylglycine (700 mg) in methanol (20 ml) at room temperature, and the mixture was stirred at the same temperature for 4 hours. After the reaction, the solvent was evaporated under reduced pressure. 1N Hydrochloric acid was added to the obtained residue. The mixture was extracted with chloroform, washed with water and dried. The solvent was evaporated under reduced pressure. The obtained crystals were recrystallized from ethyl acetate-hexane to give 510 mg of methyl 4-(1-(N-benzyloxycarbonyl)amino-2-hydroxyethyl)benzoate as a white powder.

PMR (CDCl$_3$/TMS) δ: 3.86(1H,m), 3.89(3H,s), 3.92(2H, d,J=8 Hz), 4.88(1H,brs), 5.08(2H,m), 7.20–7.50(17H,m), 8.00(2H,d,J=8 Hz)

(b) Diisopropylethylamine (0.418 ml) and trityl bromide (740 mg) were added to a solution of methyl 4-(1-(N-benzyloxycarbonyl)amino-2-hydroxyethyl)benzoate (500 mg) in dichloromethane (20 ml), and the mixture was stirred at room temperature for 9 hours. After the reaction, water was added to the reaction mixture. The mixture was extracted with dichloromethane, washed with water and dried. The solvent was evaporated under reduced pressure. The obtained residue was purified by silica gel column chromatography to give 890 mg of methyl 4-(1-(N-benzyloxycarbonyl)amino-2-tritryloxyethyl)benzoate (890 mg) as pale-yellow crystals.

PMR (CDCl$_3$/TMS) δ: 3.44(2H,d,J=8 Hz), 3.88(3H,s), 4.87(1H,brs), 5.02(2H,m), 5.48(1H,brs), 7.15–7.40(22H,m), 7.97(2H,d,J=8 Hz)

(c) An aqueous solution (5 ml) of sodium hydroxide (62 mg) was added to a mixture of methyl 4-(1-(N-benzyloxycarbonyl)amino-2-trityloxyethyl)benzoate (890 mg), methanol (20 ml) and dioxane (5 ml), and the mixture was refluxed under heating for 2 hours. After the reaction, the solvent was evaporated under reduced pressure. The obtained residue was purified by silica gel column chromatography to give 330 mg of 4-(1-(N-benzyloxycarbonyl)amino-2-trityloxyethyl)benzoic acid (330 mg).

PMR (CDCl$_3$/TMS) δ: 3.38(2H,brs), 4.90(1H,brs), 5.08 (2H,m), 5.55(1H,brs), 7.15–7.45(22H,m), 8.04(2H,d,J=8 Hz)

(d) Thionyl chloride (0.035 ml) and pyridine (0.04 ml) were added to a solution of 4-(1-(N-benzyloxycarbonyl)amino-2-trityloxyethyl)benzoic acid (200 mg) in dichloromethane (10 ml), and the mixture was stirred at room temperature for 1 hour. After the reaction, the reaction mixture was concentrated under reduced pressure. The residue was further boiled three times with toluene to give 4-(1-(N-benzyloxycarbonyl)amino-2-trityloxyethyl)benzoyl chloride as crystals. Then, a solution of 4-(1-(N-benzyloxycarbonyl)amino-2-trityloxyethyl)benzoyl chloride in dichloromethane (5 ml) was dropwise added to a mixture of 4-amino-1-trityl-1H-pyrazolo[3,4-b]pyridine (130 mg), diisopropylethylamine (0.08 ml) and dichloromethane (10 ml), and the mixture was stirred at room temperature for 4 hours. After the reaction, the reaction mixture was extracted with chloroform, washed with water and dried. The solvent was evaporated under reduced pressure. The obtained residue was purified by silica gel column chromatography to give 260 mg of N-(1-trityl-1H-pyrazolo [3,4-b]pyridin-4-yl)-4-(1-(N-benzyloxycarbonyl)amino-2-trityloxyethyl)benzamide as a pale-yellow oil.

PMR (CDCl$_3$/TMS) δ: 3.37(2H,brs), 4.80(1H,brs), 5.04 (2H,m), 5.50(1H,brs), 7.10–7.40(35H,m), 7.68(1H,d,J=4 Hz), 7.75(2H,d,J=8 Hz), 8.00(2H,d,J=8 Hz), 8.04(1H,s), 8.60(1H,brs), 8.64(1H,d,J=4 Hz)

(e) A 25% hydrobromic acid-acetic acid solution (10 ml) was added to N-(1-trityl-1H-pyrazolo[3,4-b]pyridin-4-yl)-4-(1-N-benzyloxycarbonyl)amino-2-trityloxyethyl) benzamide, and the mixture was stirred at room temperature for 1.5 hours. After the reaction, the mixture was concentrated under reduced pressure, and ethyl acetate was added. The obtained amorphous crystals were crystallized from methanol-ethyl acetate to give 60 mg of N-(1H-pyrazolo[3, 4-b]pyridin-4-yl)-4-(1-amino-2-hydroxyethyl)benzamide dihydrobromide monohydrate as pale-yellow amorphous crystals.

m.p. 214–216° C. (dec.)

PMR (DMSO-$d_6$/TMS) δ: 4.36(2H,d,J=4 Hz), 4.77(1H, m), 7.69(2H,d,J=8 Hz, 7.79(1H,brs), 8.08(2H,d,J=8 Hz), 8.45(1H, brs), 8.62(3H,brs), 10.91(1H,brs)

EXAMPLE 175

N-(1H-pyrazolo[3,4-b]pyridin-4yl)-4-aminomethyl-3,5-dimethylbenzamide (Compound 559)

EXAMPLE 176

2-amino-2-(4-((1H-pyrazolo[3,4-b]pyridin-4-yl)carbamoyl)phenyl)acetic acid (Compound 569)

EXAMPLE 177

N-(1H-pyrazolo[3,4-b]pyridin-4-yl)-4-aminomethyl-3-nitrobenzamide dihydrobromide dihydrate, m.p. 205–207° C. (Compound 572)

EXAMPLE 178

N-(1H-pyrazolo[3,4-b]pyridin-4-yl)-4-aminomethyl-2-cyanobenzamide (Compound 573)

EXAMPLE 179

(R)-N-(1H-pyrazolo[3,4-b]pyridin-4-yl)-4-(1-aminoethyl)-2-cyanobenzamide (Compound 392)

Formulation Example 1: Tablet

| | |
|---|---|
| Compound of the present invention | 10.0 mg |
| Lactose | 50.0 mg |
| Corn starch | 20.0 mg |
| Crystalline cellulose | 29.7 mg |
| Polyvinylpyrrolidone K30 | 5.0 mg |
| Talc | 5.0 mg |
| Magnesium stearate | 0.3 mg |
| | 120.0 mg |

The compound of the present invention, lactose, corn starch and crystalline cellulose were mixed. The mixture was kneaded with an adhesive solution of polyvinylpyrrolidone K30, and passed through a 20-mesh sieve to give granules. The particles were dried at 50° C. for 2 hours, and passed through a 24-mesh sieve. Talc and magnesium stearate were added, and the mixture was punched with a 7 mm diameter pounder to give tablets each weighing 120 mg.

FORMULATION EXAMPLE 2

Capsule

| | |
|---|---|
| Compound of the present invention | 10.0 mg |
| Lactose | 70.0 mg |
| Corn starch | 35.0 mg |
| Polyvinylpyrrolidone K30 | 2.0 mg |
| Talc | 2.7 mg |
| Magnesium stearate | 0.3 mg |
| | 120.0 mg |

The compound of the present invention, lactose, corn starch and crystalline cellulose were mixed. The mixture was kneaded with an adhesive solution of polyvinylpyrrolidone K30, and passed through a 20-mesh sieve to give granules. The particles were dried at 50° C. for 2 hours, and passed through a 24-mesh sieve. Talc and magnesium stearate were added, and the mixture was packed in hard capsule (No. 4) to give capsules each containing 120 mg.

What is claimed is:

1. A benzamide compound of the formula $$\begin{array}{c} R \\ | \\ N-A \\ | \\ R^1 \end{array} \begin{array}{c} R^2 \\ = = \\ = = \\ | \\ R^3 \end{array} \begin{array}{c} O \quad R^4 \\ \| \quad | \\ C-N-R^5 \end{array} \tag{I}$$

wherein

R is a hydrogen, an alkyl, or a cycloalkyl, a cycloalkylalkyl, a phenyl or an aralkyl, which optionally has a substituent on a ring, $R^1$ is a hydrogen, an alkyl, or a cycloalkyl, a cycloalkylalkyl, a phenyl or an aralkyl, which optionally has a substituent on a ring; or R and $R^1$ combined form, together with the adjacent nitrogen atom, a heterocycle optionally having oxygen atom, sulfur atom or optionally substituted nitrogen atom additionally in the ring;

$R^2$ and $R^3$ are the same or different and each is a hydrogen, an alkyl, an aralkyl, a halogen, a nitro, an amino, an alkylamino, an acylamino, a hydroxy, an alkoxy, an aralkyloxy, a cyano, an acyl, a mercapto, an alkylthio, an aralkylthio, a carboxy, an alkoxycarbonyl, a carbamoyl, an alkylcarbamoyl or an azide;

$R^4$ is a hydrogen or an alkyl;

$R^5$ is a nitrogen-containing optionally-substituted heterocyclic ring selected from the group consisting of pyrazolopyrimidine, 2,3-dihydropyrrolopyridine, imidazopyridine, pyrrolopyrimidine, imidazopyrimidine, pyrrolotriazine, pyrazolotriazine, triazolopyridine, triazolopyrimidine, and 2,3-dihydropyrrolopyrimidine; and A is the formula $$\begin{array}{c} R^{10} \\ | \\ -(CH_2)_l(C)_m(CH_2)_n- \\ | \\ R^{11} \end{array} \tag{III}$$

wherein $R^{10}$ and $R^{11}$ are the same or different and each is a hydrogen, alkyl, haloalkyl, aralkyl, hydroxyalkyl, carboxy or alkoxycarbonyl, or $R^{10}$ and $R^{11}$ combinedly form cycloalkyl, and l and n are each 0 or an integer of 1–3 and m is an integer of 1–3, an isomer thereof or a pharmaceutically acceptable acid addition salt thereof.

2. The benzamide compound of claim 1, wherein, in the formula (I), at least one of R, $R^2$, $R^3$, and A satisfy the following definitions:

R is hydrogen, alkyl, or aralkyl optionally having substituent on the ring;

$R^2$ and $R^3$ are the same or different and each is hydrogen, alkyl, halogen, nitro, amino hydroxy, alkoxy, aralkyloxy, cyano, acyl, carboxy, alkoxycarbonyl, carbamoyl or azide;

A is the formula

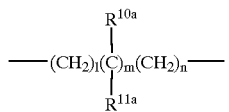
(III')

wherein $R^{10a}$ and $R^{11a}$ are the same or different and each is hydrogen, alkyl haloalkyl, hydroxyalkyl, carboxy or alkoxycarbonyl, or $R^{10a}$ and $R^{11a}$ combinedly form cycloalkyl, and l and n are each 0 or an integer of 1 to 3 and m is an integer of 1–3,
an isomer thereof or a pharmaceutically acceptable acid addition salt thereof.

3. The benzamide compound of claim 1, wherein, in the formula (I),
   $R^5$ is a nitrogen-containing optionally substituted heterocyclic ring selected from the group consisting of pyrazolopyrimidine, 2,3-dihydropyrrolopyridine, imidazopyridine, pyrrolopyrimidine, imidazopyrimidine, and 2,3-dihydropyrrolopyrimidine,
an isomer thereof or a pharmaceutically acceptable acid addition salt thereof.

4. The benzamide compound of claim 1, wherein, in the formula (I),
   $R^5$ is a nitrogen-containing optionally-substituted heterocyclic ring selected from the group consisting of 2,3-dihydropyrrolopyridine, 2,3-dihydro-2-oxopyrrolopyridine, and 2,3-dihydro-2,3-dioxopyrrolopyridine,
an isomer thereof or a pharmaceutically acceptable acid addition salt thereof.

5. The benzamide compound of claim 1, wherein the compound of the formula (I) is a member selected from the group consisting of the compounds of:
   N-(1H-2,3-dihydropyrrolo[2,3-b]pyridin-4-yl)-4-(1-aminomethyl)-benzamide,
   N-(1-methyl-2,3-dihydro-2-oxopyrrolo[2,3-b]pyridin-4-yl)-4-(1-aminomethyl)benzamide,
   N-(1H-2,3-dihydro-2,3-dioxopyrrolo[2,3-b]pyridin-4-yl)-4-(1-aminomethyl)benzamide,
   N-(1H-2,3-dihydro-2-oxopyrrolo[2,3-b]pyridin-4-yl)-4-(1-aminomethyl)benzamide,
   N-(1H-2,3-dihydropyrrolo[2,3-b]pyridin-4-yl)-4-(1-aminomethyl)benzamide,
   N-(1-methyl-2,3-dihydropyrrolo[2,3-b]pyridin-4-yl)-4-(1-aminoethyl)benzamide,
   N-(1H-2,3-dihydro-2,3-dioxopyrrolo[2,3-b]pyridin-4-yl)-4-(1-aminoethyl)benzamide, and
   N-(1H-2,3-dihydro-2-oxopyrrolo[2,3-b]pyridin-4-yl)-4-(1-aminoethyl)benzamide.

6. A pharmaceutical composition comprising a therapeutically effective amount of the benzamide compound of claim 1, an isomer thereof or a pharmaceutically acceptable acid addition salt thereof, and a pharmaceutically acceptable carrier, excipient or diluent.

7. A pharmaceutical composition for treating hypertension, comprising the benzamide compound of claim 1, an isomer thereof or a pharmaceutically acceptable acid addition salt thereof, and a pharmaceutically acceptable carrier, excipient or diluent.

8. A pharmaceutical composition for treating angina pectoris, comprising the benzamide compound of claim 1, an isomer thereof or a pharmaceutically acceptable acid addition salt thereof, and a pharmaceutically acceptable carrier, excipient or diluent.

9. A pharmaceutical composition for treating asthma, comprising the benzamide compound of claim 1, an isomer thereof or a pharmaceutically acceptable acid addition salt thereof, and a pharmaceutically acceptable carrier, excipient or diluent.

10. A pharmaceutical composition for treating renal and peripheral circulatory disturbances, comprising the benzamide compound of claim 1, an isomer thereof or a pharmaceutically acceptable acid addition salt thereof, and a pharmaceutically acceptable carrier, excipient or diluent.

11. A pharmaceutical composition for inhibiting cerebral vasospasm, comprising the benzamide compound of claim 1, an isomer thereof or a pharmaceutically acceptable acid addition salt thereof, and a pharmaceutically acceptable carrier, excipient or diluent.

12. A method for treating hypertension, comprising administering to a subject in need thereof a therapeutically effective amount of the benzamide compound of claim 1, an isomer thereof or a pharmaceutically aceptable acid addition salt thereof.

13. A method for treating angina pectoris, comprising administering to a subject in need thereof a therapeutically effective amount of the benzamide compound of claim 1, an isomer thereof or a pharmaceutically acceptable acid addition salt thereof.

14. A method for treating asthma, comprising administering to a subject in need thereof a therapeutically effective amount of the benzamide compound of claim 1, an isomer thereof or a pharmaceutically acceptable acid addition salt thereof.

15. A method for treating renal and peripheral circulatory disturbances, comprising administering to a subject in need thereof a therapeutically effective amount of the benzamide compound of claim 1, an isomer thereof or a pharmaceutically acceptable acid addition salt thereof.

16. A method for inhibiting cerebral vasospasm, comprising administering to a subject in need thereof a therapeutically effective amount of the benzamide compound of claim 1, an isomer thereof or a pharmaceutically acceptable acid addition salt thereof.

* * * * *